(12) United States Patent
Haack et al.

(10) Patent No.: US 9,365,632 B2
(45) Date of Patent: Jun. 14, 2016

(54) EXENDIN-4 DERIVATIVES AS DUAL GLP1/GLUCAGON AGONISTS

(71) Applicant: SANOFI, Paris (FR)

(72) Inventors: Torsten Haack, Frankfurt am Main (DE); Michael Wagner, Frankfurt am Main (DE); Bernd Henkel, Frankfurt am Main (DE); Siegfried Stengelin, Frankfurt am Main (DE); Andreas Evers, Frankfurt am Main (DE); Martin Bossart, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/049,597

(22) Filed: Oct. 9, 2013

(65) Prior Publication Data
US 2014/0100156 A1    Apr. 10, 2014

(30) Foreign Application Priority Data

Oct. 9, 2012   (EP) .................................... 12306232
Feb. 27, 2013  (EP) .................................... 13305222

(51) Int. Cl.
| | |
|---|---|
| *A61K 38/26* | (2006.01) |
| *C07K 14/575* | (2006.01) |
| *C07K 14/605* | (2006.01) |
| *A61K 38/28* | (2006.01) |
| *A61K 45/06* | (2006.01) |
| *A61K 38/22* | (2006.01) |
| *A61K 38/00* | (2006.01) |

(52) U.S. Cl.
CPC ............ *C07K 14/605* (2013.01); *A61K 38/2264* (2013.01); *A61K 38/26* (2013.01); *A61K 38/28* (2013.01); *A61K 45/06* (2013.01); *A61K 38/00* (2013.01)

(58) Field of Classification Search
None
See application file for complete search history.

(56) References Cited

U.S. PATENT DOCUMENTS

| | | |
|---|---|---|
| 5,424,286 A | 6/1995 | Eng |
| 6,858,576 B1 | 2/2005 | Young et al. |
| 9,181,305 B2 | 11/2015 | Haack et al. |
| 2009/0298757 A1 | 12/2009 | Bloom et al. |
| 2011/0152181 A1 | 6/2011 | Alsina-Fernandez et al. |
| 2011/0152182 A1 | 6/2011 | Alsina-Fernandez et al. |
| 2011/0237503 A1 | 9/2011 | Alsina-Fernandez et al. |
| 2012/0148586 A1 | 6/2012 | Chou et al. |
| 2014/0206608 A1 | 7/2014 | Haack et al. |
| 2014/0206609 A1 | 7/2014 | Haack et al. |
| 2014/0213513 A1 | 7/2014 | Haack et al. |
| 2014/0221281 A1 | 8/2014 | Haack et al. |
| 2015/0164995 A1 | 6/2015 | Kadereit et al. |
| 2015/0164996 A1 | 6/2015 | Kadereit et al. |
| 2015/0164997 A1 | 6/2015 | Haack et al. |
| 2015/0166625 A1 | 6/2015 | Haack et al. |
| 2015/0166627 A1 | 6/2015 | Kadereit et al. |
| 2015/0315260 A1 | 11/2015 | Bossart et al. |
| 2015/0322128 A1 | 11/2015 | Bossart et al. |
| 2015/0322129 A1 | 11/2015 | Bossart et al. |
| 2015/0368311 A1 | 12/2015 | Haack et al. |

FOREIGN PATENT DOCUMENTS

| | | |
|---|---|---|
| EP | 2 387 989 A2 | 11/2011 |
| WO | WO 2004/035623 A2 | 4/2004 |
| WO | 2006/017688 A2 | 2/2006 |
| WO | WO 2006/134340 A2 | 12/2006 |
| WO | 2007/056362 A2 | 5/2007 |
| WO | WO 2007/139941 A2 | 12/2007 |
| WO | 2008023050 A1 | 2/2008 |
| WO | WO 2008/071972 A1 | 6/2008 |
| WO | 2008/086086 A2 | 7/2008 |
| WO | WO 2008/081418 A1 | 7/2008 |
| WO | WO 2008/101017 A2 | 8/2008 |
| WO | WO 2008/152403 A1 | 12/2008 |
| WO | 2009/058662 A2 | 5/2009 |
| WO | 2009/058734 A1 | 5/2009 |
| WO | 2009/099763 A1 | 8/2009 |
| WO | 2009/143014 A1 | 11/2009 |
| WO | 2009/155257 A1 | 12/2009 |
| WO | WO 2009/155258 A2 | 12/2009 |
| WO | 2010/071807 A1 | 6/2010 |
| WO | WO 2010/070251 A1 | 6/2010 |
| WO | WO 2010/070252 A1 | 6/2010 |
| WO | WO 2010/070253 A1 | 6/2010 |
| WO | WO 2010/070255 A1 | 6/2010 |
| WO | WO 2010/096052 A1 | 8/2010 |
| WO | WO 2010/096142 A1 | 8/2010 |
| WO | 2010/138671 A1 | 12/2010 |
| WO | 2010/148089 A1 | 12/2010 |
| WO | WO 2011/006497 A1 | 1/2011 |
| WO | 2011024110 A2 | 3/2011 |
| WO | 2011/056713 A2 | 5/2011 |

(Continued)

OTHER PUBLICATIONS

Braga et al., "Making Crystals from Crystals: a green route to crystal engineering and polymorphism," Chem. Commun., 2005, pp. 3635-3645.*

(Continued)

*Primary Examiner* — Julie Ha
*Assistant Examiner* — Kristina M Hellman
(74) *Attorney, Agent, or Firm* — Lathrop & Gage LLP; James H. Velema, Esq.

(57) ABSTRACT

The present invention relates to exendin-4 derivatives and their medical use, for example in the treatment of disorders of the metabolic syndrome, including diabetes and obesity, as well as reduction of excess food intake.

38 Claims, 13 Drawing Sheets

(56) References Cited

FOREIGN PATENT DOCUMENTS

Figure 1A:
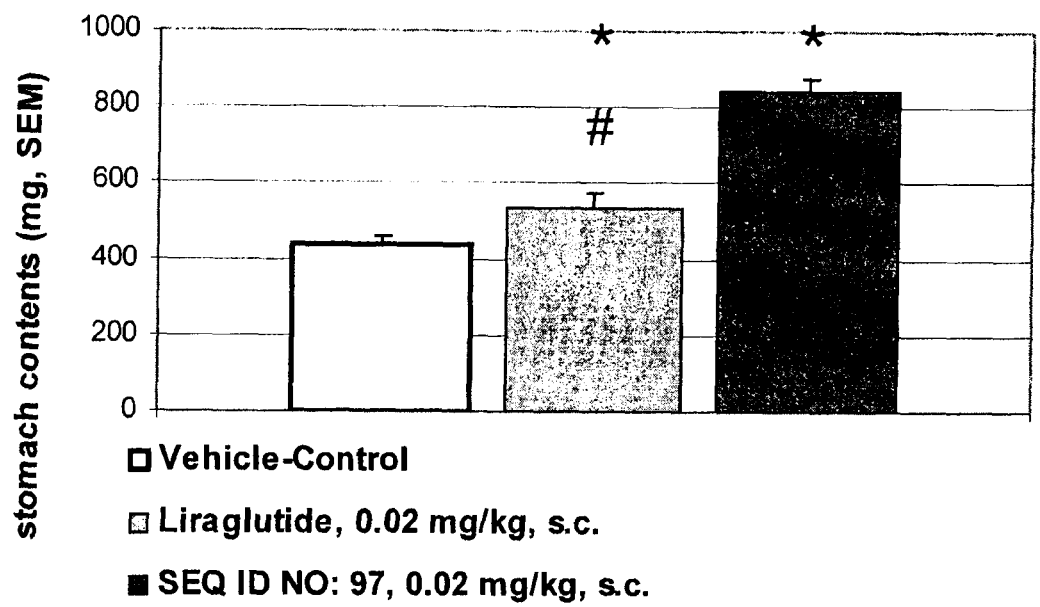
Figure 1B:
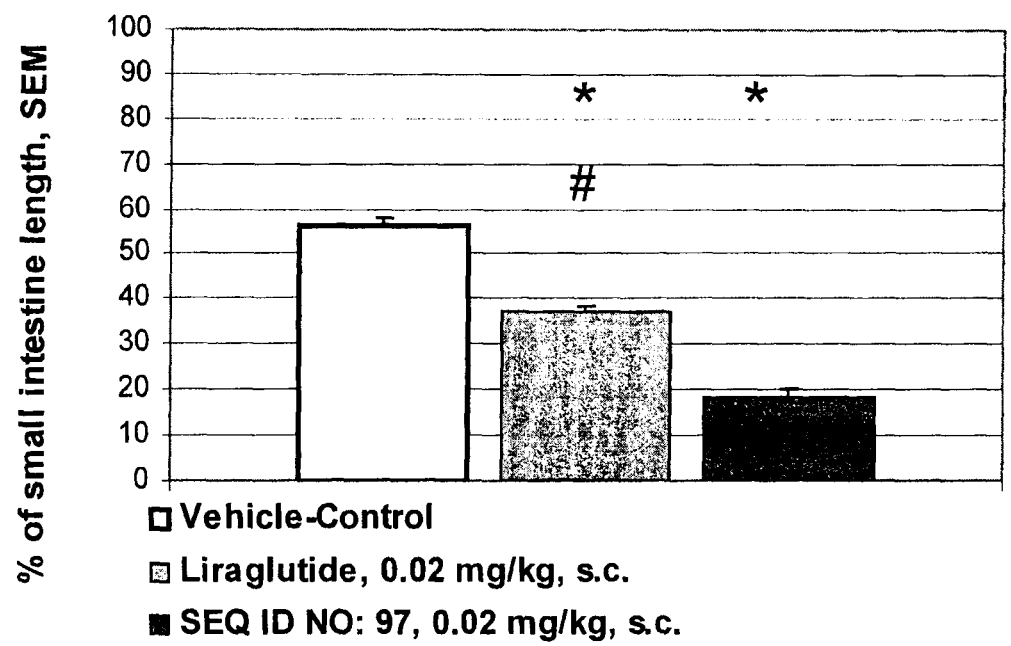

| WO | WO 2011/075393 A1 | 6/2011 |
| --- | --- | --- |
| WO | 2011/088837 A1 | 7/2011 |
| WO | 2011094337 A1 | 8/2011 |
| WO | WO 2011/117415 A1 | 9/2011 |
| WO | WO 2011/117416 A1 | 9/2011 |
| WO | 2011/143208 A1 | 11/2011 |
| WO | 2011/143209 A1 | 11/2011 |
| WO | 2011/156407 A2 | 12/2011 |
| WO | 2011/163012 A2 | 12/2011 |
| WO | 2011/163473 A1 | 12/2011 |
| WO | WO 2011/152181 A1 | 12/2011 |
| WO | WO 2011/152182 A1 | 12/2011 |
| WO | WO 2011/160630 A2 | 12/2011 |
| WO | 2012/088116 A2 | 6/2012 |
| WO | 2012/088157 A2 | 6/2012 |
| WO | 2012/169798 A2 | 12/2012 |
| WO | 2012/173422 A1 | 12/2012 |
| WO | 2012/177929 A2 | 12/2012 |
| WO | WO 2013/004983 A1 | 1/2013 |
| WO | 2013/074910 A1 | 5/2013 |
| WO | 2014/017843 A1 | 1/2014 |
| WO | 2014/073842 A1 | 5/2014 |
| WO | 2014/073845 A1 | 5/2014 |
| WO | 2014/152460 A2 | 9/2014 |
| WO | 2014/158900 A1 | 10/2014 |

OTHER PUBLICATIONS

Seddon, K.R., "Pseudopolymorph: a polemic," Crystal Growth & Design, 2004, 4(6), pp. 1087, web release date Oct. 19, 2004.*
Vippagunta et al. "Crystalline Solids," Advanced Drug Delivery Reviews, 2001, 48, pp. 3-26.*
Bunck, M.C. et al., Effects of Exenatide on Measures of B-Cell Function After 3 Years in Metformin—Treated Patients With Type 2 Diabetes, Diabetes Care, (Sep. 2011), vol. 34, pp. 2041-2047.
Buse, J.B. et al., Liraglutide once a day versus exenatide twice a day for type 2 diabetes: a 26-week randomised, parallel group, multinational, open-label trial (LEAD-6), The Lacenet, (Jul. 4, 2009), vol. 374, pp. 39-47.
Chhabra, S.R. et al., An Appraisal of New Variants of Dde Amine Protecting Group for Solid Phase Peptide Synthesis, Tetrahedron Letters, (1998), vol. 39, pp. 1603-1606.
Drucker, D.J. et al., Liraglutide, Nature Reviews Drug Disovery, (Apr. 2010), vol. 9, pp. 267-268.
Eng, J. et al., Isolation and Characterization of Exendin-4, an Exendin-3 Analogue, from Heloderma suspectum Venom, The Journal of Biological Chemistry, (Apr. 15, 1992), vol. 267, No. 11, pp. 7402-7405.
Eng, J. et al., Prolonged Effect of Exendin-4 on Hyperglycemia of db/db mice, Diabetes, (1996), vol. 45, pp. 152A, Abstract 554.
Gentilella, R. et al., Exenatide: a review from pharmacology to clinical practice, Diabetes, Obesity and Metabolism, (2009), vol. 11, pp. 544-556.
Hargrove, D.M. et al., Biological activity of AC3174, a peptide analog of exendin-4, Regulatory Peptides, (2007), vol. 141, pp. 113-119.
King, D.S. et al., A cleavage method which minimizes side reactions following Fmoc solid phase peptide synthesis, Int. J. Peptide. Protein Res., (1990), vol. 36, pp. 255-266.
Norris, S.L. et al., Exenatide efficacy and safety: a systematic review, Diabetic Medicine, (2009), vol. 26, pp. 837-846.
Byetta Product Information, Accessed Jun. 2, 2014 at http://www.accessdata.fda.gov/drugsatfda_docs/label/2008/021773s012lbl.pdf.
Siv A. Hjorth et al. 'Glucagon and Glucagon-like Peptide 1: Selective Receptor Recognition Via Distinct Peptide Epitopes'. The Journal of Biological Chemistry. 1994, vol. 269, No. 48, pp. 30121-30124.
Brian L. Furman, 'The Development of Byetta (exenatide) From the Venom of the Gilo Monster as an Anti-diabetic Agent'. Toxicon. 2012, vol. 59, pp. 464-471.
European Search Report dated Apr. 19, 2013 issued in EP 12172010.
European Search Report from EP Application EP12306647.4, dated May 22, 2013.
Krstenansky et al. 'Importance of the 10-13 Region of Glucagon for its Receptors Interaction and Activation of Adenylate Cyclase'. Biochemistry. 1986, vol. 25, No. 13, pp. 3833-3839.
International Preliminary Report on Patentability for Application No. PCT/EP2013/70882, dated Dec. 1, 2014 (7 pages).
Day, J.W. et al., A new glucagon and GLP-1 co-agonist eliminates obesity in rodents, Nature Chemical Biology, (Oct. 2009), vol. 5, No. 10, pp. 749-757.
Hjorth, S.A. et al., Glucagon and Glucagon-like Peptide 1: Selective Receptor Recognition via Distinct Peptide Epitopes, The Journal of Biological Chemistry, (Dec. 2, 1994), vol. 269, No. 48, pp. 30121-30124.
Ficht, S. et al., Solid-Phase Synthesis of Peptide and Glycopeptide Thioesters through Side-Chain-Anchoring Strategies, Chem. Eur. J., (2008), vol. 14, pp. 3620-3629.
Chae, S. et al, The fatty acid conjugated exendin-4 analogs for type 2 anti-diabetic therapeutics, Journal of Controlled Release, (2010), vol. 144, pp. 10-16.
European Search Report dated Apr. 19, 2013 issued in EP 12 30 6232.
European Search Report dated Jul. 15, 2013 issued in EP 13 30 5222.
U.S. Appl. No. 14/569,326, filed Dec. 12, 2014, Haack et al.
Bhat et al. (Jun. 1, 2013) "A novel GIP-oxyntomodulin hybrid peptide acting through GIP, glucagon and GLP-1 receptors exhibits weight reducing and anti-diabetic properties," Biochem. Pharmacol. 85:1655-1662.
Bhat et al. (Mar. 17, 2013) "A DPP-IV-resistant triple-acting agonist of GIP, GLP-1 and glucagon receptors with potent glucose-lowering and insulinotropic actions in high-fat-fed mice," Diabetologia. 56:1417-1424.
Hoist (2007) "The physiology of glucagon-like peptide 1," Physiol. Rev. 87(4):1409-1439.
Kosinski et al. (Mar. 16, 2012) "The glucagon receptor is involved in mediating the body weight-lowering effects of oxyntomodulin," Obesity (Silver Spring). 20:1566-1571.
Meier (Sep. 4, 2012) "GLP-1 receptor agonists for individualized treatment of type 2 diabetes mellitus," Nat. Rev. Endocrinol. 8:728-742.
Pedersen et al. (2006) "N- and C-terminal hydrophobic patches are involved in fibrillation of glucagon," Biochemistry. 45:14503-14512.
Pocai (2009) "Glucagon-like peptide 1/glucagon receptor dual agonism reverses obesity in mice," Diabetes. 58 (10):2258-2266.
International Search Report with Written Opinion corresponding to International Patent Application No. PCT/EP2013/070882, mailed Dec. 5, 2013.

* cited by examiner

- Vehicle-Control
- SEQ ID NO: 97, 0.002 mg/kg, s.c.
- SEQ ID NO: 97, 0.02 mg/kg, s.c.

- Vehicle-Control
- SEQ ID NO: 97, 0.002 mg/kg, s.c.
- SEQ ID NO: 97, 0.02 mg/kg, s.c.

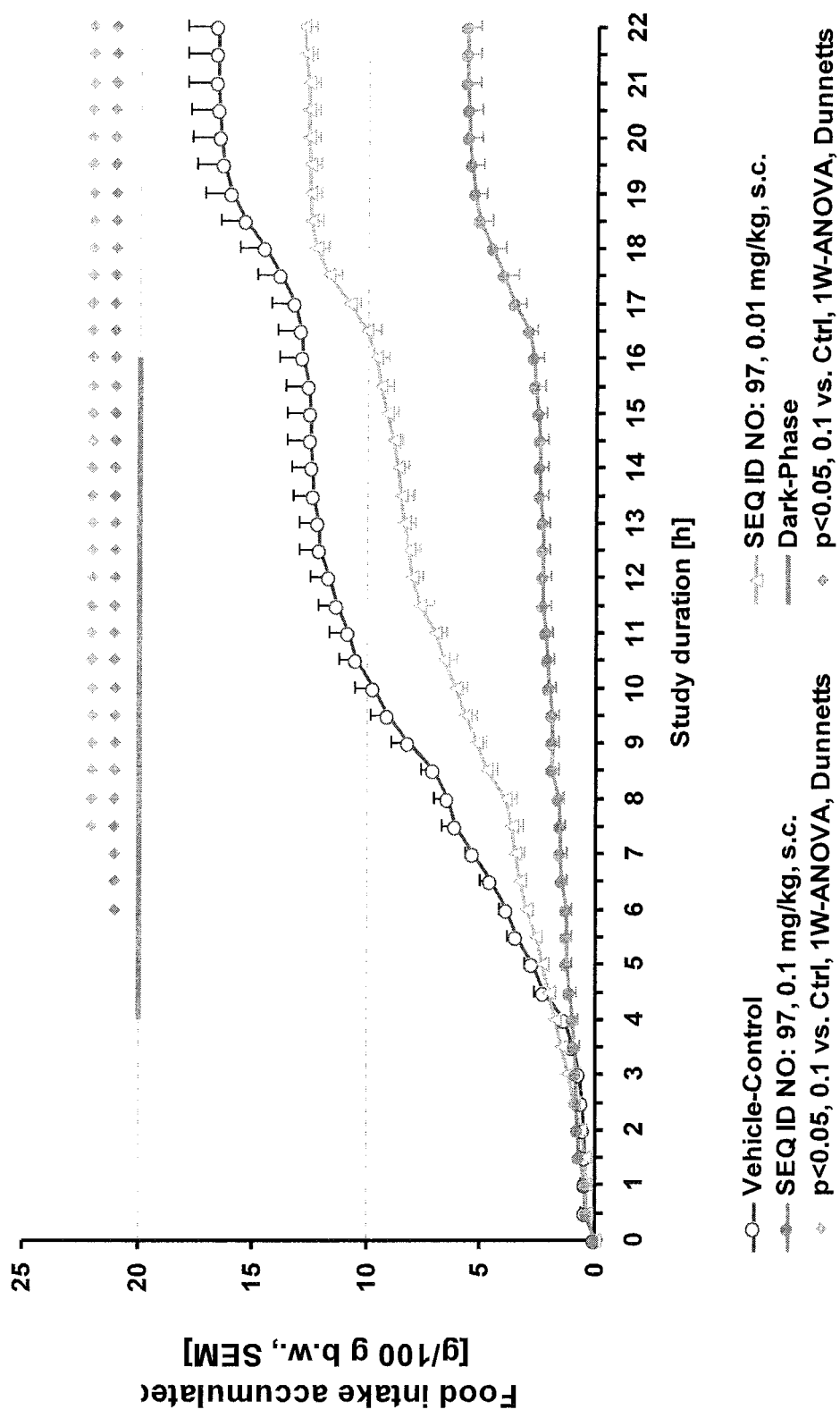

SEQUENCE LISTING

<160> NUMBER OF SEQ ID NOS: 229

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Ser is modified with an NH2 group

<400> SEQUENCE: 1

His Gly Glu Gly Thr Phe Thr Ser Asp Leu Ser Lys Gln Met Glu Glu

```
                    1               5                  10                 15
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 29
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Arg is modified with an NH2 group

<400> SEQUENCE: 2

His Ala Glu Gly Thr Phe Thr Ser Asp Val Ser Ser Tyr Leu Glu Gly
1               5                   10                  15

Gln Ala Ala Lys Glu Ile Ala Trp Leu Val Lys Gly Arg
            20                  25

<210> SEQ ID NO 3
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Thr is modified with an OH group

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Val Gln Trp Leu Met Asn Thr
            20                  25

<210> SEQ ID NO 4
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 4

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Ser
        35

<210> SEQ ID NO 5
<211> LENGTH: 39
<212> TYPE: PRT
```

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 5

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 6
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Lys is modified with an NH2 group

<400> SEQUENCE: 6

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser Lys
        35                  40

<210> SEQ ID NO 7
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalised at the amino side chain
```

```
            group as Lys(4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 7

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 8

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4(4-dodecyloxy-benzoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 9

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 10
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-n-propyl group

<400> SEQUENCE: 10

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 11

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
```

```
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 12

His Xaa Gln Gly Thr Phe Thr Ser Asp Leu Ser Lys Gln Lys Glu Ser
1               5                   10                  15

Xaa Ala Ala Xaa Leu Phe Ile Glu Trp Leu Lys Ala Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 13

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
```

```
        group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 14

His Xaa Gln Gly Thr Phe Thr Ser Asp Leu Ser Lys Gln Lys Glu Ser
1               5                   10                  15

Xaa Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
        group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 15

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
        group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 16
```

His Xaa Gln Gly Thr Phe Thr Ser Asp Leu Ser Lys Gln Lys Glu Glu
1               5                   10                  15

Glu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 17

His Xaa Gln Gly Thr Phe Thr Ser Asp Leu Ser Lys Gln Lys Glu Glu
1               5                   10                  15

Glu Ala Ala Lys Asp Phe Ile Glu Trp Leu Lys Ala Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 18

His Xaa Gln Gly Thr Phe Thr Ser Asp Leu Ser Lys Gln Lys Glu Glu
1               5                   10                  15

Glu Ala Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 19
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 19

His Xaa Gln Gly Thr Phe Thr Ser Asp Leu Ser Lys Gln Lys Glu Glu
1               5                   10                  15

Glu Ala Ala Lys Leu Phe Ile Glu Trp Leu Lys Ala Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 20

His Xaa Gln Gly Thr Phe Thr Ser Asp Leu Ser Lys Gln Lys Glu Ser
1               5                   10                  15

Glu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

-continued

<223> OTHER INFORMATION: Ser is modified with an NH2 group

<400> SEQUENCE: 21

His Xaa Gln Gly Thr Phe Thr Ser Asp Leu Ser Lys Gln Lys Glu Ser
1               5                   10                  15

Glu Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 22

His Xaa Gln Gly Thr Phe Thr Ser Asp Leu Ser Lys Gln Lys Asp Glu
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 23

His Xaa Gln Gly Thr Phe Thr Ser Asp Leu Ser Lys Gln Lys Glu Glu
1               5                   10                  15

Lys Lys Ala Lys Leu Phe Ile Glu Trp Leu Lys Ala Gly Gly Pro Ser
            20                  25                  30

Ser Gly Ala Pro Pro Pro Ser
        35

<210> SEQ ID NO 24
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 24

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 25

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
```

-continued

<223> OTHER INFORMATION: Ser is modified with an NH2 group

<400> SEQUENCE: 26

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid side
      chain group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 27

His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 28

His Xaa Gln Gly Thr Phe Thr Ser Asp Leu Ser Lys Gln Lys Glu Ser
1               5                   10                  15

Lys Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 29
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 29

His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 30

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

```
<223> OTHER INFORMATION: Ser is modified with an NH2 group

<400> SEQUENCE: 31

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 32

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 33

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 34
<211> LENGTH: 39
```

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 34

His Xaa Gln Gly Thr Phe Thr Ser Asp Leu Ser Lys Gln Lys Asp Glu
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 35

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

<223> OTHER INFORMATION: Ser is modified with an NH2 group

<400> SEQUENCE: 36

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 37

His Xaa Gln Gly Thr Phe Thr Ser Asp Leu Ser Lys Gln Lys Glu Ser
1               5                   10                  15

Gln Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 38

His Xaa Gln Gly Thr Phe Thr Ser Asp Leu Ser Lys Gln Lys Glu Ser
1               5                   10                  15

Gln Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 39
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 39

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 40

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
```

```
<223> OTHER INFORMATION: Ser is modified with an NH2 group

<400> SEQUENCE: 41

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 42

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino acid chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 43

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 44
<211> LENGTH: 39
```

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 44

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 45

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      as Lys((S)-4-carboxy-4-hexadecanoylamino-butyryl)
<220> FEATURE:
<221> NAME/KEY: MOD_RES
<222> LOCATION: (20)..(20)
```

```
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 46

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Ala Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys ((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 47

His Xaa Gln Gly Thr Phe Thr Ser Asp Leu Ser Lys Gln Lys Glu Ser
1               5                   10                  15

Arg Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 48

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35
```

```
<210> SEQ ID NO 49
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 49

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 50

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
```

-continued

```
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 51

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 52
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-octadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 52

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 53

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30
```

Ser Gly Ala Pro Pro Pro Ser
        35

<210> SEQ ID NO 54
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(3-(3-octadecanoylamino-propionylamino)-propionyl)
<220> FEATURE:
<221> NAME/KEY: MOD_RES
<222> LOCATION: (39)..(39)
<223> OTHER INFORMATION: Ser is modified with an NH2 group

<400> SEQUENCE: 54

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 55
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((Z)-octadec-9-enoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 55

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES

```
<222> LOCATION: (14)..(14)
<223> OTHER INFORMATION: Lys is functionalized at the amino side chain
      group as Lys(4-((Z)-octadec-9-enoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 56

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(3-[(R)-2,5,7,8-tetramethyl-2-
      ((4R,8R)-4,8,12-trimethyl-tridecyl)-chroman-6-yloxycarbonyl]-
      propionylamino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 57

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 58
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-(3-[(R)-2,5,7,8-tetramethyl-2-((4R,8R)-4,8,12-
      trimethyl-tridecyl)-chroman-6-yloxycarbonyl]-propionylamino}-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 58

His Xaa Gln Gly Thr Phe Thr Ser Asp Leu Ser Lys Gln Lys Glu Ser
1               5                   10                  15
```

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 59

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-docosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 60

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 61
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES

```
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino acid side
      chain group as Lys((S)-4-carboxy-4-((Z)-nonadec-10-enoylamino)-
      butyryl)
<220> FEATURE:
<221> NAME/KEY: MOD_RES
<222> LOCATION: (39)..(39)
<223> OTHER INFORMATION: Ser is modfied with an NH2 group

<400> SEQUENCE: 61

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 62
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(4-decyloxy-benzoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 62

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[(4'-octyloxy-biphenyl-4-carbonyl)-
      amino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 63
```

```
His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 64
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(12-phenyl-dodecanoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 64

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 65
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 65

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
            35

<210> SEQ ID NO 66
<211> LENGTH: 39
<212> TYPE: PRT
<213> ORGANISM: Artificial Sequence
<220> FEATURE:
<223> OTHER INFORMATION: Exendin-4-analogue
```

```
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 66

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 67
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 67

His Xaa Gln Gly Thr Phe Thr Ser Asp Leu Ser Lys Gln Lys Asp Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

<223> OTHER INFORMATION: Ser is modified with an NH2 group

<400> SEQUENCE: 68

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 69

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 70

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 71
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Orn amino acid
<220> FEATURE:
<221> NAME/KEY: MOD_RES
<222> LOCATION: (14)..(14)
<223> OTHER INFORMATION: Orn is functionalized at the amino side chain
      group as Orn(S)-4-carboxy-4-hexadecanoylamino-butyryl
<220> FEATURE:
<221> NAME/KEY: MOD_RES
<222> LOCATION: (39)..(39)
<223> OTHER INFORMATION: Ser is modified with an NH2 group

<400> SEQUENCE: 71

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an alpha,gamma-diaminobutyricacid (Dab)
      amino acid
<220> FEATURE:
<221> NAME/KEY: MOD_RES
<222> LOCATION: (14)..(14)
<223> OTHER INFORMATION: Dab is functionalized at the amino side chain
      group as Dab(S)-4-carboxy-4-hexadecanoylamino-butyryl
<220> FEATURE:
<221> NAME/KEY: MOD_RES
<222> LOCATION: (39)..(39)
<223> OTHER INFORMATION: Ser is modified with an NH2 group

<400> SEQUENCE: 72

His Xaa Gln Gly Thr Phe Thr Ser Asp Leu Ser Lys Gln Xaa Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 73
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

```
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 73

His Xaa His Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 74

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 75
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 75
```

```
His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35
```

<210> SEQ ID NO 76
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 76

```
His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Ala Gly Gly Pro Ser
            20                  25                  30

Ser Gly Ala Pro Pro Pro Ser
        35
```

<210> SEQ ID NO 77
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 77

```
His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35
```

<210> SEQ ID NO 78

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 78

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
            35

<210> SEQ ID NO 79
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 79

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Xaa Gly Gly Pro Ser
            20                  25                  30

Ser Gly Ala Pro Pro Pro Ser
            35

<210> SEQ ID NO 80
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

-continued

```
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 80

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asp Gly Gly Pro Ser
            20                  25                  30

Ser Gly Ala Pro Pro Pro Ser
        35

<210> SEQ ID NO 81
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 81

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asp Gly Gly Pro Ser
            20                  25                  30

Ser Gly Ala Pro Pro Pro Ser
        35

<210> SEQ ID NO 82
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 82

His Xaa Gln Gly Thr Phe Thr Ser Asp Leu Ser Lys Gln Lys Glu Ser
1               5                   10                  15
```

Arg Arg Ala Gln Asp Phe Ile Glu Trp Leu Lys Glu Gly Gly Pro Ser
            20                  25                  30

Ser Gly Arg Pro Pro Ser
        35

<210> SEQ ID NO 83
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 83

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Glu Gly Gly Pro Ser
            20                  25                  30

Ser Gly Arg Pro Pro Ser
        35

<210> SEQ ID NO 84
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 84

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Lys Gly Gly Pro Ser
            20                  25                  30

Ser Gly Ala Pro Pro Ser
        35

<210> SEQ ID NO 85
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)

```
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 85

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 86
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 86

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Asn Thr Gly Pro Ser
            20                  25                  30

Ser Gly Ala Pro Pro Pro Ser
        35

<210> SEQ ID NO 87
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified withn an NH2 group

<400> SEQUENCE: 87

His Xaa Gln Gly Thr Phe Thr Ser Asp Leu Ser Lys Gln Lys Asp Glu
1               5                   10                  15
```

Arg Arg Ala Lys Asp Phe Ile Glu Trp Leu Lys Asn Gly Gly Pro Ser
            20                  25                  30

Ser Gly Ala Pro Pro Ser
        35

<210> SEQ ID NO 88
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 88

His Xaa Gln Gly Thr Phe Thr Ser Asp Leu Ser Lys Gln Lys Glu Lys
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 89
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(3-[(R)-2,5,7,8-tetramethyl-2-
      ((4R,8R)-4,8,12-trimethyl-tridecyl)-chroman-6-yloxycarbonyl]-
      propionylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 89

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Ser
        35

<210> SEQ ID NO 90
<211> LENGTH: 39
<212> TYPE: PRT
<213> ORGANISM: Artificial Sequence
<220> FEATURE:
<223> OTHER INFORMATION: Exendin-4-analogue
<220> FEATURE:

```
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-tetradecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 90

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 91
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-(11-benzyloxycarbonyl-undecanoylamino)-4-
      carboxy-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 91

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 92
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 92
```

```
His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Thr Gly Pro Ser
            20                  25                  30

Ser Gly Ala Pro Pro Pro Ser
            35

<210> SEQ ID NO 93
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 93

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Ala Gly Pro Ser
            20                  25                  30

Ser Gly Ala Pro Pro Pro Ser
            35

<210> SEQ ID NO 94
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 94

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Xaa Gly Pro Ser
            20                  25                  30

Ser Gly Ala Pro Pro Pro Ser
            35

<210> SEQ ID NO 95
<211> LENGTH: 39
```

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 95

His Xaa Gln Gly Thr Phe Thr Ser Asp Leu Ser Lys Gln Lys Glu Ser
1               5                   10                  15
Arg Arg Ala Gln Asp Phe Ile Glu Trp Leu Lys Asn Ala Gly Pro Ser
            20                  25                  30
Ser Gly Ala Pro Pro Pro Ser
        35

<210> SEQ ID NO 96
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 96

His Xaa Gln Gly Thr Phe Thr Ser Asp Leu Ser Lys Gln Lys Glu Ser
1               5                   10                  15
Arg Arg Ala Gln Asp Phe Ile Glu Trp Leu Lys Asn Thr Gly Pro Ser
            20                  25                  30
Ser Gly Ala Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

-continued

<223> OTHER INFORMATION: Ser is modified with an NH2 group

<400> SEQUENCE: 97

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 98
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butytyl)
<220> FEATURE:
<221> NAME/KEY: MOD_RES
<222> LOCATION: (39)..(39)
<223> OTHER INFORMATION: Ser is modified with an NH-pyrrolidin group

<400> SEQUENCE: 98

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 99
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-benzyl group

<400> SEQUENCE: 99

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 100
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-tert.butyl group

<400> SEQUENCE: 100

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 101
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized ath the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an N-diethyl group

<400> SEQUENCE: 101

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 102
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

```
<223> OTHER INFORMATION: Ser is modified with an N-morpholin group

<400> SEQUENCE: 102

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 103
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-CH2-CF3 group

<400> SEQUENCE: 103

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 104
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)4-CH2-
      CH2-COOH group

<400> SEQUENCE: 104

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 105
```

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)24-CH2-
      CH2-COOH group

<400> SEQUENCE: 105

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 106
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)15-CH3 group

<400> SEQUENCE: 106

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 107
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
```

```
<221> NAME/KEY: MOD_RES
<222> LOCATION: (39)..(39)
<223> OTHER INFORMATION: Ser is modified with an NH-(CH2)12-OH group

<400> SEQUENCE: 107

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 108
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)14-CH3 group

<400> SEQUENCE: 108

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 109
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)17-CH3 group

<400> SEQUENCE: 109

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35
```

```
<210> SEQ ID NO 110
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2)13-CH3 group

<400> SEQUENCE: 110

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 111
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (40)..(40)
<223> OTHER INFORMATION: Ser is modified with an NH2 group

<400> SEQUENCE: 111

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 112
<211> LENGTH: 40
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
```

```
<221> NAME/KEY: MOD_RES
<222> LOCATION: (40)..(40)
<223> OTHER INFORMATION: Ser is modified with an NH2 group

<400> SEQUENCE: 112

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser Lys
        35                  40

<210> SEQ ID NO 113
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 113

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35

<210> SEQ ID NO 114
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 114

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Lys
        35
```

```
<210> SEQ ID NO 115
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 115

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 116
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: SITE
<222> LOCATION: (39)..(39)
<223> OTHER INFORMATION: Ser is modified with an NH2 group

<400> SEQUENCE: 116

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl-)
<220> FEATURE:
```

```
<221> NAME/KEY: MOD_RES
<222> LOCATION: (39)..(39)
<223> OTHER INFORMATION: Ser is modified with an NH2 group

<400> SEQUENCE: 117

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 118
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 118

His Xaa Gln Gly Thr Phe Thr Ser Asp Leu Ser Lys Gln Lys Asp Ser
1               5                   10                  15

Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 119
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 119

His Xaa Gln Gly Thr Phe Thr Ser Asp Leu Ser Lys Gln Lys Glu Ser
1               5                   10                  15
```

```
Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 120
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 120

His Xaa Gln Gly Thr Phe Thr Ser Asp Leu Ser Lys Gln Lys Glu Ser
1               5                   10                  15

Arg Arg Ala Xaa Asp Phe Ile Glu Trp Leu Lys Asn Gly Gly Pro Ser
            20                  25                  30

Ser Gly Ala Pro Pro Pro Ser
        35

<210> SEQ ID NO 121
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 121

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Asn Gly Gly Pro Ser
            20                  25                  30

Ser Gly Ala Pro Pro Pro Ser
        35
```

```
<210> SEQ ID NO 122
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(hexadecanoyl)
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 122

His Xaa Gln Gly Thr Phe Thr Ser Asp Leu Ser Lys Gln Lys Glu Ser
1               5                   10                  15

Arg Ala Ala Xaa Leu Phe Ile Glu Trp Leu Lys Asn Gly Gly Pro Ser
            20                  25                  30

Ser Gly Ala Pro Pro Pro Ser
        35

<210> SEQ ID NO 123
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 123

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Arg Gly Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
```

```
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 124

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Arg Ala Gly Pro Ser
            20                  25                  30

Ser Gly Ala Pro Pro Pro Ser
            35

<210> SEQ ID NO 125
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 125

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
            35

<210> SEQ ID NO 126
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 126

His Xaa Gln Gly Thr Phe Thr Ser Asp Leu Ser Lys Gln Lys Glu Ser
1               5                   10                  15
```

```
Arg Arg Ala Gln Asp Phe Ile Glu Trp Leu Lys Arg Xaa Gly Pro Ser
            20                  25                  30

Ser Gly Ala Pro Pro Pro Ser
            35

<210> SEQ ID NO 127
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 127

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Arg Gly Gly Pro Ser
            20                  25                  30

Ser Gly Ala Pro Pro Pro Ser
            35

<210> SEQ ID NO 128
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 128

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ser Gly Gly Pro Ser
            20                  25                  30

Ser Gly Ala Pro Pro Pro Ser
            35

<210> SEQ ID NO 129
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
```

```
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 129

His Xaa Gln Gly Thr Phe Thr Ser Asp Leu Ser Lys Gln Lys Glu Ser
 1               5                  10                  15

Arg Arg Ala Gln Asp Phe Ile Glu Trp Leu Lys Ser Gly Gly Pro Ser
             20                  25                  30

Ser Gly Ala Pro Pro Pro Ser
         35

<210> SEQ ID NO 130
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 130

His Xaa Gln Gly Thr Phe Thr Ser Asp Leu Ser Lys Gln Lys Glu Ser
 1               5                  10                  15

Xaa Ala Ala Gln Leu Phe Ile Glu Trp Leu Lys Ala Gly Gly Pro Ser
             20                  25                  30

Ser Gly Ala Pro Pro Pro Ser
         35

<210> SEQ ID NO 131
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(4-octadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
```

```
<221> NAME/KEY: MOD_RES
<222> LOCATION: (39)..(39)
<223> OTHER INFORMATION: Ser is modified with an NH2 group

<400> SEQUENCE: 131

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
            35

<210> SEQ ID NO 132
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (17)..(17)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 132

His Xaa Gln Gly Thr Phe Thr Ser Asp Leu Ser Lys Gln Lys Glu Ser
1               5                   10                  15

Xaa Ala Ala Gln Leu Phe Ile Glu Trp Leu Lys Ala Gly Gly Pro Ser
            20                  25                  30

Ser Gly Ala Pro Pro Pro Ser
            35

<210> SEQ ID NO 133
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 133

His Xaa Gln Gly Thr Phe Thr Ser Asp Leu Ser Lys Gln Lys Asp Glu
1               5                   10                  15
```

-continued

Lys Ala Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 134
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 134

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 135
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 135

His Xaa Gln Gly Thr Phe Thr Ser Asp Leu Ser Lys Gln Lys Glu Ser
1               5                   10                  15

Lys Ala Ala Gln Glu Phe Ile Glu Trp Leu Lys Ala Gly Gly Pro Ser
            20                  25                  30

Ser Gly Ala Pro Pro Pro Ser
        35

<210> SEQ ID NO 136
<211> LENGTH: 39
<212> TYPE: PRT
<213> ORGANISM: Artificial Sequence
<220> FEATURE:
<223> OTHER INFORMATION: Exendin-4-analogue

```
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(15-carboxy-pentadecanoylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 136

His Xaa Gln Gly Thr Phe Thr Ser Asp Leu Ser Lys Gln Lys Glu Ser
1               5                   10                  15

Lys Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 137
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 137

His Xaa His Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 138
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
```

```
<222> LOCATION: (39)..(39)
<223> OTHER INFORMATION: Ser is modified with an NH2 group

<400> SEQUENCE: 138

His Xaa His Gly Thr Phe Thr Ser Asp Leu Ser Lys Gln Lys Asp Ser
1               5                   10                  15

Lys Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 139
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 139

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 140
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 140

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35
```

```
<210> SEQ ID NO 141
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys(6-[(4,4-diphenyl-cyclohexyloxy)-hydroxy-
      phosphoryloxy]-hexanoyl)
<220> FEATURE:
<221> NAME/KEY: MOD_RES
<222> LOCATION: (39)..(39)
<223> OTHER INFORMATION: Ser is modified with an NH2 group

<400> SEQUENCE: 141

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 142
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-icosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 142

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 143
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
```

```
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 143

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Ala Xaa Gly Pro Ser
            20                  25                  30

Ser Gly Ala Pro Pro Pro Ser
        35

<210> SEQ ID NO 144
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (19)..(19)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 144

His Xaa Gln Gly Thr Phe Thr Ser Asp Leu Ser Lys Gln Lys Asp Ser
1               5                   10                  15

Lys Ala Xaa Gln Asp Phe Ile Glu Trp Leu Lys Ala Gly Gly Pro Ser
            20                  25                  30

Ser Gly Ala Pro Pro Pro Ser
        35

<210> SEQ ID NO 145
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 145

His Xaa Gln Gly Thr Phe Thr Ser Asp Leu Ser Lys Gln Lys Asp Ser
```

```
                1               5                  10                 15
Lys Ala Ser Gln Asp Phe Ile Glu Trp Leu Lys Ala Gly Gly Pro Ser
                20                 25                 30

Ser Gly Ala Pro Pro Pro Ser
            35

<210> SEQ ID NO 146
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 146

His Xaa Gln Gly Thr Phe Thr Ser Asp Leu Ser Lys Gln Lys Asp Ser
1               5                  10                 15

Lys Ala Leu Gln Asp Phe Ile Glu Trp Leu Lys Ala Gly Gly Pro Ser
                20                 25                 30

Ser Gly Ala Pro Pro Pro Ser
            35

<210> SEQ ID NO 147
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 147

His Xaa Gln Gly Thr Phe Thr Ser Asp Leu Ser Lys Gln Lys Asp Ser
1               5                  10                 15

Lys Ala Ala Gln Asp Phe Ile Glu Trp Lys Lys Ala Gly Gly Pro Ser
                20                 25                 30

Ser Gly Ala Pro Pro Pro Ser
            35

<210> SEQ ID NO 148
<211> LENGTH: 39
<212> TYPE: PRT
<213> ORGANISM: Artificial Sequence
<220> FEATURE:
<223> OTHER INFORMATION: Exendin-4-analogue
<220> FEATURE:
```

```
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 148

His Xaa Gln Gly Thr Phe Thr Ser Asp Leu Ser Lys Gln Lys Asp Ser
 1               5                  10                  15

Lys Ala Ala Gln Leu Phe Ile Glu Trp Leu Lys Ala Xaa Gly Pro Ser
             20                  25                  30

Ser Gly Ala Pro Pro Pro Ser
         35

<210> SEQ ID NO 149
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 149

His Xaa Gln Gly Thr Phe Thr Ser Asp Leu Ser Lys Gln Lys Asp Ser
 1               5                  10                  15

Lys Ala Ala Gln Leu Phe Ile Glu Trp Leu Lys Ala Xaa Gly Pro Ser
             20                  25                  30

Ser Gly Ala Pro Pro Pro Ser
         35

<210> SEQ ID NO 150
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
```

```
<220> FEATURE:
<221> NAME/KEY: MOD_RES
<222> LOCATION: (39)..(39)
<223> OTHER INFORMATION: Ser is modified with an NH2 group

<400> SEQUENCE: 150

His Xaa Gln Gly Thr Phe Thr Ser Asp Leu Ser Lys Gln Lys Glu Ser
1               5                   10                  15

Leu Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 151
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 151

His Xaa Gln Gly Thr Phe Thr Ser Asp Leu Ser Lys Gln Lys Asp Glu
1               5                   10                  15

Gln Ala Ala Lys Asp Phe Ile Glu Trp Leu Lys Ala Gly Gly Pro Ser
            20                  25                  30

Ser Gly Ala Pro Pro Pro Ser
        35

<210> SEQ ID NO 152
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 152

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ala Gly Gly Pro Ser
            20                  25                  30

Ser Gly Ala Pro Pro Pro Ser
        35
```

```
<210> SEQ ID NO 153
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 153

His Xaa Gln Gly Thr Phe Thr Ser Asp Leu Ser Lys Gln Lys Asp Glu
1               5                   10                  15

Gln Ala Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 154
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 154

His Xaa Gln Gly Thr Phe Thr Ser Asp Leu Ser Lys Gln Lys Glu Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 155
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
```

```
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 155

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 156
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 156

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 157
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 157

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Ala Gly Gly Pro Ser
            20                  25                  30
```

Ser Gly Ala Pro Pro Pro Ser
        35

<210> SEQ ID NO 158
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 158

His Xaa Gln Gly Thr Phe Thr Ser Asp Leu Ser Lys Gln Lys Asp Ser
1               5                   10                  15

Gln Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 159
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 159

His Xaa Gln Gly Thr Phe Thr Ser Asp Leu Ser Lys Gln Lys Asp Ser
1               5                   10                  15

Gln Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 160
<211> LENGTH: 39
<212> TYPE: PRT

```
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((9Z,12Z)-octadeca-9,12-
      dienoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 160

His Xaa Gln Gly Thr Phe Thr Ser Asp Leu Ser Lys Gln Lys Glu Ser
1               5                   10                  15
Arg Ala Ala Gln Asp Phe Ile Glu Trp Leu Lys Ala Gly Gly Pro Ser
            20                  25                  30
Ser Gly Ala Pro Pro Pro Ser
        35

<210> SEQ ID NO 161
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is a D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 161

His Xaa Gln Gly Thr Phe Thr Ser Asp Leu Ser Lys Gln Lys Asp Ser
1               5                   10                  15
Arg Arg Ala Gln Asp Phe Ile Glu Trp Leu Lys Ala Xaa Gly Pro Ser
            20                  25                  30
Ser Gly Ala Pro Pro Pro Ser
        35

<210> SEQ ID NO 162
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
```

```
                 group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 162

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 163
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 163

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 164
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 164

His Xaa Gln Gly Thr Phe Thr Ser Asp Leu Ser Lys Gln Lys Asp Ser
1               5                   10                  15

Lys Ala Ala Gln Asp Phe Ile Glu Trp Leu Lys Xaa Gly Gly Pro Ser
```

Ser Gly Ala Pro Pro Pro Ser
        35

<210> SEQ ID NO 165
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 165

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Glu Gly Gly Pro Ser
            20                  25                  30

Ser Gly Lys Pro Pro Pro Ser
        35

<210> SEQ ID NO 166
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 166

His Xaa Gln Gly Thr Phe Thr Ser Asp Leu Ser Lys Gln Lys Asp Ser
1               5                   10                  15

Gln Ala Ala Gln Asp Phe Ile Glu Trp Leu Lys Asn Thr Gly Pro Ser
            20                  25                  30

Ser Gly Ala Pro Pro Pro Ser
        35

<210> SEQ ID NO 167
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser

```
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-(3-[3-((2S,3R,4S,5R)-5-carboxy-2,3,
      4,5-tetrahydroxy-pentanoylamino-)-propionylamino]-propionylamino)-
      butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 167

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 168
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((9Z,12Z)-octadeca-9,12-
      dienoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 168

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 169
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[6-((2S,3R,4S,5R)-5-carboxy-2,3,4,5-
      tetrahydroxy-pentanoylamino)-hexanoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 169
```

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 170
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((2S,3R,4S,5R)-5-carboxy-2,3,4,5-
      tetrahydroxy-pentanoylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 170

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 171
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-[11-((2S,3R,4R,5R)-2,3,4,5,6-
      pentahydroxy-hexylcarbamoyl)-undecanoylamino]-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 171

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 172
<211> LENGTH: 39
<212> TYPE: PRT
<213> ORGANISM: Artificial Sequence

```
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 172

His Xaa Gln Gly Thr Phe Thr Ser Asp Leu Ser Lys Gln Lys Glu Ser
1               5                  10                  15

Arg Arg Ala Gln Asp Phe Ile Glu Trp Leu Lys Arg Gly Gly Pro Ser
            20                  25                  30

Ser Gly Glu Pro Pro Pro Ser
        35

<210> SEQ ID NO 173
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 173

His Xaa Gln Gly Thr Phe Thr Ser Asp Leu Ser Lys Gln Lys Asp Ser
1               5                  10                  15

Lys Ala Ala Gln Asp Phe Ile Glu Trp Leu Lys Ser Gly Gly Pro Ser
            20                  25                  30

Ser Gly Ala Pro Pro Pro Ser
        35

<210> SEQ ID NO 174
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group
```

<400> SEQUENCE: 174

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
        35

<210> SEQ ID NO 175
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 175

His Xaa Gln Gly Thr Phe Thr Ser Asp Leu Ser Lys Gln Lys Asp Glu
1               5                   10                  15

Gln Arg Ala Lys Asp Phe Ile Glu Trp Leu Lys Ser Gly Gly Pro Ser
            20                  25                  30

Ser Gly Ala Pro Pro Pro Ser
        35

<210> SEQ ID NO 176
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 176

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
        35

<210> SEQ ID NO 177
<211> LENGTH: 39
<212> TYPE: PRT
<213> ORGANISM: Artificial Sequence

```
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)24-CH2-
      CH2-COOH group

<400> SEQUENCE: 177

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 178
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH-(CH2-CH2-O)4-CH2-
      CH2-COOH group

<400> SEQUENCE: 178

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 179
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (3)..(3)
<223> OTHER INFORMATION: Gln is an alpha-N-MeGln
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
```

<223> OTHER INFORMATION: Ser is modified with an NH2 group

<400> SEQUENCE: 179

His Ser Gln Gly Thr Phe Thr Ser Asp Leu Ser Lys Gln Lys Glu Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 180
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (3)..(3)
<223> OTHER INFORMATION: Gln is an alpha-N-MeGln
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 180

His Ser Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 181
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 181

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 182
<211> LENGTH: 39

```
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 182

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 183

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 184
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 184

His Xaa Gln Gly Thr Phe Thr Ser Asp Leu Ser Lys Gln Met Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 185
```

```
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 185

His Xaa Gln Gly Thr Phe Thr Ser Asp Leu Ser Lys Gln Met Asp Ser
 1               5                  10                  15

Arg Arg Ala Gln Asp Phe Ile Glu Trp Leu Lys Arg Gly Gly Pro Ser
            20                  25                  30

Ser Gly Ala Pro Pro Pro Ser
        35

<210> SEQ ID NO 186
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 186

His Xaa Gln Gly Thr Phe Thr Ser Asp Leu Ser Lys Gln Met Asp Ser
 1               5                  10                  15

Arg Arg Ala Gln Asp Phe Ile Glu Trp Leu Lys Lys Gly Gly Pro Ser
            20                  25                  30

Ser Gly Ala Pro Pro Pro Ser
        35

<210> SEQ ID NO 187
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (28)..(28)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 187

His Xaa Gln Gly Thr Phe Thr Ser Asp Leu Ser Lys Gln Met Asp Ser
 1               5                  10                  15

Arg Arg Ala Gln Asp Phe Ile Glu Trp Leu Lys Xaa Gly Gly Pro Ser
            20                  25                  30
```

```
Ser Gly Ala Pro Pro Pro Ser
        35

<210> SEQ ID NO 188
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 188

His Xaa Gln Gly Thr Phe Thr Ser Asp Leu Ser Lys Gln Met Asp Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 189
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (39)..(39)
<223> OTHER INFORMATION: Ser is modified with an NH2 group

<400> SEQUENCE: 189

His Xaa Gln Gly Thr Phe Thr Ser Asp Leu Ser Lys Gln Met Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 190
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (20)..(20)
<223> OTHER INFORMATION: Xaa is an Aib amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 190

His Xaa Gln Gly Thr Phe Thr Ser Asp Leu Ser Lys Gln Met Glu Ser
```

```
                1               5                  10                 15
Arg Arg Ala Xaa Asp Phe Ile Glu Trp Leu Lys Ala Gly Gly Pro Ser
                20                 25                 30

Ser Gly Ala Pro Pro Ser
            35

<210> SEQ ID NO 191
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 191

His Xaa Gln Gly Thr Phe Thr Ser Asp Leu Ser Lys Gln Xaa Glu Ser
1               5                  10                 15

Gln Ala Ala Gln Asp Phe Ile Glu Trp Leu Lys Ala Gly Gly Pro Ser
                20                 25                 30

Ser Gly Ala Pro Pro Ser
            35

<210> SEQ ID NO 192
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is a Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 192

His Xaa Gln Gly Thr Phe Thr Ser Asp Leu Ser Lys Gln Xaa Asp Ser
1               5                  10                 15

Lys Ala Ala Gln Asp Phe Ile Glu Trp Leu Lys Ala Gly Gly Pro Ser
                20                 25                 30

Ser Gly Ala Pro Pro Ser
            35

<210> SEQ ID NO 193
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
```

```
<223> OTHER INFORMATION: Xaa is a D-Ser
<220> FEATURE:
<221> NAME/KEY: MOD_RES
<222> LOCATION: (14)..(14)
<223> OTHER INFORMATION: Xaa is an Nle amino acid
<220> FEATURE:
<221> NAME/KEY: MOD_RES
<222> LOCATION: (39)..(39)
<223> OTHER INFORMATION: Ser is modified with an NH2 group

<400> SEQUENCE: 193

His Xaa Gln Gly Thr Phe Thr Ser Asp Leu Ser Lys Gln Xaa Asp Ser
1               5                   10                  15

Gln Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 194
<211> LENGTH: 39
<212> TYPE: PRT
<213> ORGANISM: Artificial Sequence
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is an alpha-N-AcLys
<220> FEATURE:
<221> NAME/KEY: MOD_RES
<222> LOCATION: (39)..(39)
<223> OTHER INFORMATION: Ser is modified with an NH2 group

<400> SEQUENCE: 194

His Xaa Gln Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Pro Ser
        35

<210> SEQ ID NO 195
<211> LENGTH: 30
<212> TYPE: PRT
<213> ORGANISM: Artificial Sequence
<220> FEATURE:
<223> OTHER INFORMATION: Liraglutide
<220> FEATURE:
<221> NAME/KEY: MOD_RES
<222> LOCATION: (20)..(20)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (30)..(30)
<223> OTHER INFORMATION: Gly is modified with an OH group

<400> SEQUENCE: 195

His Ala Glu Gly Thr Phe Thr Ser Asp Val Ser Ser Tyr Leu Glu Gly
1               5                   10                  15

Gln Ala Ala Lys Glu Ile Ala Trp Leu Val Arg Gly Arg Gly
            20                  25                  30

<210> SEQ ID NO 196
<211> LENGTH: 39
```

```
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (20)..(20)
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 196

His Xaa Gln Gly Thr Phe Thr Ser Asp Leu Ser Lys Gln Lys Asp Ser
1               5                   10                  15

Lys Arg Ala Xaa Asp Phe Ile Glu Trp Leu Lys Ala Gly Gly Pro Ser
            20                  25                  30

Ser Gly Ala Pro Pro Pro Ser
        35

<210> SEQ ID NO 197
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 197

His Xaa Gln Gly Thr Phe Thr Ser Asp Leu Ser Lys Gln Lys Asp Glu
1               5                   10                  15

Gln Arg Ala Lys Leu Phe Ile Glu Trp Leu Lys Ala Gly Gly Pro Ser
            20                  25                  30

Ser Gly Ala Pro Pro Pro Ser
        35

<210> SEQ ID NO 198
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
```

-continued

```
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 198

His Xaa Gln Gly Thr Phe Thr Ser Asp Leu Ser Lys Gln Lys Asp Ser
1               5                   10                  15

Arg Arg Ala Gln Leu Phe Ile Glu Trp Leu Lys Ala Gly Gly Pro Ser
            20                  25                  30

Ser Gly Ala Pro Pro Pro Ser
        35

<210> SEQ ID NO 199
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 199

His Xaa Gln Gly Thr Phe Thr Ser Asp Leu Ser Lys Gln Lys Asp Glu
1               5                   10                  15

Gln Arg Ala Lys Asp Phe Ile Glu Trp Leu Lys Ala Xaa Gly Pro Ser
            20                  25                  30

Ser Gly Ala Pro Pro Pro Ser
        35

<210> SEQ ID NO 200
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 200
```

```
His Xaa Gln Gly Thr Phe Thr Ser Asp Leu Ser Lys Gln Lys Asp Glu
1               5                   10                  15

Gln Arg Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 201
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 201

His Xaa Gln Gly Thr Phe Thr Ser Asp Leu Ser Lys Gln Lys Asp Glu
1               5                   10                  15

Gln Ala Ala Lys Leu Phe Ile Glu Trp Leu Lys Ala Xaa Gly Pro Ser
            20                  25                  30

Ser Gly Ala Pro Pro Pro Ser
        35

<210> SEQ ID NO 202
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 202

His Xaa Gln Gly Thr Phe Thr Ser Asp Leu Ser Lys Gln Lys Glu Ser
1               5                   10                  15

Arg Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 203
<211> LENGTH: 39
```

```
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 203

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Gly Gly Pro Ser
            20                  25                  30

Ser Gly Ala Pro Pro Pro Ser
        35

<210> SEQ ID NO 204
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 204

His Xaa Gln Gly Thr Phe Thr Ser Asp Leu Ser Lys Gln Lys Glu Ser
1               5                   10                  15

Arg Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 205
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
```

```
        group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 205

His Xaa Gln Gly Thr Phe Thr Ser Asp Leu Ser Lys Gln Lys Glu Ser
1               5                   10                  15

Arg Arg Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 206
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
        group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 206

His Xaa Gln Gly Thr Phe Thr Ser Asp Leu Ser Lys Gln Lys Asp Glu
1               5                   10                  15

Gln Lys Ala Lys Leu Phe Ile Glu Trp Leu Lys Ser Gly Gly Pro Ser
            20                  25                  30

Ser Gly Ala Pro Pro Pro Ser
        35

<210> SEQ ID NO 207
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
        group as Lys((S)-4-carboxy-4-((S)-4-carboxy-4-hexadecanoylamino-
        butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 207

His Xaa Gln Gly Thr Phe Thr Ser Asp Leu Ser Lys Gln Lys Asp Glu
1               5                   10                  15
```

Gln Arg Ala Lys Glu Phe Ile Glu Trp Leu Lys Ser Gly Gly Pro Ser
            20                  25                  30

Ser Gly Ala Pro Pro Ser
        35

<210> SEQ ID NO 208
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 208

His Ser His Gly Thr Phe Thr Ser Asp Leu Ser Lys Gln Lys Glu Ser
1               5                   10                  15

Arg Arg Ala Gln Asp Phe Ile Glu Trp Leu Lys Ala Gly Gly Pro Ser
            20                  25                  30

Ser Gly Ala Pro Pro Ser
        35

<210> SEQ ID NO 209
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 209

His Xaa Gln Gly Thr Phe Thr Ser Asp Leu Ser Lys Gln Lys Asp Lys
1               5                   10                  15

Arg Arg Ala Gln Asp Phe Ile Glu Trp Leu Lys Ala Xaa Gly Pro Ser
            20                  25                  30

Ser Gly Ala Pro Pro Ser
        35

<210> SEQ ID NO 210
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)

```
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 210

His Xaa Gln Gly Thr Phe Thr Ser Asp Leu Ser Lys Gln Lys Asp Lys
1               5                   10                  15

Arg Arg Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 211
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 211

His Xaa Gln Gly Thr Phe Thr Ser Asp Leu Ser Lys Gln Lys Asp Lys
1               5                   10                  15

Arg Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 212
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-henicosanoylamino-butyryl)
<220> FEATURE:
<221> NAME/KEY: MOD_RES
```

```
<222> LOCATION: (29)..(29)
<223> OTHER INFORMATION: Xaa is D-Ala
<220> FEATURE:
<221> NAME/KEY: MOD_RES
<222> LOCATION: (39)..(39)
<223> OTHER INFORMATION: Ser is modified with an NH2 group

<400> SEQUENCE: 212

His Xaa Gln Gly Thr Phe Thr Ser Asp Leu Ser Lys Gln Lys Asp Lys
1               5                   10                  15

Arg Ala Ala Gln Leu Phe Ile Glu Trp Leu Lys Ala Xaa Gly Pro Ser
            20                  25                  30

Ser Gly Ala Pro Pro Pro Ser
        35

<210> SEQ ID NO 213
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 213

His Xaa Gln Gly Thr Phe Thr Ser Asp Leu Ser Lys Gln Lys Asp Glu
1               5                   10                  15

Glu Ala Ala Lys Leu Phe Ile Glu Trp Leu Lys Ala Gly Gly Pro Ser
            20                  25                  30

Ser Gly Ala Pro Pro Pro Ser
        35

<210> SEQ ID NO 214
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 214

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
```

<210> SEQ ID NO 215
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 215

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 216
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 216

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 217
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)

```
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 217

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 218
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 218

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 219
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 219

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
```

-continued

```
<210> SEQ ID NO 220
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 220

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 221
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 221

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 222
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
```

```
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 222

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 223
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 223

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 224
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 224

His Xaa Gln Gly Thr Phe Thr Ser Asp Leu Ser Lys Gln Leu Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 225
<211> LENGTH: 39
```

```
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (39)..(39)
<223> OTHER INFORMATION: Ser is modified with an NH2 group

<400> SEQUENCE: 225

His Xaa Gln Gly Thr Phe Thr Ser Asp Leu Ser Lys Gln Leu Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
            35

<210> SEQ ID NO 226
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 226

His Xaa Gln Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
            35

<210> SEQ ID NO 227
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group
```

```
<400> SEQUENCE: 227

His Xaa His Gly Thr Phe Thr Ser Asp Leu Ser Lys Gln Lys Asp Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 228
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 228

His Xaa Gln Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial
<220> FEATURE:
<223> OTHER INFORMATION: Exendin-4-analogue
<220> FEATURE:
<221> NAME/KEY: MOD_RES
<222> LOCATION: (2)..(2)
<223> OTHER INFORMATION: Xaa is Aib
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-((S)-4-carboxy-4-hexadecanoylamino-
      butyrylamino)-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 229

His Xaa His Gly Thr Phe Thr Ser Asp Leu Ser Lys Gln Lys Glu Glu
1               5                   10                  15

Glu Ala Ala Arg Leu Phe Ile Glu Trp Leu Lys Ala Gly Gly Pro Ser
            20                  25                  30

Ser Gly Ala Pro Pro Pro Ser
        35
```

EXENDIN-4 DERIVATIVES AS DUAL GLP1/GLUCAGON AGONISTS

FIELD OF THE INVENTION

The present invention relates to exendin-4 peptide analogues which—in contrast to the pure GLP-1 agonist exendin-4—activate both the GLP1 and the Glucagon receptor and their medical use, for example in the treatment of disorders of the metabolic syndrome, including diabetes and obesity, as well as for reduction of excess food intake.

BACKGROUND OF THE INVENTION

Exendin-4 is a 39 amino acid peptide which is produced by the salivary glands of the Gila monster (Heloderma suspectum) (Eng, J. et al., J. Biol. Chem., 267:7402-05, 1992). Exendin-4 is an activator of the glucagon-like peptide-1 (GLP-1) receptor, whereas it does not activate significantly the glucagon receptor.

Exendin-4 shares many of the glucoregulatory actions observed with GLP-1. Clinical and non-clinical studies have shown that exendin-4 has several beneficial antidiabetic properties including a glucose dependent enhancement in insulin synthesis and secretion, glucose dependent suppression of glucagon secretion, slowing down gastric emptying, reduction of food intake and body weight, and an increase in beta-cell mass and markers of beta cell function (Gentilella R et al., Diabetes Obes Metab., 11:544-56, 2009; Norris S L et al., Diabet Med., 26:837-46, 2009; Bunck M C et al., Diabetes Care., 34:2041-7, 2011).

These effects are beneficial not only for diabetics but also for patients suffering from obesity. Patients with obesity have a higher risk of getting diabetes, hypertension, hyperlipidemia, cardiovascular and musculoskeletal diseases.

Relative to GLP-1, exendin-4 is resistant to cleavage by dipeptidyl peptidase-4 (DPP4) resulting in a longer half-life and duration of action in vivo (Eng J., Diabetes, 45 (Suppl 2):152A (abstract 554), 1996).

Nevertheless, exendin-4 is chemically labile due to methionine oxidation in position 14 (Hargrove D M et al., Regul. Pept., 141: 113-9, 2007) as well as deamidation and isomerization of asparagine in position 28 (WO 2004/035623).

The amino acid sequence of exendin-4 is shown as SEQ ID NO: 1

HGEGTFTSDLSKQMEEEAVRLFIEWLKNGGPSSGAPPPS-NH₂

The amino acid sequence of GLP-1(7-36)-amide is shown as SEQ ID NO: 2

HAEGTFTSDVSSYLEGQAAKEFIAWLVKGR-NH₂

Liraglutide is a marketed chemically modified GLP-1 analog in which, among other modifications, a fatty acid is linked to a lysine in position 20 leading to a prolonged duration of action (Drucker D J et al., Nature Drug Disc. Rev. 9, 267-268, 2010; Buse, J. B. et al., Lancet, 374:39-47, 2009).

The amino acid sequence of Liraglutide is shown as SEQ ID NO: 195.

HAEGTFTSDVSSYLEGQAAK((S)-4-Carboxy-4-hexadecanoylamino-butyryl-)EFIAWLVRGRG-OH

Glucagon is a 29-amino acid peptide which is released into the bloodstream when circulating glucose is low. Glucagon's amino acid sequence is shown in SEQ ID NO: 3.

HSQGTFTSDYSKYLDSRRAQDFVQWLMNT-OH

During hypoglycemia, when blood glucose levels drop below normal, glucagon signals the liver to break down glycogen and release glucose, causing an increase of blood glucose levels to reach a normal level. Hypoglycemia is a common side effect of insulin treated patients with hyperglycemia (elevated blood glucose levels) due to diabetes. Thus, glucagon's most predominant role in glucose regulation is to counteract insulin action and maintain blood glucose levels.

Holst (Holst, J. J. Physiol. Rev. 2007, 87, 1409) and Meier (Meier, J. J. Nat. Rev. Endocrinol. 2012, 8, 728) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

Pocai et al. (Obesity 2012; 20: 1566-1571; Diabetes 2009, 58, 2258) and Day et al. (Nat Chem Biol 2009; 5: 749) describe that dual activation of the GLP-1 and glucagon receptors, e.g. by combining the actions of GLP-1 and glucagon in one molecule, leads to a therapeutic principle with anti-diabetic action and a pronounced weight lowering effect.

Peptides which bind and activate both the glucagon and the GLP-1 receptor (Hjort et al., Journal of Biological Chemistry, 269, 30121-30124, 1994; Day J W et al., Nature Chem Biol, 5: 749-757, 2009) and suppress body weight gain and reduce food intake are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416 and WO 2006/134340, the contents of which are herein incorporated by reference.

In addition, triple co-agonist peptides which not only activate the GLP-1 and the glucagon receptor but also the GIP receptor are described in WO 2012/088116 and by V A Gault et al. (Biochem Pharmacol, 85, 16655-16662, 2013; Diabetologia, 56, 1417-1424, 2013).

Bloom et al. (WO 2006/134340) disclose that peptides which bind and activate both the glucagon and the GLP-1 receptor can be constructed as hybrid molecules from glucagon and exendin-4, where the N-terminal part (e.g. residues 1-14 or 1-24) originates from glucagon and the C-terminal part (e.g. residues 15-39 or 25-39) originates from exendin-4.

D E Otzen et al. (Biochemistry, 45, 14503-14512, 2006) disclose that N- and C-terminal hydrophobic patches are involved in fibrillation of glucagon due to the hydrophobicity and/or high β-sheet propensity of the underlying residues.

Krstenansky et al. (Biochemistry, 25, 3833-3839, 1986) show the importance of the residues 10-13 of glucagon for its receptor interactions and activation of adenylate cyclase. In the exendin-4 derivatives described in this invention, several of the underlying residues are different from glucagon. In particular residues Tyr10 and Tyr13, which are known to contribute to the fibrillation of glucagon (D E Otzen, Biochemistry, 45, 14503-14512, 2006) are replaced by Leu in position 10 and Gln, a non-aromatic polar amino acid, in position 13, leading to exendin-4 derivatives with potentially improved biophysical properties.

Furthermore, compounds of this invention are exendin-4 derivatives with fatty acid acylated residues in position 14. This fatty acid functionalization in position 14 results in exendin-4 derivatives with high activity not only at the GLP-1 receptor but also at the glucagon receptor when compared to the corresponding non-acylated exendin-4 derivatives. In addition, this modification results in an improved pharmacokinetic profile.

Compounds of this invention are more resistant to cleavage by neutral endopeptidase (NEP) and dipeptidyl peptidase-4 (DPP4), resulting in a longer half-life and duration of action in vivo when compared with GLP-1 and glucagon. Furthermore, the compounds are stabilized versus other proteases, among those cathepsin D.

Compounds of this invention are preferably soluble not only at neutral pH, but also at pH 4.5. This property potentially allows co-formulation for a combination therapy with an insulin or insulin derivative and preferably with a basal insulin like insulin glargine/Lantus®.

BRIEF SUMMARY OF THE INVENTION

Provided herein are exendin-4 derivatives which potently activate the GLP1 and the glucagon receptor. In these exendin-4 derivatives—among other substitutions—methionine at position 14 is replaced by an amino acid carrying an —$NH_2$ group in the side chain, which is further substituted with an unpolar residue (e.g. a fatty acid optionally combined with a linker).

The invention provides a peptidic compound having the formula (I):

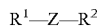 (I)

wherein Z is a peptide moiety having the formula (II)

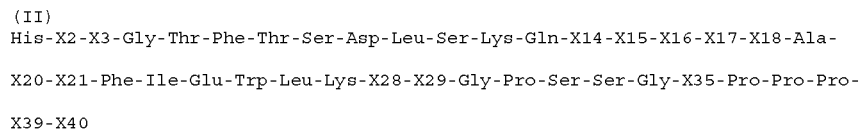

X2 represents an amino acid residue selected from Ser, D-Ser and Aib,

X3 represents an amino acid residue selected from Gln, His and α-amino-functionalized Gln, wherein Gln may be functionalized in that an H of the α-$NH_2$ group is substituted by ($C_1$-$C_4$)-alkyl, X14 represents an amino acid residue having a side chain with an —$NH_2$ group, wherein the —$NH_2$ side chain group is functionalized by —C(O)—$R^5$, —C(O)O—$R^5$, —C(O)NH—$R^5$, —S(O)$_2$—$R^5$ or $R^5$, preferably by —C(O)—$R^5$, wherein $R^5$ may be a moiety comprising up to 50 or up to 100 carbon atoms and optionally heteroatoms selected from halogen, N, O, S and/or P, X15 represents an amino acid residue selected from Glu and Asp, X16 represents an amino acid residue selected from Ser, Glu and Lys, X17 represents an amino acid residue selected from Arg, Glu, Gln, Leu, Aib and Lys, X18 represents an amino acid residue selected from Arg, Ala and Lys, X20 represents an amino acid residue selected from Gln, Arg, Lys, His, Glu and Aib, X21 represents an amino acid residue selected from Asp, Leu and Glu, X28 represents an amino acid residue selected from Asn, Arg, Lys, Aib, Ser, Glu, Ala and Asp, X29 represents an amino acid residue selected from Gly, Ala, D-Ala and Thr, X35 represents an amino acid residue selected from Ala, Glu, Arg and Lys, X39 represents Ser or is absent and X40 is absent or represents an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or $R^5$, preferably by —C(O)—$R^5$, wherein $R^5$ may be a moiety comprising up to 50 or up to 100 carbon atoms and optionally heteroatoms selected from halogen, N, O, S and/or P, $R^1$ represents the N-terminal group of the peptidic compound and is selected from $NH_2$ and mono- or bisfunctionalized $NH_2$, $R^2$ represents the C-terminal group of the peptidic compound and is selected from
(i) OH or functionalized OH and
(ii) $NH_2$ or mono- or bisfunctionalized $NH_2$,
or a salt or solvate thereof.

The compounds of the invention are GLP-1 and glucagon receptor agonists as determined by the observation that they are capable of stimulating intracellular cAMP formation.

According to another embodiment, the compounds of the invention, particularly with a lysine at position 14 which is further substituted with a lipophilic residue, exhibit at least a relative activity of 0.1%, more preferably of 0.2%, more preferably of 0.3% and even more preferably of 0.4% compared to that of GLP-1(7-36) at the GLP-1 receptor. Furthermore, the compounds exhibit at least a relative activity of 0.1%, more preferably of 0.2% or of 0.3% or of 0.4% and even more preferably of 0.5% compared to that of natural glucagon at the glucagon receptor.

The term "activity" as used herein preferably refers to the capability of a compound to activate the human GLP-1 receptor and the human glucagon receptor. More preferably the term "activity" as used herein refers to the capability of a compound to stimulate intracellular cAMP formation. The term "relative activity" as used herein is understood to refer to the capability of a compound to activate a receptor in a certain ratio as compared to another receptor agonist or as compared to another receptor. The activation of the receptors by the agonists (e.g. by measuring the cAMP level) is determined as described herein, e.g. as described in the examples.

According to one embodiment, the compounds of the invention have an $EC_{50}$ for hGLP-1 receptor of 450 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less, more preferably of 9 pmol or less, more preferably of 8 pmol or less, more preferably of 7 pmol or less, more preferably of 6 pmol or less, and more preferably of 5 pmol or less.

According to another embodiment, the compounds of the invention have an $EC_{50}$ for hGlucagon receptor of 500 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less.

According to another embodiment, the compounds of the invention have an $EC_{50}$ for hGLP-1 receptor of 450 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less, more preferably of 9 pmol or less, more preferably of 8 pmol or less, more preferably of 7 pmol or less, more preferably of 6 pmol or less, and more preferably of 5 pmol or less, and/or an $EC_{50}$ for hGlucagon receptor of 500 pmol or less, preferably of 200 pmol or less; more preferably of 150 pmol or less, more preferably of 100 pmol or less, more preferably of 90 pmol or less, more preferably of 80 pmol or less, more preferably of 70 pmol or less, more preferably of 60 pmol or less, more preferably of 50 pmol or less, more preferably of 40 pmol or less, more preferably of 30 pmol or less, more preferably of 25 pmol or less, more preferably of 20 pmol or less, more preferably of 15 pmol or less, more preferably of 10 pmol or less.

In still another embodiment, the $EC_{50}$ for both receptors i.e. for the hGLP-1 receptor and the hGlucagon receptor, is 100 pmol or less, more preferably 90 pmol or less, more preferably 80 pmol or less, more preferably 70 pmol or less, more preferably 60 pmol or less, more preferably 50 pmol or less, more preferably 40 pmol or less, more preferably 30 pmol or less, more preferably 25 pmol or less, more preferably 20 pmol or less, more preferably 15 pmol or less, more preferably 10 pmol or less. The $EC_{50}$ for hGLP-1 receptor and hGlucagon receptor may be determined as described in the Methods herein and as used to generate the results described in Example 9.

The compounds of the invention have the ability to reduce the intestinal passage, to increase the gastric content and/or to reduce the food intake of a patient. These activities of the compounds of the invention can be assessed in animal models known to the skilled person and also described herein in the Methods. The results of such experiments are described in Examples 11 and 12. Preferred compounds of the invention may increase the gastric content of mice, preferably of female NMRI-mice, if administered as a single dose, preferably subcutaneous dose, of 0.02 mg/kg body weight by at least 25%, more preferably by at least 30%, more preferably by at least 40%, more preferably by at least 50%, more preferably by at least 60%, more preferably by at least 70%, more preferably by at least 80%.

Preferably, this result is measured 1 h after administration of the respective compound and 30 mins after administration of a bolus, and/or reduces intestinal passage of mice, preferably of female NMRI-mice, if administered as a single dose, preferably subcutaneous dose, of 0.02 mg/kg body weight at least by 45%; more preferably by at least 50%, more preferably by at least 55%, more preferably by at least 60%, and more preferably at least 65%; and/or reduces food intake of mice, preferably of female NMRI-mice, over a period of 22 h, if administered as a single dose, preferably subcutaneous dose of 0.01 mg/kg body weight by at least 10%, more preferably 15%, and more preferably 20%.

The compounds of the invention have the ability to reduce blood glucose level, and/or to reduce HbA1c levels of a patient. These activities of the compounds of the invention can be assessed in animal models known to the skilled person and also described herein in the Methods. The results of such experiments are described in Examples 14 and 17.

Preferred compounds of the invention may reduce blood glucose level of mice, preferably in female leptin-receptor deficient diabetic db/db mice over a period of 24 h, if administered as a single dose, preferably subcutaneous dose, of 0.01 mg/kg body weight by at least 4 mmol/L; more preferably by at least 6 mmol/L, more preferably by at least 8 mmol/L. If the dose is increased to 0.1 mg/kg body weight a more pronounced reduction of blood glucose levels can be observed in mice over a period of 24 h, if administered as a single dose, preferably subcutaneous dose. Preferably the compounds of the invention lead to a reduction by at least 7 mmol/L; more preferably by at least 9 mmol/L, more preferably by at least 11 mmol/L. The compounds of the invention preferably reduce the increase of HbA1c levels of mice over a period of 4 weeks, if administered at a daily dose of 0.01 mg/kg to about the ignition value.

The compounds of the invention also have the ability to reduce body weight of a patient. These activities of the compounds of the invention can be assessed in animal models known to the skilled person and also described herein in the Methods and in Examples 13 and 16.

It was found that peptidic compounds of the formula (I), particularly those with a lysine at position 14 which is further substituted with a lipophilic residue, showed increased glucagon receptor activation compared to derivatives having the original methionine (from exendin-4) at position 14. Furthermore, oxidation (in vitro or in vivo) of methionine is not possible anymore.

In one embodiment the compounds of the invention have a high solubility at acidic and/or physiological pH values, e.g., at pH 4.5 and/or at pH 7.4 at 25° C., in another embodiment at least 0.5 mg/ml and in a particular embodiment at least 1.0 mg/ml.

Furthermore, according to one embodiment, the compounds of the invention preferably have a high stability when stored in solution. Preferred assay conditions for determining the stability is storage for 7 days at 25° C. in solution at pH 4.5 or pH 7. The remaining amount of peptide is determined by chromatographic analyses as described in the Examples. Preferably, after 7 days at 25° C. in solution at pH 4.5 or pH 7, the remaining peptide amount is at least 80%, more preferably at least 85%, even more preferably at least 90% and even more preferably at least 95%.

Preferably, the compounds of the present invention comprise a peptide moiety Z (II) which is a linear sequence of 39-40 amino carboxylic acids, particularly α-amino carboxylic acids linked by peptide, i.e. carboxamide bonds.

In an embodiment $R^1$ is selected from —$NH_2$, —NH[($C_1$-$C_5$)alkyl], —N[($C_1$-$C_5$)alkyl]$_2$, —NH[($C_0$-$C_4$)alkylene-($C_3$-$C_8$)cycloalkyl], NH—C(O)—H, NH—C(O)—($C_1$-$C_5$)-alkyl, NH—C(O)—($C_0$-$C_3$)alkylene-($C_3$-$C_8$)cycloalkyl, in which alkyl or cycloalkyl is unsubstituted or up to 5-fold substituted by —OH or halogen selected from F, Cl, Br and I, preferably F.

In an embodiment $R^2$ is selected from —OH, —O—($C_1$-$C_{20}$)alkyl, —O($C_0$-$C_8$)alkylene-($C_3$-$C_8$)cycloalkyl, —$NH_2$, —NH[($C_1$-$C_{30}$)alkyl], —N[($C_1$-$C_{30}$)alkyl]$_2$, —NH[(C0-C8)alkylene-($C_3$-$C_8$)cycloalkyl], —N[(C0-C8)alkylene-($C_3$-$C_8$)cycloalkyl]$_2$, —NH[($CH_2$—$CH_2$—O)$_{1-40}$—($C_1$-$C_4$)alkyl], —NH—($C_3$-$C_8$)heterocyclyl or —NH—($C_0$-$C_8$)alkylene-aryl, wherein aryl is selected from phenyl and naphthyl, preferably phenyl, or a ($C_3$-$C_8$)-heterocyclyl containing 1 N-atom and optionally two additional heteroatoms selected from O, N or S, particularly selected from azetidinyl, pyrrolidinyl, piperidinyl, morpholinyl and homopiperidinyl. Moreover alkyl or cycloalkyl as described above is unsubstituted or up to 5-fold substituted by —OH or halogen selected from F, Cl, Br and I, preferably F.

In one embodiment, the N-terminal group $R^1$ is $NH_2$. In a further embodiment, the C-terminal group $R^2$ is $NH_2$. In still a further embodiment the N-terminal group $R^1$ and the C-terminal group $R^2$ are $NH_2$.

In one embodiment position X14 represents an amino acid residue with a functionalized —$NH_2$ side chain group, such as functionalized Lys, Orn, Dab, or Dap, more preferably functionalized Lys, and X40 represents an amino acid residue with a functionalized —$NH_2$ side chain group, such as functionalized Lys, Orn, Dab, or Dap, more preferably functionalized Lys.

An amino acid residue with an —$NH_2$ side chain group, e.g. Lys, Orn, Dab or Dap, may be functionalized in that at least one H atom of the —$NH_2$ side chain group is replaced by —C(O)—$R^5$, —C(O)O—$R^5$, —C(O)NH—$R^5$, —S(O)$_2$—$R^5$ or $R^5$, preferably by —C(O)—$R^5$, wherein $R^5$ may be a moiety comprising up to 50 or up to 100 carbon atoms and optionally heteroatoms selected from halogen, N, O, S and/or P.

In certain embodiments, $R^5$ may comprise a lipophilic moiety, e.g. an acyclic linear or branched saturated hydrocarbon group, wherein $R^5$ particularly comprises an acyclic linear or branched ($C_4$-$C_{30}$) saturated or unsaturated hydrocarbon group, and/or a cyclic saturated, unsaturated or aromatic group, particularly a mono-, bi-, or tricyclic group comprising 4 to 14 carbon atoms and 0, 1, or 2 heteroatoms selected from N, O, and S, e.g. cyclohexyl, phenyl, biphenyl, chromanyl, phenanthrenyl or naphthyl, wherein the acyclic or cyclic group may be unsubstituted or substituted e.g. by halogen, —OH and/or $CO_2H$.

More preferred groups $R^5$ may comprise a lipophilic moiety, e.g. an acyclic linear or branched ($C_{12}$-$C_{22}$) saturated or unsaturated hydrocarbon group. The lipophilic moiety may be attached to the —$NH_2$ side chain group by a linker in all stereoisomeric forms, e.g. a linker comprising one or more, e.g. 2, amino acid linker groups such as γ-aminobutyric acid (GABA), ε-aminohexanoic acid (ε-Ahx), γ-Glu and/or β-Ala. In one embodiment the lipophilic moiety is attached to the —$NH_2$ side chain group by a linker. In another embodiment the lipophilic moiety directly attached to the —$NH_2$ side chain group. Specific examples of amino acid linker groups are (β-Ala)$_{1-4}$, (γ-Glu)$_{1-4}$, (ε-Ahx)$_{1-4}$, or (GABA)$_{1-4}$. Preferred amino acid linker groups are R-Ala, γ-Glu, R-Ala-R-Ala and γ-Glu-γ-Glu.

Specific preferred examples for —C(O)—$R^5$ groups are listed in the following Table 1, which are selected from the group consisting of (S)-4-Carboxy-4-hexadecanoylamino-butyryl-, (S)-4-Carboxy-4-octadecanoylamino-butyryl-, 4-Hexadecanoylamino-butyryl-, 4-{3-[(R)-2,5,7,8-tetramethyl-2-((4R,8R)-4,8,12-trimethyl-tridecylychroman-6-ylmcarbonyl]-propionylamino}-butyryl-, 4-octadecanoylamino-butyryl-, 4-((Z)-octadec-9-enoylamino)-butyryl-, 6-[(4,4-Diphenyl-cyclohexyloxy)-hydroxy-phosphoryloxy]-hexanoyl-, Hexadecanoyl-, (S)-4-Carboxy-4-(15-carboxy-pentadecanoylamino)-butyryl-, (S)-4-Carboxy-4-{3-[3-((2S,3R,4S,5R)-5-carboxy-2,3,4,5-tetrahydroxy-pentanoylamino)-propionylamino]-propionylamino}-butyryl-, (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-Carboxy-4-((9Z,12Z)-octadeca-9,12-dienoylamino)-butyryl-, (S)-4-Carboxy-4-[6-((2S,3R,4S,5R)-5-carboxy-2,3,4,5-tetrahydroxy-pentanoylamino)-hexanoylamino]-butyryl-, (S)-4-Carboxy-4-((2S,3R,4S,5R)-5-carboxy-2,3,4,5-tetrahydroxy-pentanoylamino)-butyryl-, (S)-4-Carboxy-4-tetradecanoylamino-butyryl-, (S)-4-(1'-Benzyloxycarbonyl-undecanoylamino)-4-carboxy-butyryl-, (S)-4-Carboxy-4-[11-(2S,3R,4R,5R)-2,3,4,5,6-pentahydroxy-hexylcarbamoyl)-undecanoylamino]butyryl-, (S)-4-Carboxy-4-((Z)-octadec-9-enoylamino)-butyryl-, (S)-4-Carboxy-4-(4-dodecyloxy-benzoylamino)-butyryl-, (S)-4-Carboxy-4-henicosanoylamino-butyryl-, (S)-4-Carboxy-4-docosanoylamino-butyryl-, (S)-4-Carboxy-4-((Z)-nonadec-10-enoylamino)-butyryl-, (S)-4-Carboxy-4-(4-decyloxy-benzoylamino)-butyryl-, (S)-4-Carboxy-4-[(4'-octyloxy-biphenyl-4-carbonyl)-amino]-butyryl-, (S)-4-Carboxy-4-(12-phenyl-dodecanoylamino)-butyryl-, (S)-4-Carboxy-4-icosanoylamino-butyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylamino-propionylamino)-propionyl-, 3-(3-Hexadecanoylamino-propionylamino)-propionyl-, 3-Hexadecanoylamino-propionyl-, (S)-4-Carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino]-butyryl-, (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl-, (S)-4-Carboxy-4-((9S,10R)-9,10,16-trihydroxy-hexadecanoylamino)-butyryl-, Tetradecanoyl-, 11-Carboxy-undecanoyl-, 11-Benzyloxycarbonyl-undecanoyl-, (S)-4-Carboxy-4-((S)-4-carboxy-4-tetradecanoylamino-butyrylamino)-butyryl-, 6-[Hydroxy-(naphthalene-2-yloxy)-phosphoryloxy]-hexanoyl-, 6-[Hydroxy-(5-phenyl-pentyloxy)-phosphoryloxy]-hexanoyl-, 4-(Naphthalene-2-sulfonylamino)-4-oxo-butyryl-, 4-(Biphenyl-4-sulfonylamino)-4-oxo-butyryl-, (S)-4-Carboxy-4-{(S)-4-carboxy-4-[2-(2-{2-[2-(2-{2-[(S)-4-carboxy-4-(17-carboxy-heptadecanoylamino)-butyrylamino]-ethoxy}-ethoxy)-acetylamino]ethoxy}-ethoxy)-acetylamino]-butyrylamino}-butyryl-, (S)-4-Carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl-, (S)-4-Carboxy-2-{(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl-, (S)-4-Carboxy-2-[2-(2-{2-[2-(2-{2-[(S)-4-carboxy-4-(17-carboxy-heptadecanoylamino)-butyrylamino]-ethoxy}- ethoxy)-acetylamino]-ethoxy}-ethoxy)-acetylamino]-butyryl-, (S)-4-Carboxy-4-{(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino}-butyryl-, (S)-4-Carboxy-4-[2-(2-{2-[(S)-4-carboxy-4-(17-carboxy-heptadecanoylamino)-butyrylamino]-ethoxy}-ethoxy)-acetylamino]-butyryl-, (S)-4-Carboxy-2-{(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino}-butyryl-, (S)-4-Carboxy-2-[2-(2-{2-[(S)-4-carboxy-4-(17-carboxy-heptadecanoylamino)-butyrylamino]-ethoxy}-ethoxy)-acetylamino]-butyryl-, 2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl-, 2-(2-{2-[(S)-4-Carboxy-4-(17-carboxy-heptadecanoylamino)-butyrylamino]-ethoxy}-ethoxy)-acetyl, (S)-4-Carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl, 2-(2-{2-[2-(2-{2-[(S)-4-Carboxy-4-(16-1H-tetrazol-5-yl-hexadecanoylamino)-butyrylamino]-ethoxy}-ethoxy)-acetylamino]-ethoxy}-ethoxy)-acetyl-, 2-(2-{2-[2-(2-{2-[(S)-4-Carboxy-4-(16-carboxy-hexadecanoylamino)-butyrylamino]-ethoxy}-ethoxy)-acetylamino]-ethoxy}-ethoxy)-acetyl-, (S)-4-Carboxy-4-{(S)-4-carboxy-4-[(S)-4-carboxy-4-(17-carboxy-heptadecanoylamino)-butyrylamino]-butyrylamino}-butyryl-, (S)-4-Carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl-, (S)-4-Carboxy-4-{(S)-4-carboxy-4-[2-(2-{2-[2-(2-{2-[(S)-4-carboxy-4-(7-carboxy-heptanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl-, (S)-4-Carboxy-4-{(S)-4-carboxy-4-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetylamino]-butyrylamino}-butyryl-, and (S)-4-Carboxy-4-{(S)-4-carboxy-4-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl-.

Further preferred are stereoisomers, particularly enantiomers of these groups, either S- or R-enantiomers. The term "R" in Table 1 is intended to mean the attachment site of —C(O)—$R^5$ at the peptide back bone, i.e. particularly the ε-amino group of Lys.

TABLE 1

| structure | IUPAC | name |
|---|---|---|
| (hexadecanoyl-glutamic acid amide structure) | (S)-4-Carboxy-4-hexadecanoylamino-butyryl- | yE-x53 |
| (octadecanoyl-glutamic acid amide structure) | (S)-4-Carboxy-4-octadecanoylamino-butyryl- | yE-x70 |
| (hexadecanoylamino-butyryl structure) | 4-Hexadecanoylamino-butyryl- | GABA-x53 |
| (tocopherol ester with propionylamino-butyryl chain) | 4-{3-[(R)-2,5,7,8-tetramethyl-2-((4R,8R)-4,8,12-trimethyl-tridecyl)-chroman-6-yloxycarbonyl]-propionylamino}-butyryl | GABA-x60 |
| (octadecanoylamino-butyryl structure) | 4-octadecanoylamino-butyryl- | GABA-x70 |

TABLE 1-continued

| structure | IUPAC | name |
|---|---|---|
| (alkenyl chain with amide linkage to R) | 4-((Z)-octadec-9-enoylamino)-butyryl- | GABA-x74 |
| (4,4-diphenylcyclohexyl phosphate ester with hexanoyl-R) | 6-[(4,4-Diphenyl-cyclohexyloxy)-hydroxy-phosphoryloxy]-hexanoyl- | Phospho1 |
| (hexadecanoyl chain to R) | Hexadecanoyl- | x53 |
| (pentadecanoyl-amino-butyryl-R with carboxy group) | (S)-4-Carboxy-4-(15-carboxy-pentadecanoylamino)-butyryl- | x52 |
| (tetrahydroxy pentanoylamino propionylamino-linked carboxy butyryl-R) | (S)-4-Carboxy-4-{3-[3-((2S,3R,4S,5R)-5-carboxy-2,3,4,5-tetrahydroxy-pentanoylamino)-propionylamino]-propionylamino}-butyryl | γE-x59 |

TABLE 1-continued

| structure | IUPAC | name |
|---|---|---|
| 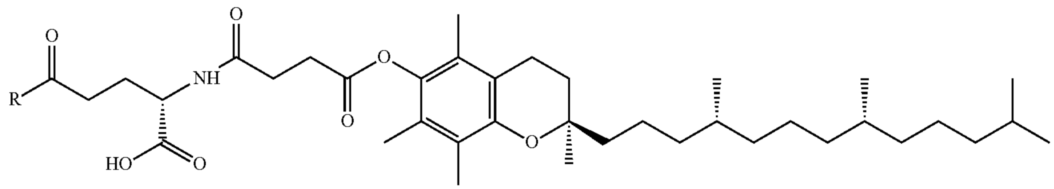 | (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl- | γE-x60 |
| | (S)-4-Carboxy-4-((9Z,12Z)-octadeca-9,12-dienoylamino)-butyryl- | γE-x61 |
| | (S)-4-Carboxy-4-[6-((2S,3R,4S,5R)-5-carboxy-pentanoylamino)-hexanoylamino]-butyryl | γE-x64 |
| 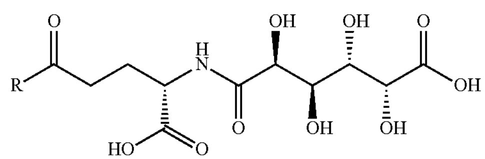 | (S)-4-Carboxy-4-((2S,3R,4S,5R)-5-carboxy-2,3,4,5-tetrahydroxy-pentanoylamino)-butyryl | γE-x65 |
| 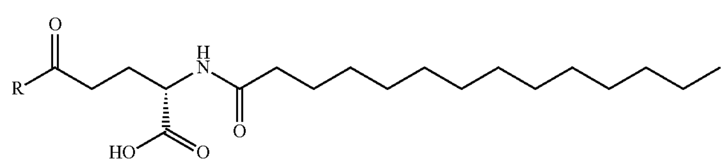 | (S)-4-Carboxy-4-tetradecanoylamino-butyryl- | γE-x69 |

TABLE 1-continued

| name | IUPAC | structure |
|---|---|---|
| γE-x72 | (S)-4-(11-Benzyloxycarbonyl-undecanoylamino)-4-carboxy-butyryl | |
| γE-x73 | (S)-4-Carboxy-4-[11-((2S,3R,4R,5R)-2,3,4,5,6-pentahydroxy-hexylcarbamoyl)undecanoylamino]-butyryl- | |
| γE-x74 | (S)-4-Carboxy-4-((Z)-octadec-9-enoylamino)-butyryl- | |
| γE-x75 | (S)-4-Carboxy-4-(4-dodecyloxy-benzoylamino)-butyryl- | |
| γE-x76 | (S)-4-Carboxy-4-henicosanoylamino-butyryl- | |

TABLE 1-continued

| structure | IUPAC | name |
|---|---|---|
| 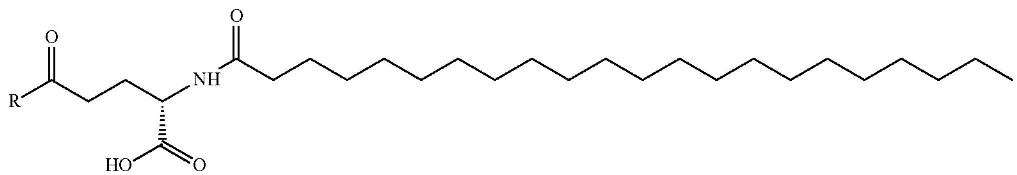 | (S)-4-Carboxy-4-docosanoylamino-butyryl- | γE-x77 |
| 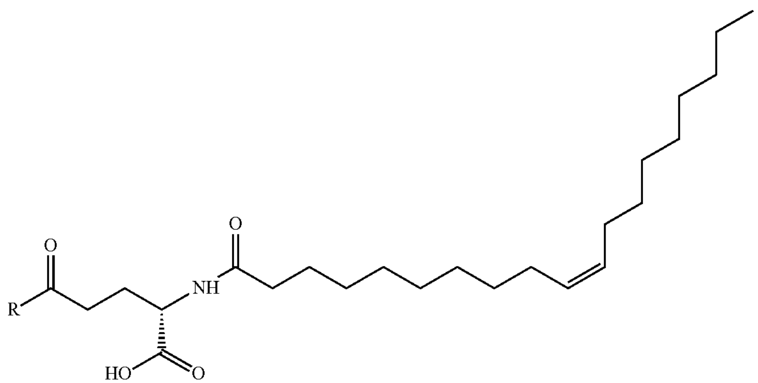 | (S)-4-Carboxy-4-((Z)-nonadec-10-enoylamino)-butyryl- | γE-x79 |
| 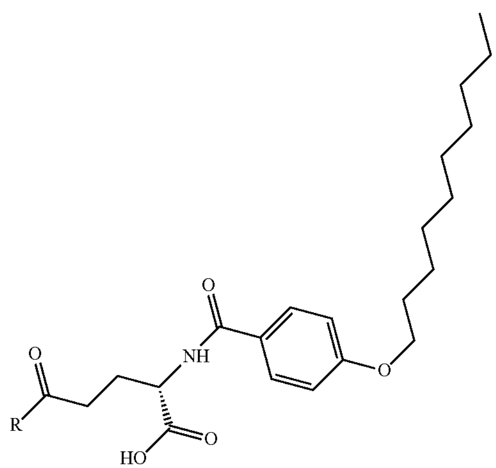 | (S)-4-Carboxy-4-(4-decyloxy-benzoylamino)-butyryl- | γE-x80 |

TABLE 1-continued

| structure | IUPAC | name |
|---|---|---|
| 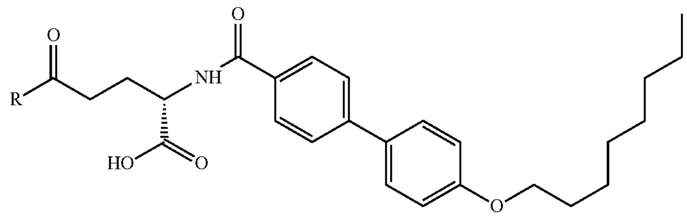 | (S)-4-Carboxy-4-[{4'-octyloxy-biphenyl-4 carbonyl)-amino]-butyryl- | γE-x81 |
| 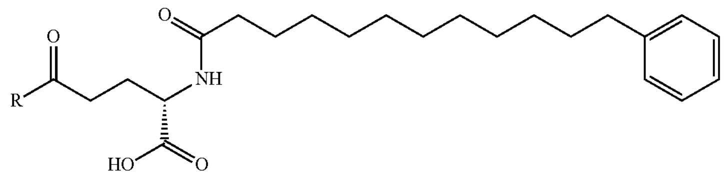 | (S)-4-Carboxy-4-(12-phenyl-dodecanoylamino)-butyryl- | γE-x82 |
| 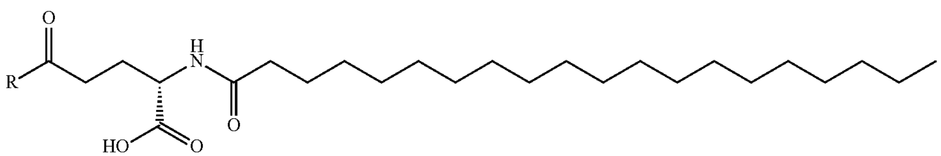 | (S)-4-Carboxy-4-icosanoylamino-butyryl- | γE-X95 |
| 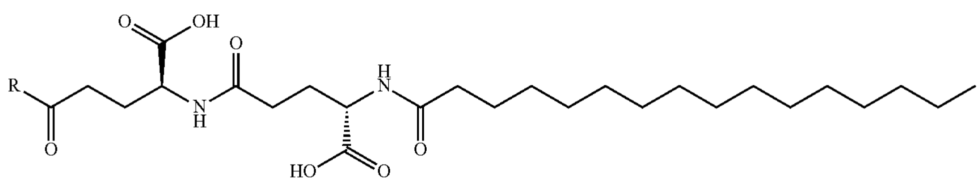 | (S)-4-Carboxy-4-((S)-4-carboxy-4-hexadecanoylamino-butyrylamino)-butyryl- | γE-γE-x53 |
| 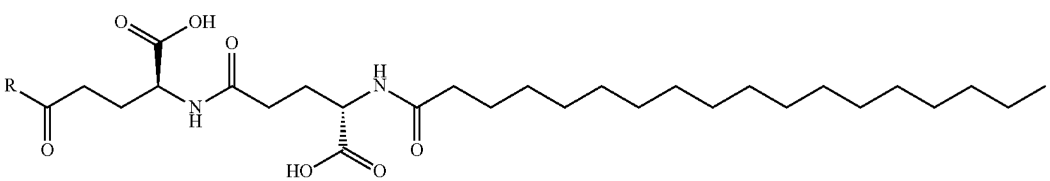 | (S)-4-Carboxy-4-((S)-4-carboxy-4-octadecanoylamino-butyrylamino)-butyryl- | γE-γE-x70 |
| 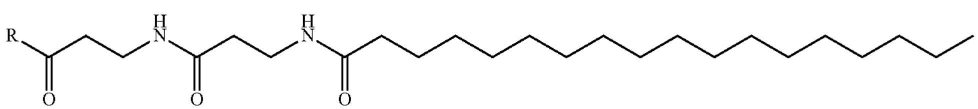 | 3-(3-Octadecanoylamino-propionyl-amino)-propionyl- | β-Ala-β-Ala-x70 |

TABLE 1-continued

| structure | IUPAC | name |
|---|---|---|
| 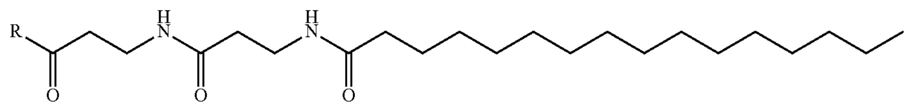 | 3-(3-Hexadecanoylamino-propionyl-amino)-propionyl- | β-Ala-β-Ala-x53 |
| 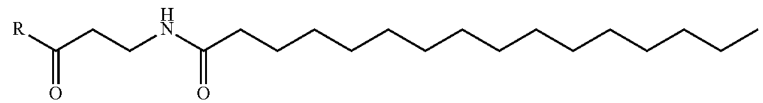 | 3-Hexadecanoylamino-propionyl- | β-Ala-x53 |
| | (S)-4-Carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino]-butyryl- | γE-x16 |
| 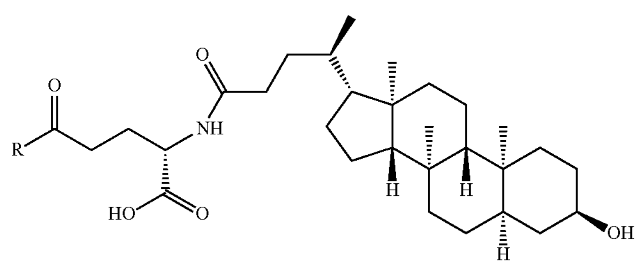 | (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl- | γE-x19 |
| 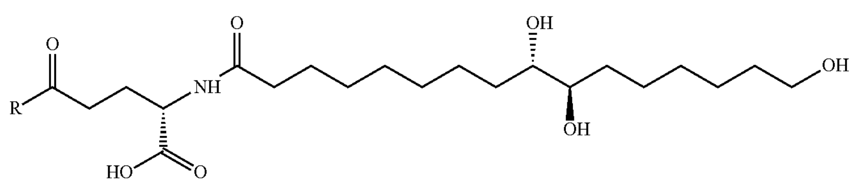 | (S)-4-Carboxy-4-((9S,10R)-9(10,16-trihydroxy-hexadecanoylamino)-butyryl- | γE-x25 |
| 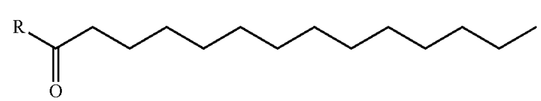 | tetradecanoyl- | x69 |

TABLE 1-continued

| structure | IUPAC | name |
|---|---|---|
| (11-carboxy-undecanoyl structure) | 11-Carboxy-undecanoyl- | x71 |
| (11-benzyloxycarbonyl-undecanoyl structure) | 11-Benzyloxycarbonyl-undecanoyl | x72 |
| ((S)-4-Carboxy-4-((S)-4-carboxy-4-tetradecanoylamino-butyrylamino)-butyryl structure) | (S)-4-Carboxy-4-((S)-4-carboxy-4-tetradecanoylamino-butyrylamino)-butyryl- | γE-γE-x69 |
| (6-[Hydroxy-(naphthalen-2-yloxy)-phosphoryloxy]-hexanoyl structure) | 6-[Hydroxy-(naphthalen-2-yloxy)-phosphoryloxy]-hexanoyl- | Phospho2 |

TABLE 1-continued
| structure | IUPAC | name |
|---|---|---|
| 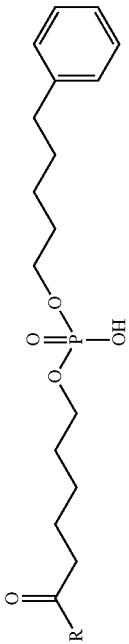 | 6-[Hydroxy-(5-phenyl-pentyloxy)-phosphoryloxy]-hexanoyl- | Phospho3 |
| 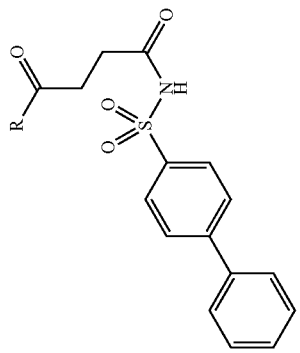 | 4-(Naphthalene-2-sulfonylamino)-4-oxo-butyryl- | Sulfonamid 1 |
| 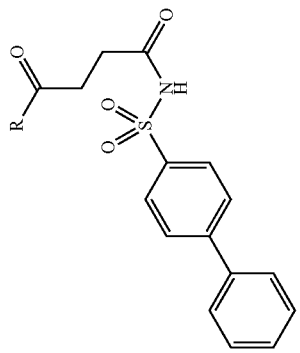 | 4-(Biphenyl-4-sulfonylamino)-4-oxo-butyryl- | Sulfonamid 2 |

TABLE 1-continued

| structure | IUPAC name | name |
|---|---|---|
| [structure] | (S)-4-Carboxy-4-{(S)-4-carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl- | x100 |
| [structure] | (S)-4-Carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl | x101 |

TABLE 1-continued

| structure | IUPAC | name |
|---|---|---|
| | (S)-4-Carboxy-2-[2-{(S)-4-carboxy-2-[2-(2-{2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl | x102 |
| 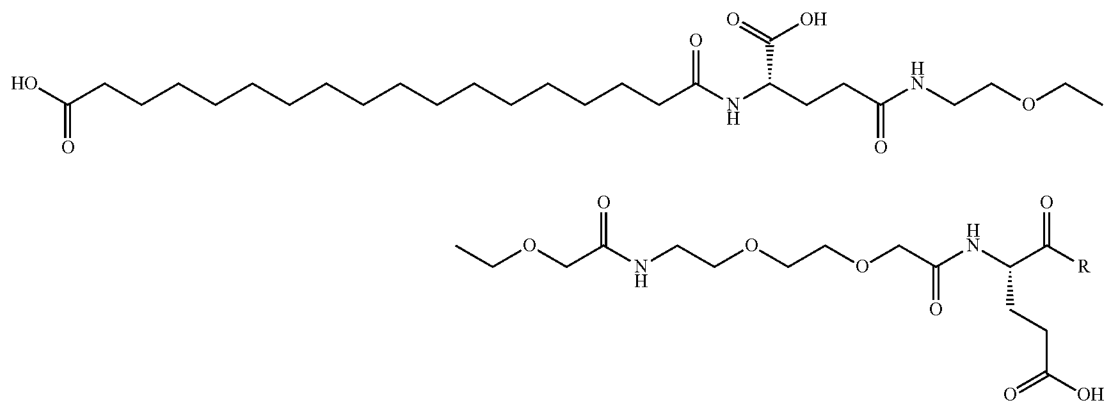 | (S)-4-Carboxy-2-[2-(2-{2-[2-(2-{2-[(S)-((4-carboxy-4-(17-carboxy-heptadecanoylamino)-butyrylamino]-ethoxy}-ethoxy)-acetylamino]-ethoxy}-ethoxy)-acetylamino]-butyryl | x103 |

TABLE 1-continued
| structure | IUPAC | name |
|---|---|---|
| 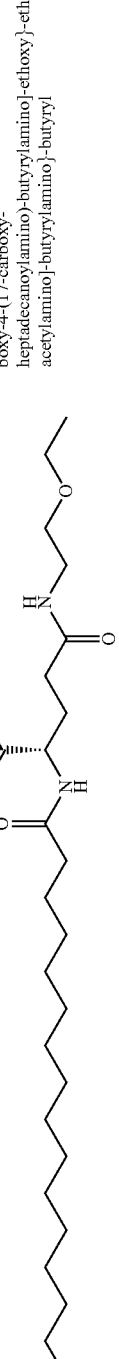 | (S)-4-Carboxy-4-[(S)-4-carboxy-4-[2-(2-{2-[(S)-((4-carboxy-heptadecanoyl)amino)-butyrylamino]-ethoxy}-ethoxy)-acetylamino]-butyrylamino]-butyryl | x104 |
| 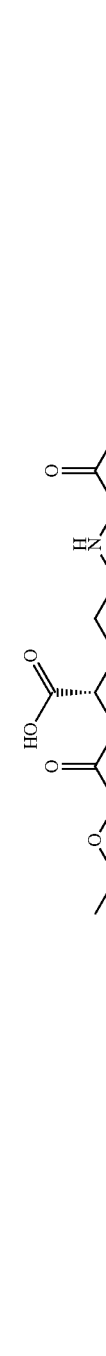 | (S)-4-Carboxy-4-[2-(2-{2-[(S)-4-carboxy-4-(17-carboxy-heptadecanoylamino)-butyrylamino]-ethoxy}-ethoxy)-acetylamino]-butyryl | x105 |

TABLE 1-continued

| structure | IUPAC | name |
|---|---|---|
| | (S)-4-Carboxy-2-[(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino]-butyryl | x106 |
| 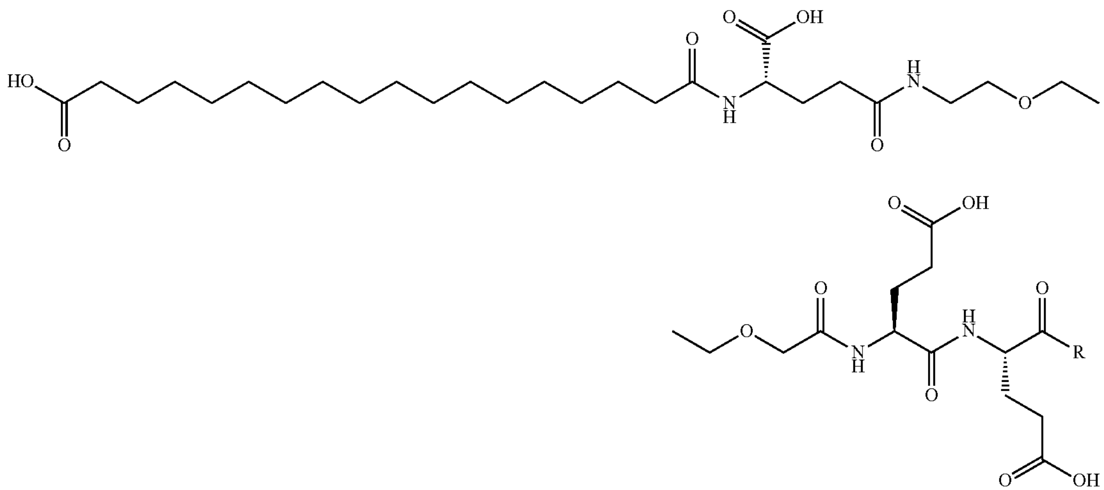 | (S)-4-Carboxy-2-[2-(2-{2-[(S)-4-carboxy-4-(17-carboxy-heptadecanoylamino)-butyrylamino]-ethoxy}-ethoxy)-acetylamino]-butyryl | x107 |

TABLE 1-continued

| structure | IUPAC | name |
|---|---|---|
| 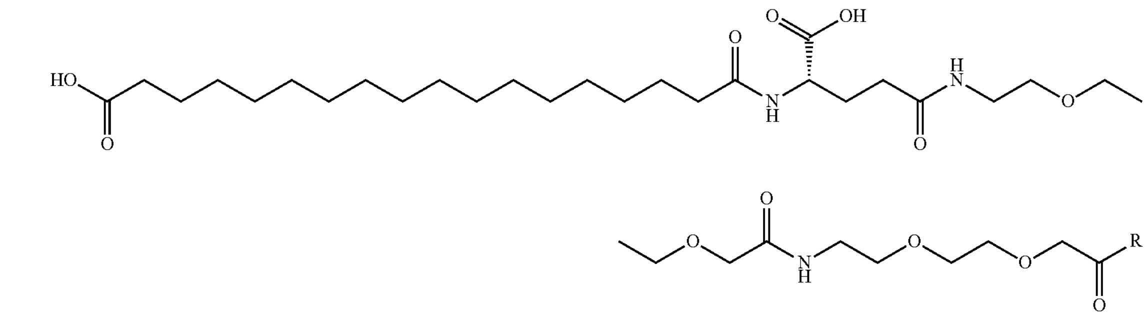 | 2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl- | x108 |
| 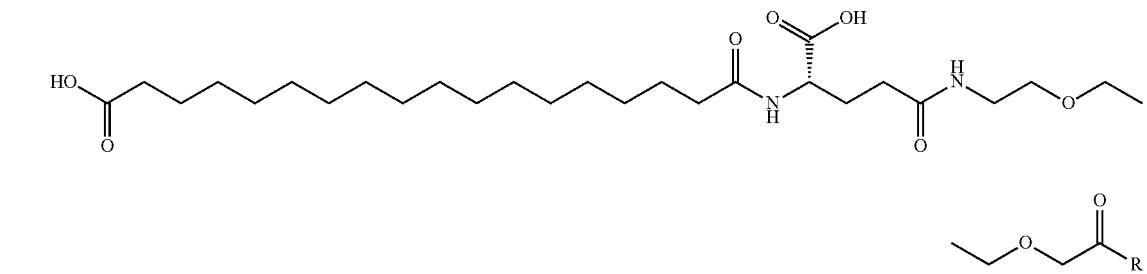 | 2-(2-{2-[(S)-4-Carboxy-4-(17-carboxy-heptadecanoylamino)-butyrylamino]-ethoxy}-ethoxy)-acetyl | x109 |
| | (S)-4-Carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl | x110 |

TABLE 1-continued
| structure | IUPAC name | name |
|---|---|---|
| 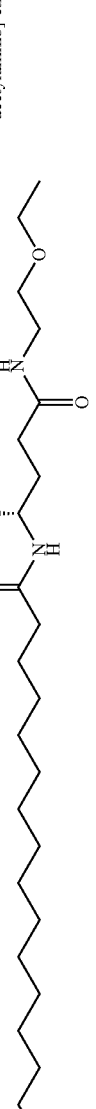 | 2-(2-{2-[2-(2-{2-[(S)-4-Carboxy-4-(19-1H-tetrazol-5-yl-hexadecanoylamino)-butyrylamino]-ethoxy}-acetylamino]-ethoxy})-acetyl | X111 |
| 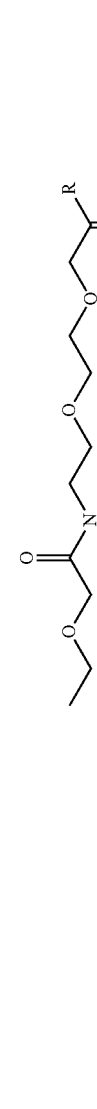 | 2-(2-{2-[2-(2-{2-[(S)-4-Carboxy-4-(16-carboxy-hexadecanoylamino)-butyrylamino]-ethoxy}-acetylamino]-ethoxy})-acetyl | X112 |
| 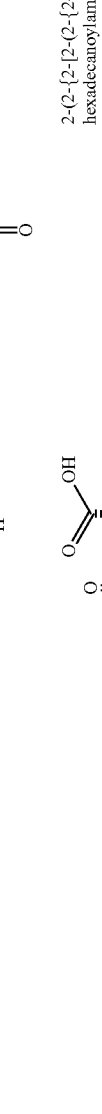 | (S)-4-Carboxy-4-{(S)-4-[(S)-4-carboxy-4-(17-carboxy-heptadecanoylamino)-butyrylamino]-butyrylamino}-butyryl | X113 |

TABLE 1-continued

| structure | IUPAC | name |
|---|---|---|
| (structure) | (S)-4-Carboxy-4-{(S)-4-carboxy-4-{2-[2-(2-{2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino} | x114 |
| (structure) | (S)-4-Carboxy-4-{(S)-4-carboxy-4-{2-[2-(2-{2-(2-{(S)-4-carboxy-4-(7-carboxy-heptanoylamino)-butyrylamino]-ethoxy}-ethoxy)-acetylamino]-ethoxy}-ethoxy)-acetylamino]-butyryl | x115 |
| (structure) | (S)-4-Carboxy-4-{(S)-4-carboxy-4-{2-[2-(2-{2-[2-(2-{(S)-4-carboxy-4-(11-carboxy-undecanoylamino)-butyrylamino}-ethoxy)-ethoxy]-acetylamino}-ethoxy)-ethoxy]-acetylamino}-butyryl | x116 |

TABLE 1-continued

| structure | IUPAC | name |
|---|---|---|
| | (S)-4-Carboxy-4-{(S)-4-carboxy-4-[2-(2-{2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl | x117 |
| | (S)-4-Carboxy-4-{(S)-4-carboxy-4-[2-(2-{2-(2-{2-[(S)-4-carboxy-4-(15-carboxy-pentacanoylamino)-butyrylamino]-ethoxy}-ethoxy)-acetylamino]-ethoxy}-ethoxy)-acetylamino]-butyrylamino}-butyryl | x118 |

TABLE 1-continued

| structure | IUPAC | name |
|---|---|---|
| 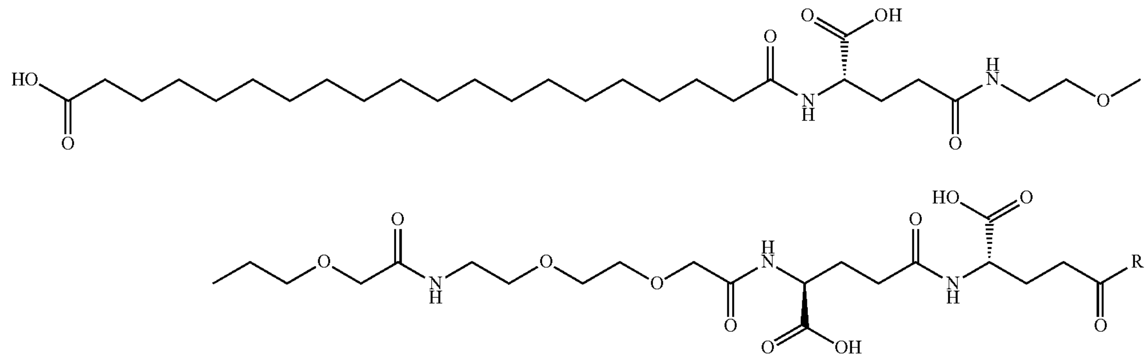 | (S)-4-Carboxy-4-{(S)-4-carboxy-4-[2-(2-{2-[2-(2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl | x119 |

According to one embodiment, —C(O)—R⁵ is selected from the group consisting of (S)-4-carboxy-4-hexadecanoylamino-butyryl (γE-x53), (S)-4-carboxy-4-octadecanoylamino-butyryl (γE-x70), 4-hexadecanoylamino-butyryl (GABA-x53), 4-{3-[(R)-2,5,7,8-tetramethyl-2-((4R,8R)-4,8,12-trimethyl-tridecyl)-chroman-6-yloxycarbonyl]-propionylamino}-butyryl-(GABA-x60), 4-octadecanoylamino-butyryl (GABA-x70), 4-((Z)-octadec-9-enoylamino)-butyryl (GABA-x74), 6-[(4,4-Diphenyl-cyclohexyloxy)-hydroxy-phosphoryloxy]-hexanoyl (Phospho1), Hexadecanoyl (x53), (S)-4-Carboxy-4-(15-carboxy-pentadecanoylamino)-butyryl (x52), (S)-4-Carboxy-4-{3-[3-((2S,3R,4S,5R)-5-carboxy-2,3,4,5-tetrahydroxy-pentanoylamino)-propionylamino]-propionylamino}-butyryl (γE-x59), (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl (γE-x60), (S)-4-Carboxy-4-((9Z,12Z)-octadeca-9,12-dienoylamino)-butyryl (γE-x61), (S)-4-Carboxy-4-[6-((2S,3R,4S,5R)-5-carboxy-2,3,4,5-tetrahydroxy-pentanoylamino)-hexanoylamino]-butyryl (γE-x64), (S)-4-Carboxy-4-((2S,3R,4S,5R)-5-carboxy-2,3,4,5-tetrahydroxy-pentanoylamino)-butyryl (γE-x65), (S)-4-carboxy-4-tetradecanoylamino-butyryl (γE-x69), (S)-4-(11-Benzyloxycarbonyl-undecanoylamino)-4-carboxy-butyryl (γE-x72), (S)-4-carboxy-4-[11-((2S,3R,4R,5R)-2,3,4,5,6-pentahydroxy-hexylcarbamoyl)-undecanoylamino]-butyryl (γE-x73), (S)-4-Carboxy-4-((Z)-octadec-9-enoylamino)-butyryl (γE-x74), (S)-4-Carboxy-4-(4-dodecyloxy-benzoylamino)-butyryl (γE-x75), (S)-4-Carboxy-4-henicosanoylamino-butyryl (γE-x76), (S)-4-Carboxy-4-docosanoylamino-butyryl (γE-x77), (S)-4-Carboxy-4-((Z)-nonadec-10-enoylamino)-butyryl (γE-x79), (S)-4-Carboxy-4-(4-decyloxy-benzoylamino)-butyryl (γE-x80), (S)-4-Carboxy-4-[(4'-octyloxy-biphenyl-4-carbonyl)-amino]-butyryl (γE-x81), (S)-4-Carboxy-4-(12-phenyl-dodecanoylamino)-butyryl (γE-x82), (S)-4-Carboxy-4-icosanoylamino-butyryl (γE-x95), (S)-4-Carboxy-4-((S)-4-carboxy-4-hexadecanoylamino-butyrylamino)-butyryl (γE-γE-x53), (S)-4-Carboxy-4-((S)-4-carboxy-4-octadecanoylamino-butyrylamino)-butyryl (γE-γE-x70), and 3-(3-Octadecanoylamino-propionylamino)-propionyl(β-Ala-β-Ala-x70).

According to another embodiment, —C(O)—R⁵ is selected from the group consisting of (S)-4-carboxy-4-octadecanoylamino-butyryl (γE-x70), (S)-4-carboxy-4-hexadecanoylamino-butyryl (γE-x53), and hexadecanoyl (x53).

According to yet another embodiment, —C(O)—R⁵ is (S)-4-carboxy-4-hexadecanoylamino-butyryl (γE-x53).

In some embodiments of the invention, position X14 and/or X40 represents Lysine (Lys). According to some embodiments, Lys at position 14 and optionally at position 40 is functionalized, e.g. with a group —C(O)R⁵ as described above. In other embodiments, X40 is absent and X14 is Lys functionalized with —C(O)—R⁵, —C(O)O—R⁵, —C(O)NH—R⁵, —S(O)₂—R⁵ or R⁵, preferably by —C(O)—R⁵, wherein R⁵ is as defined above. In particular, X14 is Lys functionalized with C(O)—R⁵, which is selected from the group consisting of (S)-4-carboxy-4-hexadecanoylamino-butyryl (γE-x53), (S)-4-carboxy-4-octadecanoylamino-butyryl (γE-x70), 4-hexadecanoylamino-butyryl (GABA-x53), 4-{3-[(R)-2,5,7,8-tetramethyl-2-((4R,8R)-4,8,12-trimethyl-tridecyl)-chroman-6-yloxycarbonyl]-propionylamino}-butyryl-(GABA-x60), 4-octadecanoylamino-butyryl (GABA-x70), 4-((Z)-octadec-9-enoylamino)-butyryl (GABA-x74), 6-[(4,4-Diphenyl-cyclohexyloxy)-hydroxy-phosphoryloxy]-hexanoyl (Phospho1), Hexadecanoyl (x53), (S)-4-Carboxy-4-(15-carboxy-pentadecanoylamino)-butyryl (x52), (S)-4-Carboxy-4-{3-[3-(2S,3R,4S,5R)-5-carboxy-2,3,4,5-tetrahydroxy-pentanoylamino)-propionylamino]-propionylamino}-butyryl (γE-x59), (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl (γE-x60), (S)-4-Carboxy-4-((9Z,12Z)-octadeca-9,12-dienoylamino)-butyryl (γE-x61), (S)-4-Carboxy-4-[6-((2S,3R,4S,5R)-5-carboxy-2,3,4,5-tetrahydroxy-pentanoylamino)-hexanoylamino]-butyryl (γE-x64), (S)-4-Carboxy-4-((2S,3R,4S,5R)-5-carboxy-2,3,4,5-tetrahydroxy-pentanoylamino)-butyryl (γE-x65), (S)-4-carboxy-4-tetradecanoylamino-butyryl (γE-x69), (S)-4-(11-Benzyloxycarbonyl-undecanoylamino)-4-carboxy-butyryl (γE-x72), (S)-4-carboxy-4-[11-((2S,3R,4R,5R)-2,3,4,5,6-pentahydroxy-hexylcarbamoyl)-undecanoylamino]-butyryl (γE-x73), (S)-4-Carboxy-4-((Z)-octadec-9-enoylamino)-butyryl (γE-x74), (S)-4-Carboxy-4-(4-dodecyloxy-benzoylamino)-butyryl (γE-x75), (S)-4-Carboxy-4-henicosanoylamino-butyryl (γE-x76), (S)-4-Carboxy-4-docosanoylamino-butyryl (γE-x77), (S)-4-Carboxy-4-((Z)-nonadec-10-enoylamino)-butyryl (γE-x79), (S)-4-Carboxy-4-(4-decyloxy-benzoylamino)-butyryl (γE-x80), (S)-4-Carboxy-4-[(4'-octyloxy-biphenyl-4-carbonyl)-amino]-butyryl (γE-x81), (S)-4-Carboxy-4-(12-phenyl-dodecanoylamino)-butyryl (γE-x82), (S)-4-Carboxy-4-icosanoylamino-butyryl (γE-x95), (S)-4-Carboxy-4-((S)-4-carboxy-4-hexadecanoylamino-butyrylamino)-butyryl (γE-γE-x53), (S)-4-Carboxy-4-((S)-4-carboxy-4-octadecanoylamino-butyrylamino)-butyryl (γE-γE-x70), and 3-(3-Octadecanoylamino-propionylamino)-propionyl(β-Ala-β-Ala-x70).

A further embodiment relates to a group of compounds, wherein
  $R^1$ is $NH_2$,
  $R^2$ is $NH_2$ or
  $R^1$ and $R^2$ are $NH_2$.

A further embodiment relates to a group of compounds, wherein
  X2 represents an amino acid residue selected from Ser, D-Ser and Aib,
  X3 represents an amino acid residue selected from Gln, His and α-amino-functionalized Gln, wherein Gln may be functionalized in that an H of the α-$NH_2$ group is substituted by ($C_1$-$C_4$)-alkyl,
  X14 represents an amino acid residue selected from Lys, Orn, Dab and Dap,
    wherein the —$NH_2$ side chain group is functionalized by —C(O)—R⁵,
  X15 represents an amino acid residue selected from Glu and Asp,
  X16 represents an amino acid residue selected from Ser, Lys and Glu,
  X17 represents an amino acid residue selected from Arg, Glu, Gln, Leu and Lys,
  X18 represents an amino acid residue selected from Arg and Ala, X20 represents an amino acid residue selected from Gln, Arg, Lys and Aib,
X21 represents an amino acid residue selected from Asp, Leu and Glu,
X28 represents an amino acid residue selected from Asn, Arg, Lys, Aib, Ser, Glu, Asp and Ala,
X29 represents an amino acid residue selected from Gly, Ala, D-Ala and Thr,
X35 represents an amino acid residue selected from Ala or Glu,
X39 is Ser or is absent,
X40 is either absent or represents Lys, wherein the —$NH_2$ side chain group can be functionalized by —C(O)—$R^5$ and
—C(O)—$R^5$ is as defined above.

A further embodiment relates to a group of compounds, wherein

X2 represents an amino acid residue selected from D-Ser and Aib,
X3 represents Gln,
X14 represents an amino acid residue selected from Lys and Orn, wherein the —$NH_2$ side chain group is functionalized by —C(O)—$R^5$,
X15 represents an amino acid residue selected from Glu and Asp,
X16 represents an amino acid residue selected from Ser and Glu,
X17 represents an amino acid residue selected from Arg, Gln and Lys,
X18 represents an amino acid residue selected from Arg and Ala,
X20 represents an amino acid residue selected from Gln, Arg, Lys and Aib,
X21 represents an amino acid residue selected from Asp, Leu and Glu,
X28 represents an amino acid residue selected from Asn, Arg, Lys, Aib, Ser and Ala,
X29 represents an amino acid residue selected from Gly, Ala or Thr,
X35 represents Ala,
X39 is Ser or is absent,
X40 is either absent or represents Lys, wherein the —$NH_2$ side chain group can be functionalized by —C(O)—$R^5$ and
—C(O)—$R^5$ is as defined above.

A further embodiment relates to a group of compounds, wherein
X20 represents an amino acid residue selected from Gln, Lys and Aib.

A further embodiment relates to a group of compounds, wherein
X2 represents an amino acid residue selected from D-Ser and Aib,
X3 represents Gln,
X14 represents Lys, wherein the —$NH_2$ side chain group is functionalized by one of the groups selected from 3-(3-octadecanoylamino-propionyl-amino)-propionyl-, 4-hexadecanoylamino-butyryl-, 4-{3-[(R)-2,5,7,8-tetramethyl-2-((4R,8R)-4,8,12-trimethyl-tridecyl)-chroman-6-yloxycarbonyl]-propionylamino}-butyryl-, 4-octadecanoylamino-butyryl-, 4-((Z)-octadec-9-enoylamino)-butyryl-, hexadecanoyl-, (S)-4-carboxy-4-((Z)-octadec-9-enoylamino)-butyryl-, (S)-4-carboxy-4-(4-dodecyloxy-benzoylamino)-butyryl-, (S)-4-carboxy-4-henicosanoylamino-butyryl-, (S)-4-carboxy-4-docosanoylamino-butyryl-, (S)-4-carboxy-4-((Z)-nonadec-10-enoylamino)-butyryl-, (S)-4-carboxy-4-(4-decyloxy-benzoylamino)-butyryl-, (S)-4-carboxy-4-[(4'-octyloxy-biphenyl-4-carbonyl)-amino]-butyryl-, (S)-4-carboxy-4-(12-phenyl-dodecanoylamino)-butyryl-, (S)-4-carboxy-4-((S)-4-carboxy-4-hexadecanoylamino-butyrylamino)-butyryl-, (S)-4-carboxy-4-((S)-4-carboxy-4-octadecanoylamino-butyrylamino)-butyryl-, (S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-carboxy-4-((9Z,12Z)-octadeca-9,12-dienoylamino)-butyryl-, (S)-4-carboxy-4-octadecanoylamino-butyryl- and (S)-4-carboxy-4-hexadecanoylamino-butyryl-,
X15 represents Glu,
X16 represents Ser,
X17 represents an amino acid residue selected from Arg, Gln and Lys,
X18 represents Ala,
X20 represents Gln,
X21 represents Asp,
X28 represents Ala,
X29 represents Gly,
X35 represents Ala,
X39 is Ser
X40 is absent.

A further embodiment relates to a group of compounds of formula (I), wherein
X2 represents Aib,
X3 represents Gln,
X14 represents Lys, wherein the —$NH_2$ side chain group is functionalized, particularly by (S)-4-Carboxy-4-hexadecanoylamino-butyryl- and (S)-4-Carboxy-4-octadecanoylamino-butyryl-;
X15 represents an amino acid residue selected from Asp and Glu,
X16 represents an amino acid residue selected from Ser and Glu,
X17 represents an amino acid residue selected from Gln and Lys,
X18 represents Ala,
X20 represents an amino acid residue selected from Gln and Lys,
X21 represents an amino acid residue selected from Asp and Leu,
X28 represents Ala,
X29 represents an amino acid residue selected from Gly and D-Ala,
X35 represents Ala,
X39 is Ser,
X40 is absent.

A further embodiment relates to a group of compounds, wherein
X2 represents an amino acid residue selected from D-Ser and Aib,
X3 represents Gln,
X14 represents Lys, wherein the —$NH_2$ side chain group is functionalized, particularly by (S)-4-Carboxy-4-octadecanoylamino-butyryl-;
X15 represents Asp,
X16 represents Ser,
X17 represents Arg,
X18 represents Arg,
X20 represents Gln,
X21 represents Asp,
X28 represents Ala,
X29 represents an amino acid residue selected from Gly and D-Ala,
X35 represents Ala, X39 is Ser,
X40 is absent.

A further embodiment relates to a group of compounds, wherein
X2 represents D-Ser,
X3 represents Gln,
X14 represents Lys, wherein the —NH$_2$ side chain group can be functionalized, particularly by (S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-carboxy-4-((9Z,12Z)-octadeca-9,12-dienoylamino)-butyryl-, (S)-4-carboxy-4-tetradecanoylamino-butyryl-, (S)-4-carboxy-4-octadecanoylamino-butyryl-, 2-((S)-4-carboxy-4-{3-[3-((2S,3R,4S,5R)-5-carboxy-2,3,4,5-tetrahydroxy-pentanoylamino)-propionylamino]-propionylamino}-butyryl-, 2-{(S)-4-carboxy-4-[6-((2S,3R,4S,5R)-5-carboxy-2,3,4,5-tetrahydroxy-pentanoylamino)-hexanoylamino]-butyryl-, 2-[(S)-4-carboxy-4-((2S,3R,4S,5R)-5-carboxy-2,3,4,5-tetrahydroxy-pentanoylamino)-butyryl-, 2-[(S)-4-(11-benzyloxycarbonyl-undecanoylamino)-4-carboxy-butyryl-, 2-{(S)-4-carboxy-4-[11-((2S,3R,4R,5R)-2,3,4,5,6-pentahydroxy-hexylcarbamoyl)-undecanoylamino]-butyryl-,
X15 represents Asp,
X16 represents Ser,
X17 represents Arg,
X18 represents Arg,
X20 represents Gln,
X21 represents Asp,
X28 represents Asn,
X29 represents Gly,
X35 represents Ala,
X39 is Ser,
X40 is absent.

A further embodiment relates to a group of compounds, wherein
X2 represents D-Ser,
X3 represents Gln,
X14 represents Lys, wherein the —NH$_2$ side chain group is functionalized, particularly by (S)-4-carboxy-4-hexadecanoylamino-butyryl- or hexadecanoyl-;
X15 represents an amino acid residue selected from Glu or Asp,
X16 represents Ser,
X17 represents Arg,
X18 represents Arg,
X20 represents Gln,
X21 represents Asp,
X28 represents an amino acid residue selected from Asn, Arg, Lys, Aib, Ser, Glu and Asp,
X29 represents an amino acid residue selected from Gly, Ala, D-Ala and Thr,
X35 represents an amino acid residue selected from Ala, Glu, Arg and Lys,
X39 is Ser,
X40 is absent.

A further embodiment relates to a group of compounds, wherein
X2 represents D-Ser,
X3 represents Gln,
X14 represents Lys, wherein the —NH$_2$ side chain group is functionalized, particularly by (S)-4-carboxy-4-hexadecanoylamino-butyryl- or hexadecanoyl-;
X15 represents an amino acid residue selected from Glu and Asp,
X16 represents an amino acid residue selected from Ser and Glu,
X17 represents an amino acid residue selected from Arg, Glu, Lys and Aib,
X18 represents an amino acid residue selected from Arg, Lys and Ala,
X20 represents an amino acid residue selected from Gln, Lys and Aib,
X21 represents an amino acid residue selected from Asp and Leu,
X28 represents an amino acid residue selected from Ala and Asn,
X29 represents Gly,
X35 represents Ala,
X39 is Ser,
X40 is absent.

A further embodiment relates to a group of compounds, wherein
X2 represents D-Ser,
X3 represents Gln,
X14 represents Orn or Dab, wherein the —NH$_2$ side chain group is functionalized, particularly by (S)-4-carboxy-4-hexadecanoylamino-butyryl-;
X15 represents Glu,
X16 represents Ser,
X17 represents Arg,
X18 represents Arg,
X20 represents Gln,
X21 represents Asp,
X28 represents Ala,
X29 represents Gly,
X35 represents Ala,
X39 is Ser,
X40 is absent.

A further embodiment relates to a group of compounds, wherein
X2 represents D-Ser,
X3 represents Gln,
X14 represents Lys, wherein the —NH$_2$ side chain group is functionalized, particularly by (S)-4-carboxy-4-hexadecanoylamino-butyryl- or hexadecanoyl-;
X15 represents an amino acid residue selected from Glu and Asp,
X16 represents Ser,
X17 represents an amino acid residue selected from Arg and Lys,
X18 represents an amino acid residue selected from Arg and Ala,
X20 represents Gln,
X21 represents an amino acid residue selected from Asp and Leu,
X28 represents an amino acid residue selected from Ala and Asn,
X29 represents Gly,
X35 represents Ala,
X39 represents Ser or is absent,
X40 is absent or represents Lys, wherein the —NH$_2$ side chain group is optionally functionalized, particularly by (S)-4-carboxy-4-hexadecanoylamino-butyryl- and
R$^2$ is NH$_2$, NH(C$_1$-C$_{18}$)alkyl, which are unsubstituted or monosubstituted by OH or 3-fold-substituted by F, N[(C$_1$-C$_6$)alkyl]$_2$, NH(CH$_2$—CH$_2$—O)$_{1-24}$—(C$_1$-C$_4$)alkyl-COOH, NH-pyrrolidine (N-pyrrolidin-1-yl-amido), NH-benzyl (N-benzyl-amido) or N-morpholine (1-morpholin-4-yl), particularly by NH$_2$, NH—CH$_2$—CH$_3$, NH—(CH$_2$)$_2$—CH$_3$, NH—C(CH$_3$)$_3$, NH—CH$_2$—CF$_3$, NH—(CH$_2$)$_{12}$—OH, NH—

(CH$_2$)$_{13}$—CH$_3$, NH—(CH$_2$)$_{14}$—CH$_3$, NH—(CH$_2$)$_{15}$—CH$_3$, NH—(CH$_2$)$_{17}$—CH$_3$, NH(CH$_2$—CH$_2$—O)$_4$—CH$_2$—CH$_2$—COOH, NH(CH$_2$—CH$_2$—O)$_{24}$—CH$_2$—CH$_2$—COOH, NH—N(CH$_2$)$_4$, NH—CH$_2$—C$_6$H$_5$, N(CH$_2$—CH$_2$)$_2$O.

A further embodiment relates to a group of compounds, wherein
- X2 represents an amino acid residue selected from Ser, D-Ser and Aib,
- X3 represents an amino acid residue selected from Gln, His, Asn and N$^\alpha$-methylated Gln [Gln ($\alpha$-NHCH$_3$)],
- X14 represents Lys, wherein the —NH$_2$ side chain group is functionalized, particularly by (S)-4-carboxy-4-hexadecanoylamino-butyryl- or hexadecanoyl-;
- X15 represents an amino acid residue selected from Glu and Asp,
- X16 represents an amino acid residue selected from Ser and Lys,
- X17 represents an amino acid residue selected from Arg and Glu,
- X18 represents an amino acid residue selected from Arg and Ala,
- X20 represents an amino acid residue selected from Gln, Arg and Aib,
- X21 represents an amino acid residue selected from Asp and Leu,
- X28 represents an amino acid residue selected from Ala and Asn,
- X29 represents Gly,
- X35 represents Ala,
- X39 is Ser,
- X40 is absent.

A further embodiment relates to a group of compounds of formula (I), wherein
- X2 represents an amino acid residue selected from Ser, D-Ser and Aib,
- X3 represents an amino acid residue selected from Gln, His and N$^\alpha$-methylated Gln [Gln ($\alpha$-NHCH$_3$)],
- X14 represents Lys, wherein the —NH$_2$ side chain group is functionalized, particularly by (S)-4-carboxy-4-hexadecanoylamino-butyryl- or hexadecanoyl-,
- X15 represents an amino acid residue selected from Glu and Asp,
- X16 represents an amino acid residue selected from Ser and Lys,
- X17 represents Arg,
- X18 represents an amino acid residue selected from Arg and Ala,
- X20 represents an amino acid residue selected from Gln and Aib,
- X21 represents an amino acid residue selected from Asp and Leu,
- X28 represents an amino acid residue selected from Ala and Asn,
- X29 represents Gly,
- X35 represents Ala,
- X39 is Ser,
- X40 is absent.

A further embodiment relates to a group of compounds of formula (I), wherein
- X2 represents an amino acid residue selected from D-Ser and Aib,
- X3 represents an amino acid residue selected from Gln and His,
- X14 represents Lys, wherein the —NH$_2$ side chain group is functionalized, particularly by (S)-4-carboxy-4-hexadecanoylamino-butyryl-, (S)-4-carboxy-4-((S)-4-carboxy hexadecanoylamino-butyrylamino)-butyryl-, or (S)-4-carboxy-4-octadecanoyl-amino-butyryl-;
- X15 represents an amino acid residue selected from Glu and Asp,
- X16 represents Glu,
- X17 represents Glu,
- X18 represents Ala,
- X20 represents an amino acid residue selected from Arg and Lys,
- X21 represents Leu,
- X28 represents Ala,
- X29 represents Gly,
- X35 represents Ala,
- X39 is Ser,
- X40 is absent.

A still further preferred embodiment relates to a group of compounds wherein
- X40 is absent.

A still further preferred embodiment relates to a group of compounds, wherein the functionalized Lys in position 14 is functionalized at its $\epsilon$-amino group with —C(O)—R$^5$, and —C(O)—R$^5$ is (S)-4-carboxy-4-hexadecanoyl-amino-butyryl, (S)-4-carboxy-4-octadecanoylamino-butyryl, hexadecanoyl or octadecanoyl.

A still further preferred embodiment relates to a group of compounds wherein
- X2 represents an amino acid residue selected from Aib and D-Ser;
- X3 represents an amino acid residue selected from Gln and His;
- X14 represents Lys, wherein the —NH$_2$ side chain group is functionalized by one of the groups selected from (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylamino-propionylamino)-propionyl-, 3-(3-Hexadecanoylamino-propionylamino)-propionyl-, (S)-4-Carboxy-4-henicosanoylamino-butyryl-, 4-Hexadecanoylamino-butyryl- and 4-octadecanoylamino-butyryl-,
- X15 represents an amino acid residue selected from Asp and Glu;
- X16 represents an amino acid residue selected from Ser and Glu,
- X17 represents an amino acid residue selected from Arg, Gln, Lys, Aib and Leu;
- X18 represents an amino acid residue selected from Arg and Ala;
- X20 represents an amino acid residue selected from Gln, Aib and Lys;
- X21 represents an amino acid residue selected from Asp, Glu and Lys;
- X28 represents an amino acid residue selected from Asn, Ser, Aib, Ala and Arg;
- X29 represents an amino acid residue selected from Gly, Thr, Ala and D-Ala;
- X35 represents Ala;
- X39 represents Ser and
- X40 is absent.

A still further preferred embodiment relates to a group of compounds wherein
X2 represents an amino acid residue selected from Aib and D-Ser;
X3 represents Gln;
X14 represents Lys, wherein the —NH$_2$ side chain group is functionalized by one of the groups selected from (S)-4-carboxy-4-hexadecanoyl-amino-butyryl, (S)-4-carboxy-4-octadecanoylamino-butyryl, hexadecanoyl and octadecanoyl;
X15 represents Glu;
X16 represents Ser;
X17 represents an amino acid residue selected from Arg, Gln and Lys;
X18 represents Ala;
X20 represents Gln;
X21 represents Asp;
X28 represents Ala;
X29 represents Gly;
X35 represents Ala;
X39 represents Ser and
X40 is absent.

A further embodiment relates to a group of compounds, wherein
X2 represents Aib,
X3 represents Gln, X14 represents Lys, wherein the —NH$_2$ side chain group is functionalized, particularly by (S)-4-Carboxy-4-henicosanoylamino-butyryl- and (S)-4-Carboxy-4-octadecanoylamino-butyryl-;
X15 represents Asp, X16 represents an amino acid residue selected from Lys and Glu,
X17 represents an amino acid residue selected from Arg and Glu, X18 represents an amino acid residue selected from Ala and Arg,
X20 represents an amino acid residue selected from Gln and Lys,
X21 represents an amino acid residue selected from Asp and Leu,
X28 represents Ala,
X29 represents an amino acid residue selected from Gly and D-Ala,
X35 represents Ala,
X39 is Ser,
X40 is absent.

In one embodiment, the invention provides a peptidic compound having the formula (I):

  (I), wherein Z is a peptide moiety having the formula (IIa)

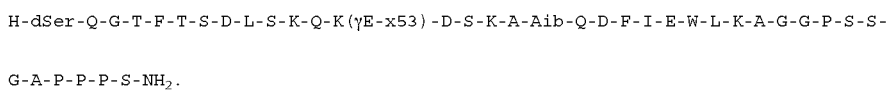

In another embodiment, the invention provides a peptidic compound having the formula (I):

  (I), wherein Z is a peptide moiety having the formula (IIb)

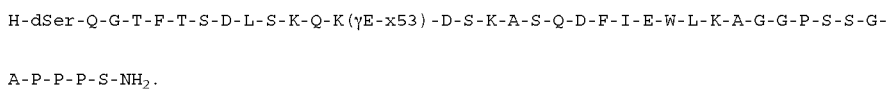

In another embodiment, the invention provides a peptidic compound having the formula (I):

  (I), wherein Z is a peptide moiety having the formula (IIc)

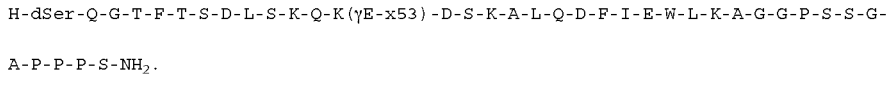

In another embodiment, the invention provides a peptidic compound having the formula (I):

  (I), wherein Z is a peptide moiety having the formula (IId)

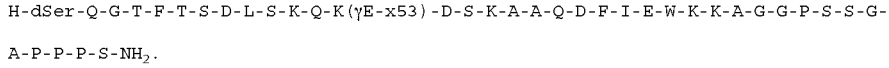

Specific examples of peptidic compounds of the invention are the compounds of SEQ ID NO: 4-181, as well as salts and solvates thereof.

Further specific examples of peptidic compounds of the invention are the compounds of SEQ ID NO: 4-181 and 196-223 as well as salts and solvates thereof.

Further specific examples of peptidic compounds of the invention are the compounds of SEQ ID NO: 7, 11-13, 22, 24-31, 34-39, 44-48, 86, 97, 123-124, 130-159, 164, 166, 173-176, as well as salts and solvates thereof.

Further specific examples of peptidic compounds of formula (I) are the compounds of SEQ ID NO: 7, 11-13, 22, 24-31, 34-39, 44-48, 86, 97, 123-124, 130-159, 164, 166, 173-176, 196-223, 226-229 as well as salts and solvates thereof.

In some embodiments, the compound of the invention is selected from the group consisting of SEQ ID NOs.: 25, 31, 133, 148, 153, 155 and 158. In other embodiments, the compound of the invention is selected from the group consisting of SEQ ID NOs.: 209, 210, 211, 212 and 213.

According to one particular embodiment, the compound of the invention is represented by SEQ ID NO.: 97 (see Table 10). In another particular embodiment, the compound of formula (I) is represented by SEQ ID NO.: 24 (see Table 10).

In certain embodiments, i.e. when the compound of formula (I) comprises genetically encoded amino acid residues, the invention further provides a nucleic acid (which may be DNA or RNA) encoding said compound, an expression vector comprising such a nucleic acid, and a host cell containing such a nucleic acid or expression vector.

In a further aspect, the present invention provides a composition comprising a compound of the invention in admixture with a carrier. In preferred embodiments, the composition is a pharmaceutically acceptable composition and the carrier is a pharmaceutically acceptable carrier. The compound of the invention may be in the form of a salt, e.g. a pharmaceutically acceptable salt or a solvate, e.g. a hydrate. In still a further aspect, the present invention provides a composition for use in a method of medical treatment, particularly in human medicine.

In certain embodiments, the nucleic acid or the expression vector may be used as therapeutic agents, e.g. in gene therapy.

The compounds of formula (I) are suitable for therapeutic application without an additionally therapeutically effective agent. In other embodiments, however, the compounds are used together with at least one additional therapeutically active agent, as described in "combination therapy".

The compounds of formula (I) are particularly suitable for the treatment or prevention of diseases or disorders caused by, associated with and/or accompanied by disturbances in carbohydrate and/or lipid metabolism, e.g. for the treatment or prevention of hyperglycemia, type 2 diabetes, impaired glucose tolerance, type 1 diabetes, obesity and metabolic syndrome. Further, the compounds of the invention are particularly suitable for the treatment or prevention of degenerative diseases, particularly neurodegenerative diseases.

The compounds described find use, inter alia, in preventing weight gain or promoting weight loss. By "preventing" is meant inhibiting or reducing when compared to the absence of treatment, and is not necessarily meant to imply complete cessation of a disorder.

The compounds of the invention may cause a decrease in food intake and/or increase in energy expenditure, resulting in the observed effect on body weight.

Independently of their effect on body weight, the compounds of the invention may have a beneficial effect on circulating cholesterol levels, being capable of improving lipid levels, particularly LDL, as well as HDL levels (e.g. increasing HDL/LDL ratio).

Thus, the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for treatment and prevention of the metabolic syndrome, diabetes, hypertension, atherogenic dyslipidemia, atherosclerosis, arteriosclerosis, coronary heart disease, or stroke. Their effects in these conditions may be as a result of or associated with their effect on body weight, or may be independent thereof.

Preferred medical uses include delaying or preventing disease progression in type 2 diabetes, treating metabolic syndrome, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as X-ray, CT- and NMR-scanning.

Further preferred medical uses include treatment or prevention of degenerative disorders, particularly neurodegenerative disorders such as Alzheimer's disease, Parkinson's disease, Huntington's disease, ataxia, e.g. spinocerebellar ataxia, Kennedy disease, myotonic dystrophy, Lewy body dementia, multi-systemic atrophy, amyotrophic lateral sclerosis, primary lateral sclerosis, spinal muscular atrophy, prion-associated diseases, e.g. Creutzfeldt-Jacob disease, multiple sclerosis, telangiectasia, Batten disease, corticobasal degeneration, subacute combined degeneration of spinal cord, Tabes dorsalis, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral β-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), Lysozyme amyloidosis, Fibrinogen amyloidosis, Dialysis amyloidosis, Inclusion body myositis/myopathy, Cataracts, Retinitis pigmentosa with rhodopsin mutations, medullary thyroid carcinoma, cardiac atrial amyloidosis, pituitary prolactinoma, Hereditary lattice corneal dystrophy, Cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM).

DETAILED DESCRIPTION OF THE INVENTION

Definitions

The amino acid sequences of the present invention contain the conventional one letter and three letter codes for naturally occurring amino acids, as well as generally accepted three letter codes for other amino acids, such as Aib (α-aminoisobutyric acid), Orn (ornithin), Dab (2,4-diamino butyric acid), Dap (2,3-diamino propionic acid), Nle (norleucine), GABA (γ-aminobutyric acid) or Ahx (ε-aminohexanoic acid).

The term "native exendin-4" refers to native exendin-4 having the sequence HGEGTFTSDLSKQMEEEAVR-LFIEWLKNGGPSSGAPPPS-NH$_2$ (SEQ ID NO: 1).

The invention provides peptidic compounds as defined above.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds preferably comprise a backbone sequence of 39-40 amino carboxylic acids.

The peptidic compounds may be functionalized (covalently linked) with chemical moieties at their N-terminus, C-terminus and at least one side chain. The N-terminus of the peptidic compound may be unmodified, i.e. an NH$_2$ group or a mono- or bisfunctionalized NH$_2$ group.

At the C-terminus, the peptidic compounds may be unmodified, i.e. have a OH group or be modified, e.g. with functionalized OH group or an NH$_2$ group or a monofunctionalized or bisfunctionalized NH$_2$ group as described above (see R)

The term "alkyl", as used herein, refers to saturated, monovalent hydrocarbon radicals. The alkyl groups can be linear, i.e. straight-chain, or branched.

The term "alkanediyl" or "alkylene", as used herein, refers to saturated, divalent hydrocarbon radicals. As far as applicable, the preceding explanations regarding alkyl groups apply correspondingly to alkanediyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—, —CH$_2$—C(CH$_3$)$_2$—.

The term "cycloalkyl", as used herein, unless otherwise indicated, refers to a monovalent radical of a saturated or partially saturated hydrocarbon ring system, which can be monocyclic. Examples of cycloalkyl groups are cyclopropyl, cyclobutyl, cyclopentyl, cyclohexyl, cycloheptyl and cyclooctyl.

The term "heterocycloalkyl" or "heterocyclyl", as used herein unless otherwise indicated, refers to a cycloalkyl as defined above, in which 1, 2 or 3 carbon atoms are replaced by nitrogen, oxygen or sulfur atoms, provided that the heterocycloalkyl system is stable and suitable as a subgroup for the desired purpose of the compound of the formula (I) such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 2, in another embodiment 1, wherein the ring heteroatoms can be identical or different. The heterocycloalkyl group can be attached by any ring carbon atom or saturated ring nitrogen atom.

Halogen is fluorine, chlorine, bromine or iodine.

The peptidic compounds of the present invention may have unmodified side chains or carry at least one modification at one of the side chains.

For the avoidance of doubt, in the definitions provided herein, it is generally intended that the sequence of the peptidic moiety (II) differs from native exendin-4 at least at one of those positions which are stated to allow variation. Amino acids within the peptide moiety (II) can be considered to be numbered consecutively from 0 to 40 in the conventional N-terminal to C-terminal direction. Reference to a "position" within peptidic moiety (II) should be constructed accordingly, as should reference to positions within native exendin-4 and other molecules.

The amino acid residues at position 14 and optionally at position 40, having a side chain with an —NH$_2$ group, e.g. Lys, Orn, Dab or Dap are conjugated to a functional group, e.g. acyl groups. Thus, one or more selected amino acids of the peptides in the present invention may carry a covalent attachment at their side chains. In some cases those attachments may be lipophilic. These lipophilic side chain attachments have the potential to reduce in vivo clearance of the peptides thus increasing their in vivo half-lives.

The lipophilic attachment may consist of a lipophilic moiety which can be a branched or unbranched, aliphatic or unsaturated acyclic moiety and/or a cyclic moiety selected from one or several aliphatic or unsaturated homocycles or heterocycles, aromatic condensed or non-condensed homocycles or heterocycles, ether linkages, unsaturated bonds and substituents, e.g. hydroxy and/or carboxy groups. The lipophilic moiety may be attached to the peptide either by alkylation, reductive amination or by an amide bond or a sulfonamide bond in case of amino acids carrying an amino group at their side chain, an ester bond in case of amino acids carrying a hydroxy group at their side chain or thioether or thioester linkages in case of amino acids carrying a thiol group at their side chain or it may be attached to a modified side chain of an amino acid thus allowing the introduction of a lipophilic moiety by click-chemistry or Michael-addition.

Nonlimiting examples of lipophilic moieties that can be attached to amino acid side chains include fatty acids, e.g. C$_{8-30}$ fatty acids such as palmitic acid, myristic acid, stearic acid and oleic acid, and/or cyclic groups as described above or derivatives thereof.

There might be one or several linkers between the amino acid of the peptide and the lipophilic attachment. Nonlimiting examples of those linkers are β-alanine, γ-glutamic acid, γ-aminobutyric acid and/or ε-aminohexanoic acid or dipeptides, such as β-Ala-β-Ala and/or γ-Glu-γ-Glu in all their stereo-isomer forms (S and R enantiomers).

Thus, one nonlimiting example of a side chain attachment is palmitic acid which is covalently linked to the α-amino group of glutamic acid forming an amide bond. The γ-carboxy group of this substituted glutamic acid can form an amide bond with the side chain amino group of a lysine within the peptide.

In a further aspect, the present invention provides a composition comprising a compound of the invention as described herein, or a salt or solvate thereof, in admixture with a carrier.

The invention also provides the use of a compound of the present invention for use as a medicament, particularly for the treatment of a condition as described below.

The invention also provides a composition wherein the composition is a pharmaceutically acceptable composition, and the carrier is a pharmaceutically acceptable carrier.

Peptide Synthesis

The skilled person is aware of a variety of different methods to prepare peptides that are described in this invention. These methods include but are not limited to synthetic approaches and recombinant gene expression. Thus, one way of preparing these peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the peptides of the present invention is solid phase synthesis on a suitable resin. Solid phase peptide synthesis is a well established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support carrying a cleavable linker. This solid support can be any polymer that allows coupling of the initial amino acid, e.g. a trityl resin, a chlorotrityl resin, a Wang resin or a Rink resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyluronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc.

Usually, reactive side chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999).

In some cases it might be desirable to have side chain protecting groups that can selectively be removed while other side chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side chain functionalities are protected with acid labile protecting groups, the ivDde ([1-(4,4-dimethyl-2,6-dioxocyclohex-1-ylidene)-3-methylbutyl) group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids.

Finally the peptide is cleaved from the resin. This can be achieved by using King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Potency

As used herein, the term "potency" or "in vitro potency" is a measure for the ability of a compound to activate the receptors for GLP-1 or glucagon in a cell-based assay. Numerically, it is expressed as the "EC50 value", which is the effective concentration of a compound that induces a half maximal increase of response (e.g. formation of intracellular cAMP) in a dose-response experiment.

Therapeutic Uses

According to one aspect, the compounds of the invention are for use in medicine, particularly human medicine.

The compounds of the invention are agonists for the receptors for GLP-1 and for glucagon (e.g. "dual agonists") and may provide an attractive option for targeting the metabolic syndrome by allowing simultaneous treatment of obesity and diabetes.

Metabolic syndrome is a combination of medical disorders that, when occurring together, increase the risk of developing type 2 diabetes, as well as atherosclerotic vascular disease, e.g. heart disease and stroke. Defining medical parameters for the metabolic syndrome include diabetes mellitus, impaired glucose tolerance, raised fasting glucose, insulin resistance, urinary albumin secretion, central obesity, hypertension, elevated triglycerides, elevated LDL cholesterol and reduced HDL cholesterol.

Obesity is a medical condition in which excess body fat has accumulated to the extent that it may have an adverse effect on health and life expectancy and due to its increasing prevalence in adults and children it has become one of the leading preventable causes of death in modern world. It increases the likelihood of various other diseases, including heart disease, type 2 diabetes, obstructive sleep apnoe, certain types of cancer, as well as osteoarthritis, and it is most commonly caused by a combination of excess food intake, reduced energy expenditure, as well as genetic susceptibility.

Diabetes mellitus, often simply called diabetes, is a group of metabolic diseases in which a person has high blood sugar levels, either because the body does not produce enough insulin, or because cells do not respond to the insulin that is produced. The most common types of diabetes are: (1) type 1 diabetes, where the body fails to produce insulin; (2) type 2 diabetes, where the body fails to use insulin properly, combined with an increase in insulin deficiency over time, and (3) gestational diabetes, where women develop diabetes due to their pregnancy. All forms of diabetes increase the risk of long-term complications, which typically develop after many years. Most of these long-term complications are based on damage to blood vessels and can be divided into the two categories "macrovascular" disease, arising from atherosclerosis of larger blood vessels and "microvascular" disease, arising from damage of small blood vessels. Examples for macrovascular disease conditions are ischemic heart disease, myocardial infarction, stroke and peripheral vascular disease. Examples for microvascular diseases are diabetic retinopathy, diabetic nephropathy, as well as diabetic neuropathy.

The receptors for GLP-1 and glucagon are both members of the family B of G-protein coupled receptors. They are highly related to each other and share not only a significant level of sequence identity, but have also similar mechanisms of ligand recognition and intracellular signaling pathways.

Similarly, the peptides GLP-1 and glucagon are homologous to each other, with similar length and regions of high sequence identity. Both are produced from a common precursor, preproglucagon, which is differentially processed in a tissue-specific manner to yield e.g. GLP-1 in intestinal endocrine cells and glucagon in alpha cells of pancreatic islets.

The incretin hormone GLP-1 is secreted by intestinal endocrine cells in response to food and enhances meal-stimulated insulin secretion. Evidence suggests that GLP-1 secretion is reduced in subjects with impaired glucose tolerance or type 2 diabetes, whereas responsiveness to GLP-1 is still preserved in these patients. Thus, targeting of the GLP-1 receptor with suitable agonists offers an attractive approach for treatment of metabolic disorders, including diabetes. The receptor for GLP-1 is distributed widely, being found mainly in pancreatic islets, brain, heart, kidney and the gastrointestinal tract. In the pancreas, GLP-1 acts in a strictly glucose-dependent manner by increasing secretion of insulin from beta cells. This glucose-dependency shows that activation of GLP-1 receptors is unlikely to cause hypoglycemia.

At the beta cell level, GLP-1 has been shown to promote glucose sensitivity, neogenesis, proliferation, transcription of proinsulin and hypertrophy, as well as antiapoptosis. Other relevant effects of GLP-1 beyond the pancreas include delayed gastric emptying, increased satiety, decreased food intake, reduction of body weight, as well as neuroprotective and cardioprotective effects. In patients with type 2 diabetes, such extrapancreatic effects could be particularly important considering the high rates of comorbidities like obesity and cardiovascular disease.

Glucagon is a 29-amino acid peptide hormone that is produced by pancreatic alpha cells and released into the bloodstream when circulating glucose is low. An important physiological role of glucagon is to stimulate glucose output in the liver, which is a process providing the major counterregulatory mechanism for insulin in maintaining glucose homeostasis in vivo.

Glucagon receptors are however also expressed in extrahepatic tissues such as kidney, heart, adipocytes, lymphoblasts, brain, retina, adrenal gland and gastrointestinal tract, suggesting a broader physiological role beyond glucose homeostasis. Accordingly, recent studies have reported that glucagon has therapeutically positive effects on energy management, including stimulation of energy expenditure and thermogenesis, accompanied by reduction of food intake and body weight loss. Altogether, stimulation of glucagon receptors might be useful in the treatment of obesity and the metabolic syndrome.

Oxyntomodulin is a 37-amino acid peptide hormone consisting of glucagon with an eight amino acids encompassing C-terminal extension. Like GLP-1 and glucagon, it is preformed in preproglucagon and cleaved and secreted in a tissue-specific manner by endocrinal cells of the small bowel. Oxyntomodulin is known to stimulate both, the receptors for GLP-1 and glucagon and is therefore the prototype of a dual agonist.

As GLP-1 is known for its anti-diabetic effects, GLP-1 and glucagon are both known for their food intake-suppressing effects and glucagon is also a mediator of additional energy expenditure, it is conceivable that a combination of the activities of the two hormones in one molecule can yield a powerful medication for treatment of the metabolic syndrome and in particular its components diabetes and obesity.

Accordingly, the compounds of the invention may be used for treatment of glucose intolerance, insulin resistance, pre-diabetes, increased fasting glucose, type 2 diabetes, hypertension, dyslipidemia, arteriosclerosis, coronary heart disease, peripheral artery disease, stroke or any combination of these individual disease components.

In addition, they may be used for control of appetite, feeding and calory intake, increase of energy expenditure, prevention of weight gain, promotion of weight loss, reduction of excess body weight and altogether treatment of obesity, including morbid obesity.

Further disease states and health conditions which could be treated with the compounds of the invention are obesity-linked inflammation, obesity-linked gallbladder disease and obesity-induced sleep apnea.

Although all these conditions could be associated directly or indirectly with obesity, the effects of the compounds of the invention may be mediated in whole or in part via an effect on body weight, or independent thereof.

Further, diseases to be treated are neurodegenerative diseases such as Alzheimer's disease or Parkinson's disease, or other degenerative diseases as described above.

Pharmaceutical Compositions

The term "pharmaceutical composition" indicates a mixture containing ingredients that are compatible when mixed and which may be administered. A pharmaceutical composition may include one or more medicinal drugs. Additionally, the pharmaceutical composition may include carriers, buffers, acidifying agents, alkalizing agents, solvents, adjuvants, tonicity adjusters, emollients, expanders, preservatives, physical and chemical stabilizers e.g. surfactants, antioxidants and other components, whether these are considered active or inactive ingredients. Guidance for the skilled in preparing pharmaceutical compositions may be found, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical Excipients, PhP, May 2013 update.

The exendin-4 peptide derivatives of the present invention, or salts thereof, are administered in conjunction with an acceptable pharmaceutical carrier, diluent, or excipient as part of a pharmaceutical composition. A "pharmaceutically acceptable carrier" is a carrier which is physiologically acceptable (e.g. physiologically acceptable pH) while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical excipients, PhP, May 2013 update. One exemplary pharmaceutically acceptable carrier is physiological saline solution.

In one embodiment carriers are selected from the group of buffers (e.g. citrate/citric acid), acidifying agents (e.g. hydrochloric acid), alkalizing agents (e.g. sodium hydroxide), preservatives (e.g. phenol), co-solvents (e.g. polyethylene glycol 400), tonicity adjusters (e.g. mannitol), stabilizers (e.g. surfactant, antioxidants, amino acids).

Concentrations used are in a range that is physiologically acceptable.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

The term "pharmaceutically acceptable salt" means salts of the compounds of the invention which are safe and effective for use in mammals. Pharmaceutically acceptable salts may include, but are not limited to, acid addition salts and basic salts. Examples of acid addition salts include chloride, sulfate, hydrogen sulfate, (hydrogen)phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water.

In the pharmaceutical composition, the exendin-4 derivative can be in monomeric or oligomeric form.

The term "therapeutically effective amount" of a compound refers to a nontoxic but sufficient amount of the compound to provide the desired effect. The amount of a compound of the formula I necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation For example the "therapeutically effective amount" of a compound of the formula (I) is about 0.01 to 50 mg/dose, preferably 0.1 to 10 mg/dose.

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the nature and severity of the condition to be treated and on the nature of the compound of formula I used in each case.

Suitable pharmaceutical compositions may be in the form of separate units, for example capsules, tablets and powders in vials or ampoules, each of which contains a defined amount of the compound; as powders or granules; as solution or suspension in an aqueous or nonaqueous liquid; or as an oil-in-water or water-in-oil emulsion. It may be provided in single or multiple dose injectable form, for example in the form of a pen. The compositions may, as already mentioned, be prepared by any suitable pharmaceutical method which includes a step in which the active ingredient and the carrier (which may consist of one or more additional ingredients) are brought into contact.

In certain embodiments the pharmaceutical composition may be provided together with a device for application, for example together with a syringe, an injection pen or an autoinjector. Such devices may be provided separate from a pharmaceutical composition or prefilled with the pharmaceutical composition.

Combination Therapy

The compounds of the present invention, dual agonists for the GLP-1 and glucagon receptors, can be widely combined with other pharmacologically active compounds, such as all drugs mentioned in the Rote Liste 2012 and/or the Rote Liste 2013, e.g. with all antidiabetics mentioned in the Rote Liste 2012, chapter 12, and/or the Rote Liste 2013, chapter 12, all weight-reducing agents or appetite suppressants mentioned in the Rote Liste 2012, chapter 1, and/or the Rote Liste 2013, chapter 1, all lipid-lowering agents mentioned in the Rote Liste 2012, chapter 58, and/or the Rote Liste 2013, chapter 58, all antihypertensives and nephroprotectives, mentioned in the Rote Liste 2012 and/or the Rote Liste 2013, or all diuretics mentioned in the Rote Liste 2012, chapter 36, and/or the Rote Liste 2013, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Most of the active ingredients mentioned hereinafter are disclosed in the USP Dictionary of USAN and International Drug Names, US Pharmacopeia, Rockville 2011.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargine/Lantus®, 270-330 U/mL of insulin glargine (EP 2387989 A), 300 U/mL of insulin glargine (EP 2387989 A), Glulisin/Apidra®, Detemir/Levemir®, Lispro/Humalog®/Liprolog®, Degludec/DegludecPlus, Aspart, basal insulin and analogues (e.g. LY-2605541, LY2963016, NN1436), PEGylated insulin Lispro, Humulin®, Linjeta, SuliXen®, NN1045, Insulin plus Symlin, PE0139, fast-acting and short-acting insulins (e.g. Linjeta, PH20, NN1218, HinsBet), (APC-002)hydrogel, oral, inhalable, transdermal and sublingual insulins (e.g. Exubera®, Nasulin®, Afrezza, Tregopil, TPM 02, Capsulin, Oral-Iyn®, Cobalamin® oral insulin, ORMD-0801, NN1953, NN1954, NN1956, VIAtab, Oshadi oral insulin). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650/AC-2993, Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

DPP-4 inhibitors, for example: Alogliptin/Nesina, Trajenta/Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Galvus/Vildagliptin, Anagliptin, Gemigliptin, Teneligliptin, Melogliptin, Trelagliptin, DA-1229, Omarigliptin/MK-3102, KM-223, Evogliptin, ARI-2243, PBL-1427, Pinoxacin.

SGLT2 inhibitors, for example: Invokana/Canaglifozin, Forxiga/Dapagliflozin, Remoglifozin, Sergliflozin, Empagliflozin, Ipragliflozin, Tofogliflozin, Luseogliflozin, LX-4211, Ertuglifozin/PF-04971729, RO-4998452, EGT-0001442, KGA-3235/DSP-3235, LIK066, SBM-TFC-039), Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597, ZYG-19, DS-8500), GPR40 agonists (e.g. Fasiglifam/TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329, GKM-001), inhibitors of DGAT (e.g. LCQ-908), inhibitors of protein tyrosinephosphatase 1 (e.g. Trodusquemine), inhibitors of glucose-6-phosphatase, inhibitors of fructose-1, 6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists, SGLT-1 inhibitors (e.g. LX-2761).

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. Cholestyramine), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:

Further gastrointestinal peptides such as Peptide YY 3-36 (PYY3-36) or analogues thereof, pancreatic polypeptide (PP) or analogues thereof.

Glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a tablet or capsule, or separately in two identical or different formulations, for example as so-called kit-of-parts.

LEGENDS TO THE FIGURES

FIG. 1. Effect of s.c. administration of compound SEQ ID NO: 97 and comparators on gastric emptying and intestinal passage in female NMRI-mice. Data are mean±SEM. "*" indicates statistical significance versus vehicle, "#" versus comparators, respectively.
a) Effect of SEQ ID NO: 97 and Liraglutide (all 0.02 mg/kg, s.c.) on remaining gastric contents (as indicator for gastric emptying)
b) Effect of SEQ ID NO: 97 and Liraglutide all 0.02 mg/kg, s.c., on small intestinal motility
c) Effect of SEQ ID NO: 97, at 0.02 and 0.002 mg/kg, s.c., on remaining gastric contents (as indicator for gastric emptying)
d) Effect of SEQ ID NO: 97, at 0.02 and 0.002 mg/kg, s.c., on small intestinal motility FIG. 2. Effect of SEQ ID NO: 97, 0.1 and 0.01 mg/kg, s.c., on 22-hours food intake in female NMRI-mice. Data are mean±SEM. *p<0.05.

Figure 3:
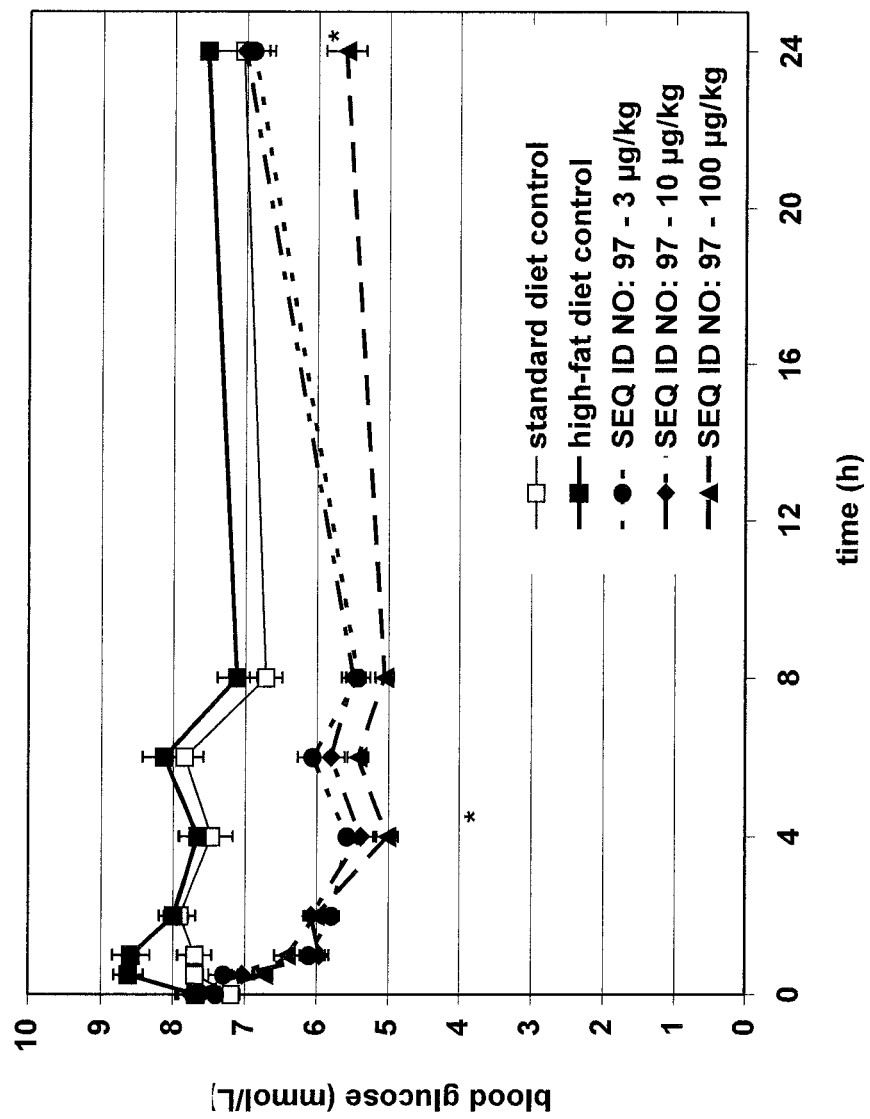

FIG. 3. Acute effect of s.c. administration of compound SEQ ID NO: 97 on blood glucose in female diet-induced obese C57BL/6NCrI mice (9 months on high-fat diet). Data are mean±SEM. *p<0.05.

Figure 4:
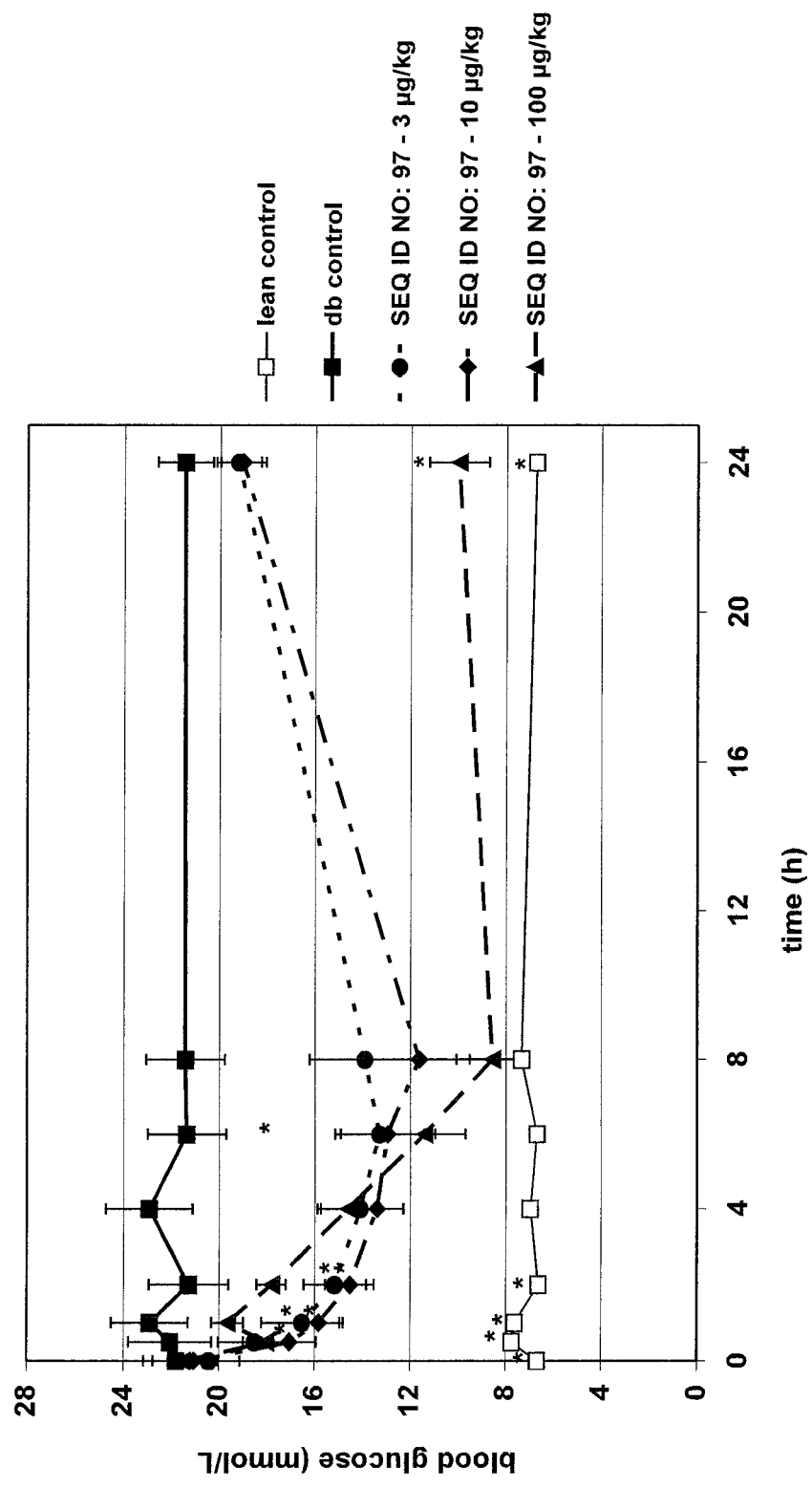

FIG. 4. Acute effect of s.c. administration of compound SEQ ID NO: 97 on blood glucose in female leptin-receptor deficient diabetic db/db mice. Data are mean±SEM. *p<0.05.

Figure 5:
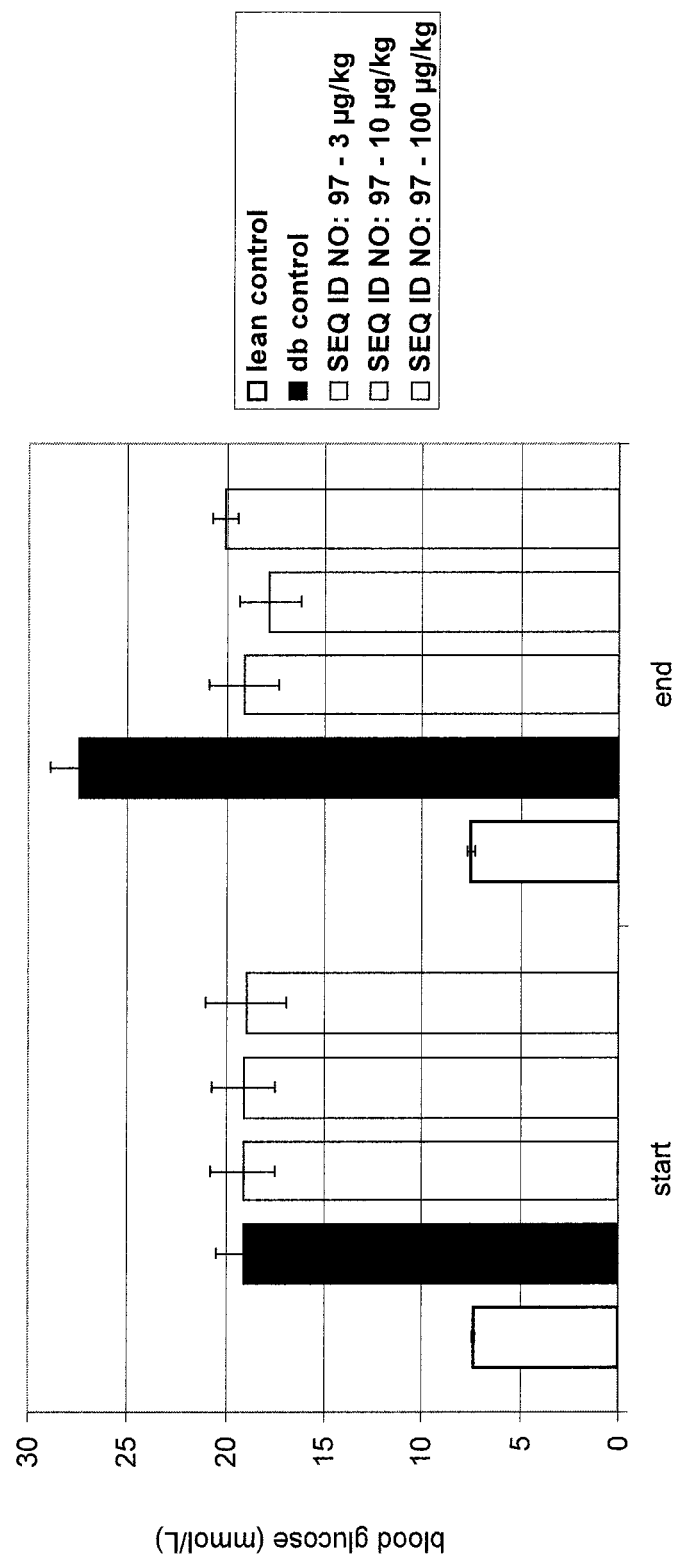

FIG. 5. Glucose level before and after 4 weeks of subcutaneous treatment with SEQ ID NO: 97 in female leptin-receptor deficient diabetic db/db mice. Data are mean±SEM.

Figure 6:
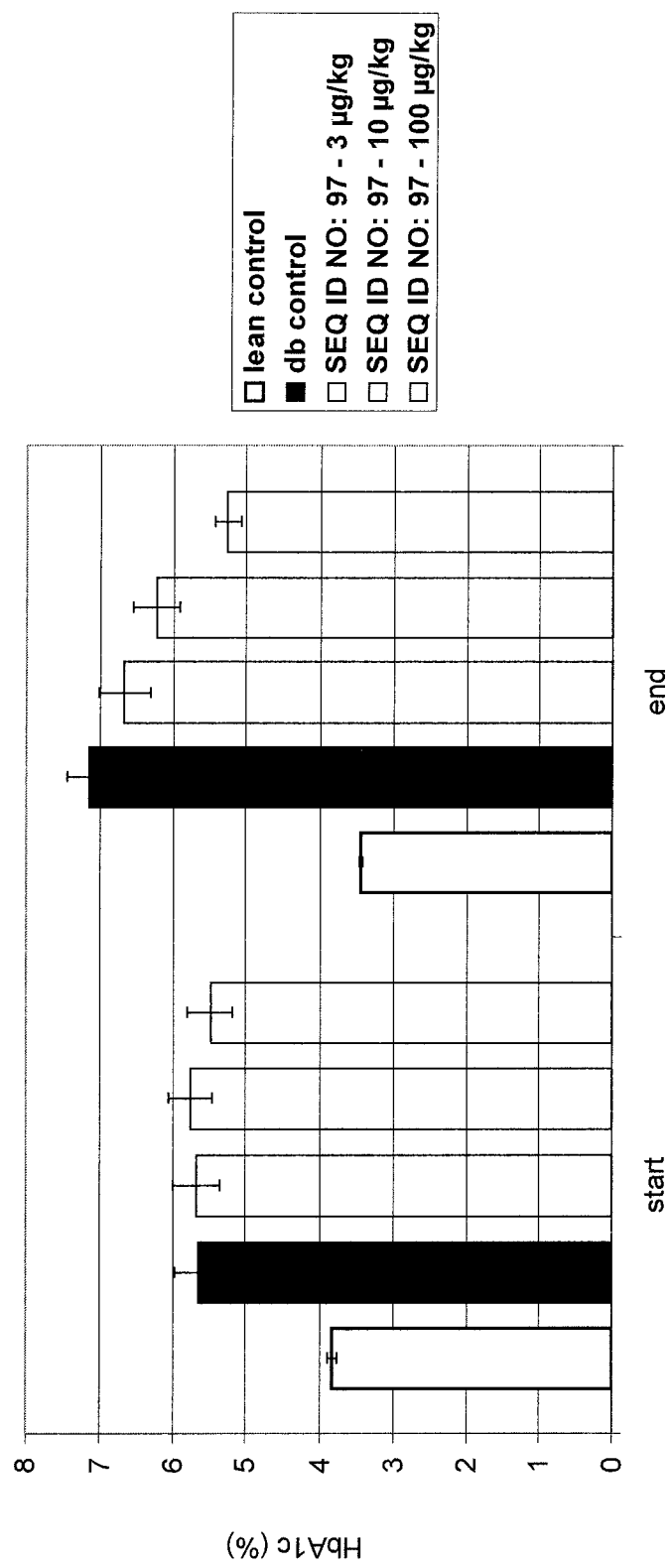

FIG. 6. HbA1c level before and after 4 weeks of subcutaneous treatment with SEQ ID NO: 97 in female leptin-receptor deficient diabetic db/db mice. Data are mean±SEM.

Figure 7:
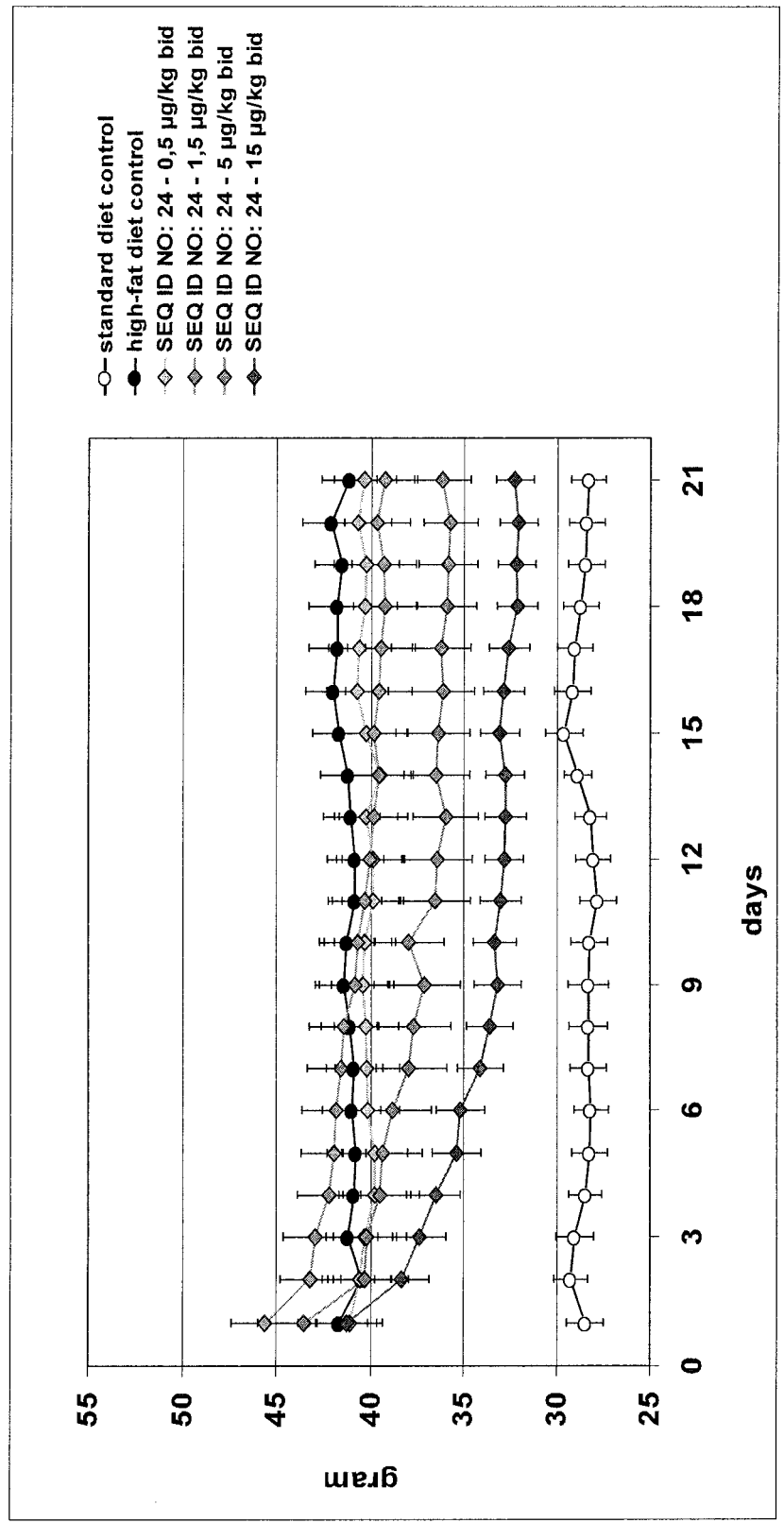

FIG. 7. Body weight development during 3 weeks of subcutaneous treatment with SEQ ID NO: 24 in male high-fat fed C57BL/6N CrI mice. Data are mean±SEM.

Figure 8:
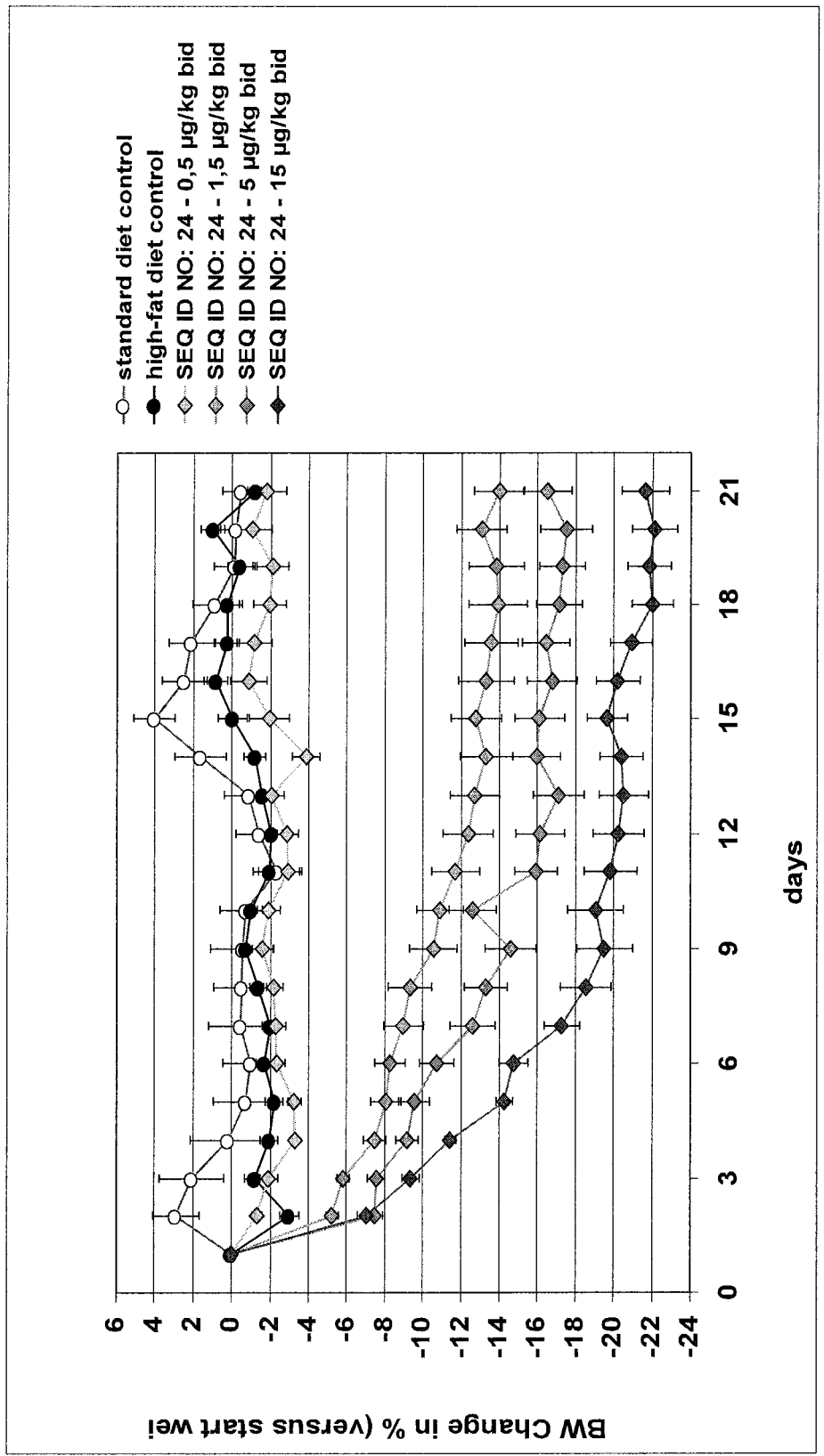

FIG. 8. Relative body weight change in % during 3 weeks of subcutaneous treatment with SEQ ID NO: 24 in male high-fat fed C57BL/6N CrI mice. Data are mean±SEM.

Figure 9:
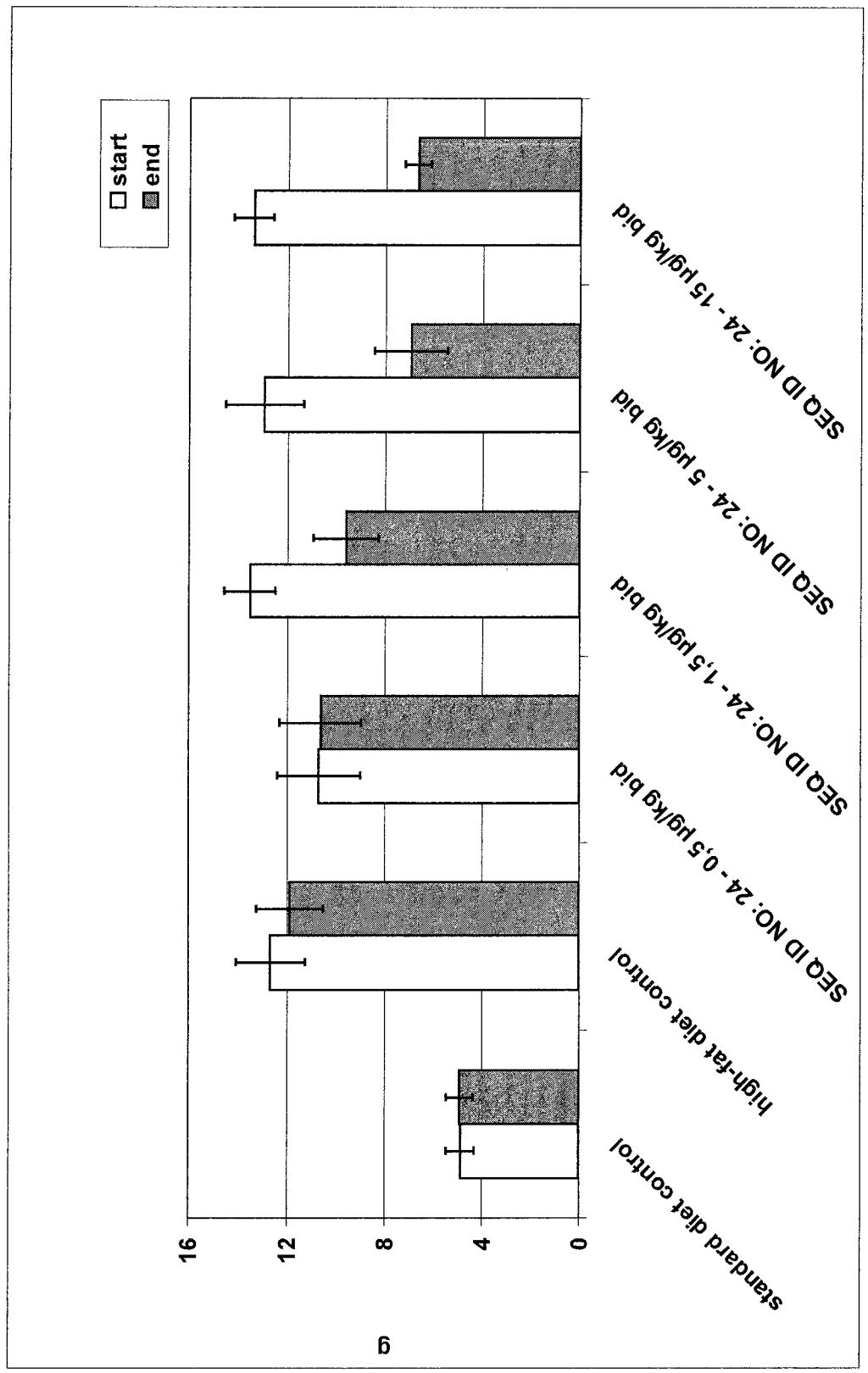

FIG. 9. Determination of total fat mass measured by nuclear magnetic resonance (NMR) using a Bruker minispec, before and after 3 weeks of treatment with SEQ ID NO: 24 in male high-fat fed C57BL/6N CrI mice. Data are mean±SEM.

Figure 10:
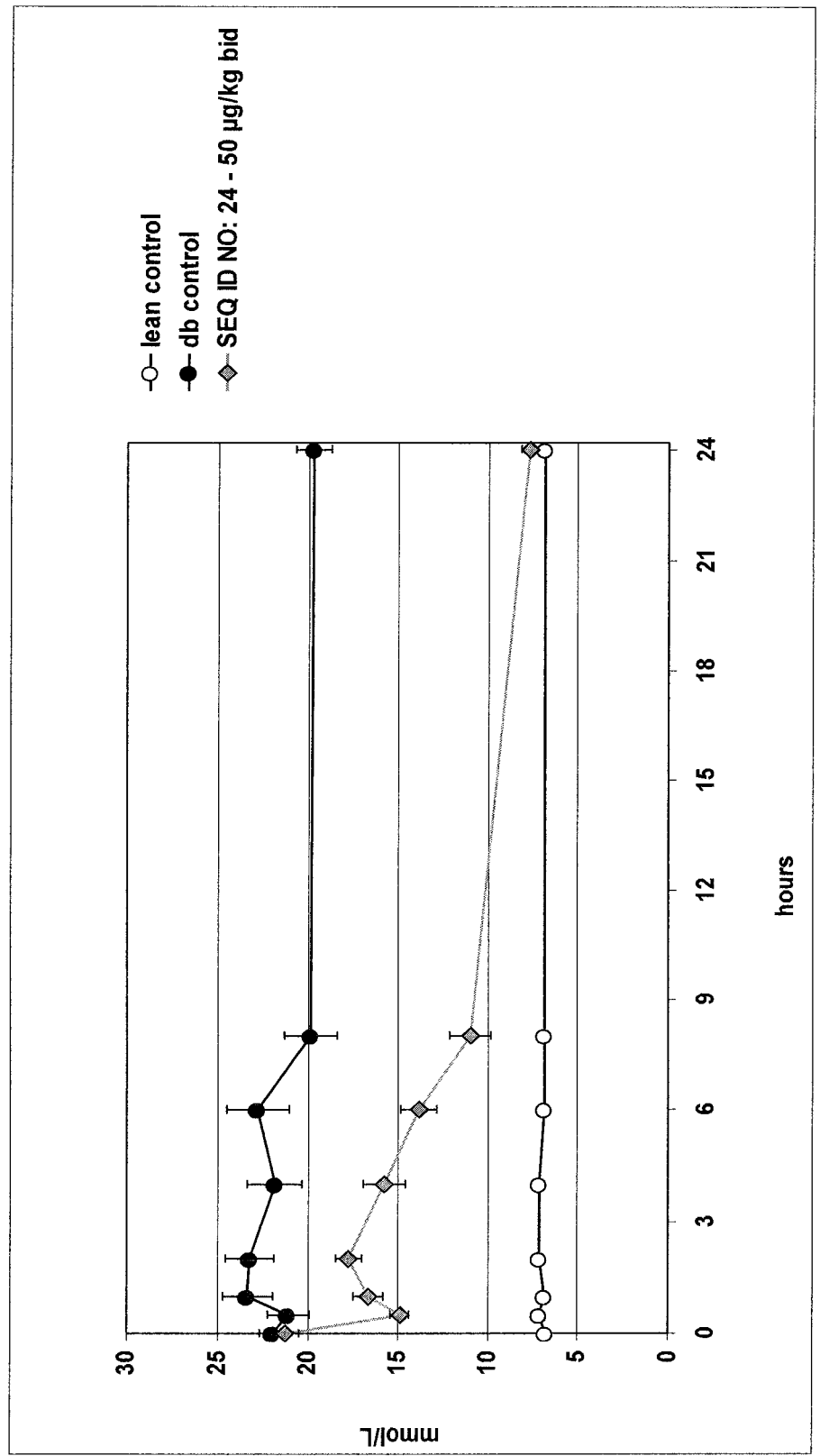

FIG. 10. Acute effect of s.c. administration of compound SEQ ID NO: 24 on blood glucose in female leptin-receptor deficient diabetic db/db mice. Data are mean±SEM.

Figure 11:
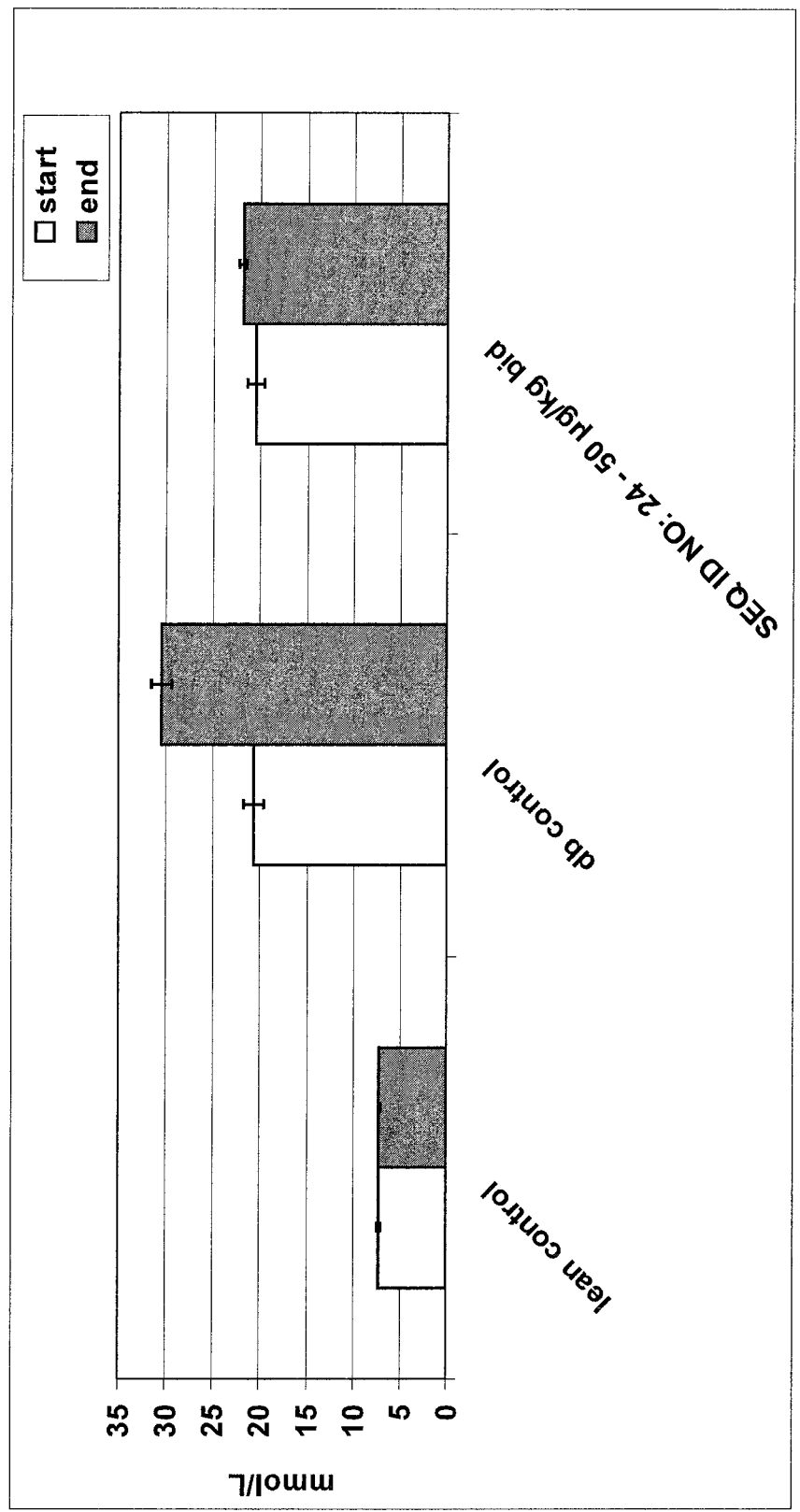

FIG. 11. Glucose level before and after 4 weeks of subcutaneous treatment with SEQ ID NO: 24 in female leptin-receptor deficient diabetic db/db mice. Data are mean±SEM.

Figure 12:
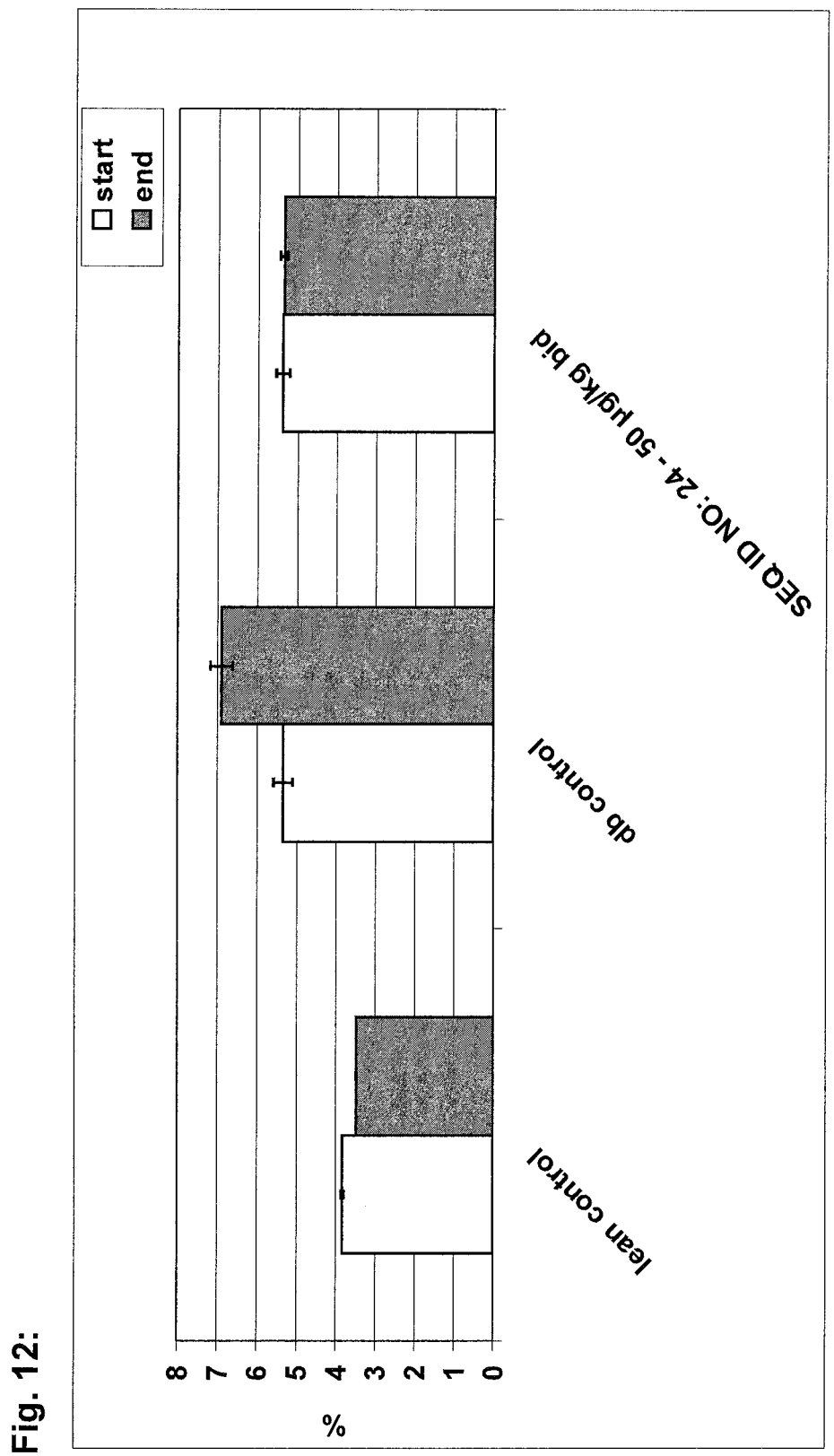

FIG. 12. HbA1c level before and after 4 weeks of subcutaneous treatment with SEQ ID NO: 24 in female leptin-receptor deficient diabetic db/db mice. Data are mean±SEM.

METHODS

Abbreviations employed are as follows:
ivDde: 1-(4,4-dimethyl-2,6-dioxocyclohexylidene)$_3$-methyl-butyl
Dde: 1-(4,4-dimethyl-2,6-dioxocyclohexylidene)-ethyl
TFA: trifluoroacetic acid
BOP benzotriazol-1-yl-oxy-tris-(dimethylamino)-phosphonium hexafluorophosphate
HBTU 2-(1H-benzotriazol-1-yl)-1,1,3,3-tetramethyluronium hexafluorophosphate
HATU O-(7-azabenzotriazol-1-yl)-N,N,N',N'-tetramethyluronium hexafluorophosphate
DIC N,N'-diisopropylcarbodiimide
HOBt 1-hydroxybenzotriazol
DMF dimethyl formamide
EDT ethanedithiol
HPLC High Performance Liquid Chromatography
Boc tert-butyloxycarbonyl
Fmoc fluorenyloxycarbonyl
PEG Polyethylene Glycol
HTRF Homogenous Time Resolved Fluorescence
BSA bovine serum albumin
FBS fetal bovine serum
DMEM Dulbecco's modified Eagle's medium
PBS phosphate buffered saline
HEPES 2-[4-(2-hydroxyethyl)piperazin-1-yl]ethanesulfonic acid
IBMX 3-Isobutyl-1-methylxanthine
General Synthesis of Peptidic Compounds
Materials:

Different Rink-Amide resins (4-(2',4'-Dimethoxyphenyl-Fmoc-aminomethyl)-phenoxyacetamido-norleucylaminomethyl resin, Merck Biosciences; 4-[(2,4-Dimethoxphenyl)(Fmoc-amino)methyl]phenoxy acetamido methyl resin, Agilent Technologies) were used for the synthesis of peptide amides with loadings in the range of 0.3-0.4 mmol/g. Suppliers were Merck Biosciences and Agilent Technologies. From the same suppliers 2-chloro-trityl-chloride polystyrene resins with loadings up to 1.4 mmol/g were purchased and used for the synthesis of peptide acids.

Fmoc protected natural amino acids were purchased from Protein Technologies Inc., Senn Chemicals, Merck Biosciences, Novabiochem, Iris Biotech or Bachem. The following standard amino acids were used throughout the syntheses: Fmoc-L-Ala-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Lys(ivDde)-OH, Fmoc-Aib-OH, Fmoc-D-Ser(tBu)-OH, Fmoc-D-Ala-OH, Boc-L-His(Boc)-OH (available as toluene solvate) and Boc-L-His(Trt)-OH.

The solid phase peptide syntheses were performed on a Prelude Peptide Synthesizer (Protein Technologies Inc) using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

In cases where a Lys-side chain was modified, Fmoc-L-Lys(ivDde)-OH was used in the corresponding position. After completion of the synthesis, the ivDde group was removed according to a modified literature procedure (S. R. Chhabra et al., Tetrahedron Lett. 39, (1998), 1603), using 4% hydrazine hydrate in DMF. The following acylations were carried out by treating the resin with the N-hydroxy succinimide esters of the desired acid or using coupling reagents like HBTU/DIPEA or HOBt/DIC.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analysed by analytical HPLC and checked by ESI mass spectrometry. Crude peptides were purified by a conventional preparative HPLC purification procedure.

Analytical HPLC was performed on an Agilent 1100 Series HPLC system with a Waters XBridge BEH130 3.5 μm C18 column (2.1×150 mm) at 40° C. with a gradient elution at a flow rate of 0.5 mL/min and monitored at 215 and 280 nm. The gradients were set up as 10% B to 90% B over 15 min and then 90% B for 1 min or as 15% B to 50% B over 12.5 min and then 50% B to 90% B over 3 min. Buffer A=0.1% formic acid in water and B=0.1% formic acid in acetonitrile.

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water+0.1% TFA (A) were employed as eluents. Product-containing fractions were collected and lyophilized to obtain the purified product.

Solubility and Stability-Testing of Exendin-4 Derivatives

Prior to the testing of solubility and stability of a peptide batch, its content was determined. Therefore, two parameters were investigated, its purity (HPLC-UV) and the amount of salt load of the batch (ion chromatography). Since synthesized peptides contain primarily trifluoroacetate anions, only anion chromatography was performed.

For solubility testing, the target concentration was 1.0 mg/mL pure compound. Therefore, solutions from solid samples were prepared in different buffer systems with a concentration of 1.0 mg/mL compound based on the previously determined content. HPLC-UV was performed after 2 h of gentle agitation from the supernatant, which was obtained by 20 min of centrifugation at 4000 rpm.

The solubility was then determined by comparison with the UV peak areas obtained with a stock solution of the peptide at a concentration of 2 mg/mL in pure water or a variable amount of acetonitrile (optical control that all of the compound was dissolved). This analysis also served as starting point (t0) for the stability testing.

For stability testing, an aliquot of the supernatant obtained for solubility was stored for 7 days at 25° C. After that time course, the sample was centrifuged for 20 min at 4000 rpm and the supernatant was analysed with HPLC-UV.

For determination of the amount of the remaining peptide, the peak areas of the target compound at t0 and t7 were compared, resulting in "% remaining peptide", following the equation % remaining peptide=[(peak area peptide $t7$)×100]/peak area peptide $t0$.

The amount of soluble degradation products was calculated from the comparison of the sum of the peak areas from all observed impurities reduced by the sum of peak areas observed at t0 (i.e. to determine the amount of newly formed peptide-related species). This value was given in percentual relation to the initial amount of peptide at t0, following the equation:

% soluble degradation products={[(peak area sum of impurities $t7$)−(peak area sum of impurities $t0$)]× 100}/peak area peptide $t0$ The potential difference from the sum of "% remaining peptide" and "% soluble degradation products" to 100% reflects the amount of peptide which did not remain soluble upon stress conditions following the equation % precipitate=100−([% remaining peptide]+[% soluble degradation products])

This precipitate includes non-soluble degradation products, polymers and/or fibrils, which have been removed from analysis by centrifugation.

Anion Chromatography

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM, suppressor: ASRS 300 2 mm, detection: conductivity.

HPLC-UV

Instrument: Agilent 1100, column: X-Bridge C18 3.5 μm 2.1×150 mm (Waters), eluent: A: H20+500 ppm TFA/B: Methanol, flow: 0.55 mL/min, gradient: 0-5 min: 10-60% B; 5-15 min: 60-99% B; detection: 214 nm.

In Vitro Cellular Assays for GLP-1 Receptor and Glucagon Receptor Efficacy

Agonism of compounds for the two receptors was determined by functional assays measuring cAMP response of HEK-293 cell lines stably expressing human GLP-1 or glucagon receptor.

cAMP content of cells was determined using a kit from Cisbio Corp. (cat. no. 62AM4PEC) based on HTRF (Homogeneous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 μl-aliquots dispensed into the wells of 96-well plates. For measurement, 25 μl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Bioanalytical Screening Method for Quantification of Peptide GLP1-GCG Receptor Agonists in Mice Mice were dosed 1 mg/kg subcutaneously (s.c.). The mice were sacrificed and blood samples were collected after 0.25, 1, 2, 4, 8, 16 and 24 hours post application. Plasma samples were analysed after protein precipitation via liquid chromatography mass spectrometry (LC/MS). PK parameters and half-life were calculated using WinonLin Version 5.2.1 (non-compartment model).

Gastric Emptying and Intestinal Passage in Mice

Female NMRI-mice of a body weight between 20 and 30 g were used. Mice were adapted to housing conditions for at least one week.

Mice were overnight fasted, while water remained available all the time. On the study day, mice were weighed, single-caged and allowed access to 500 mg of feed for 30 min, while water was removed. At the end of the 30 min feeding period, remaining feed was removed and weighed. 60 min later, a coloured, non-caloric bolus was instilled via gavage into the stomach. The test compound/reference compound or its vehicle in the control group was administered subcutaneously, to reach Cmax when coloured bolus was administered. After another 30 min, the animals were sacrificed and the stomach and the small intestine prepared. The filled stomach was weighed, emptied, carefully cleaned and dried and reweighed. The calculated stomach content indicated the degree of gastric emptying. The small intestine was straightened without force and measured in length. Then the distance from the gastric beginning of the gut to the tip of the farthest travelled intestinal content bolus was measured. The intestinal passage was given as relation in percent of the latter distance and the total length of the small intestine.

Statistical analyses were performed with Everstat 6.0 by 1-way-ANOVA, followed by Dunnetts or Newman-Keuls as post-hoc test, respectively. Differences were considered statistically significant at the $p<0.05$ level. As post hoc test Dunnet's Test was applied to compare versus vehicle control, only. Newman-Keul's Test was applied for all pairwise comparisons (i.e. versus vehicle and reference groups).

Automated Assessment of Feed Intake in Mice

Female NMRI-mice of a body weight between 20 and 30 g were used. Mice were adapted to housing conditions for at least one week and for at least one day single-caged in the assessment equipment, when basal data were recorded simultaneously. On the study day, test product was administered subcutaneously close to the lights-off phase (12 h lights off) and assessment of feed consumption was directly started afterwards. Assessment included continued monitoring (every 30 min) over 22 hours. Repetition of this procedure over several days was possible. Restriction of assessment to 22 hours was for practical reasons to allow for reweighing of animals, refilling of feed and water and drug administration between procedures. Results could be assessed as cumulated data over 22 hours or differentiated to 30 min intervals.

Statistical analyses were performed with Everstat 6.0 by two-way ANOVA on repeated measures and Dunnetts post-hoc analyses. Differences were considered statistically significant at the $p<0.05$ level.

Acute and Subchronic Effects of Exendin-4 Derivatives after Subcutaneous Treatment on Blood Glucose and Body Weight in Female Diet-Induced Obese (DIO) C57BL/6NCrl Mice (10 Months on High-Fat Diet)

Female C57BL/6NCrl mice were housed in groups in a specific pathogen-free barrier facility on a 12-h light/dark cycle with free access to water and high-fat diet. After 10 months on high-fat diet, mice were stratified to treatment groups (n=8), so that each group had similar mean body weight.

An aged-matched group with ad-libitum access to standard chow was included as standard control group.

Before the experiment, mice were subcutaneously (s.c.) injected with vehicle solution and weighed for 3 days to acclimate them to the procedures.

1) Acute effect on blood glucose in fed DIO mice: initial blood samples were taken just before first administration (s.c.) of vehicle (phosphate buffer solution) or the exendin-4 derivatives at doses of 3, 10, and 100 µg/kg (dissolved in phosphate puffer), respectively. The volume of administration was 5 mL/kg. The animals had access to water and their corresponding diet during the experiment, food consumption was determined at all time points of blood sampling. Blood glucose levels were measured at t=0.5 h, t=1 h, t=2 h, t=4 h, t=6 h, t=8 h, and t=24 h (method: d-glucose hexokinase, hemolysate, AU640 Beckman Coulter). Blood sampling was performed by tail incision without anaesthesia.

Comparable data can also be obtained when using male mice.

2) Subchronic effect on body weight: all animals were treated once daily s.c. in the morning, at the beginning of the light phase (12 h lights on) with either vehicle or exendin-4 derivatives at the abovementioned doses for 4 weeks. Body weight was recorded daily. On days 6 and 28, total fat mass was measured by nuclear magnetic resonance (NMR) using a Bruker minispec (Ettlingen, Germany).

Comparable data can be obtained for both female and male mice.

Statistical analyses were performed with Everstat 6.0 by repeated measures two-way ANOVA and Dunnetts post-hoc analyses (glucose profile) and 1-way-ANOVA, followed by Dunnetts post-hoc test (body weight, body fat). Differences versus vehicle-treated DIO control mice were considered statistically significant at the p<0.05 level.

Acute and subchronic effects of exendin-4 derivatives after subcutaneous treatment on blood glucose and HbA1c in female leptin-receptor deficient diabetic db/db mice Female BKS.Cg-m+/+Leprdb/J (db/db) and BKS.Cg-m+/+Leprdb/+ (lean control) mice were obtained from Charles River Laboratories, Germany, at an age of 9-10 weeks. The animals were housed in groups in a specific pathogen-free barrier facility on a 12-h light/dark cycle with free access to water and rodent-standard chow. After 1 week of acclimatization, blood samples were drawn from the tail without anaesthesia and blood glucose (method: d-glucose hexokinase, hemolysate, AU640 Beckman Coulter) and HbA1c level (method: hemolysate, Cobas6000 c501, Roche Diagnostics, Germany) were determined.

HbA1c is a glycosylated form of haemoglobin whose level reflects the average level of glucose to which the erythrocyte has been exposed during its lifetime. In mice, HbA1c is a relevant biomarker for the average blood glucose level during the preceding 4 weeks (erythrocyte life span in mouse ~47 days).

Db/db mice were stratified to treatment groups (n=8), so that each group had similar baseline blood glucose and HbA1c levels.

1) Acute effect on blood glucose in fed db/db mice: initial blood samples were taken just before first administration (s.c.) of vehicle (phosphate buffer solution) or exendin-4 derivatives at doses of 3, 10, and 100 µg/kg (dissolved in phosphate puffer), respectively. The volume of administration was 5 mL/kg. The animals had access to water and chow during the experiment, food consumption was determined at all time points of blood sampling. Blood glucose levels were measured at t=0.5 h, t=1 h, t=2 h, t=4 h, t=6 h, t=8 h, and t=24 h. Blood sampling was performed by tail incision without anaesthesia.

Comparable data can also be obtained when using male mice.

2) Subchronic effect on blood glucose and HbA1c: all animals were treated once daily s.c. with either vehicle or exendin-4 derivatives at the abovementioned doses for 4 weeks. At the end of the study, blood samples (tail, no anaesthesia) were analyzed for glucose and HbA1c.

Comparable data can be obtained for both female and male mice.

Statistical analyses were performed with Everstat 6.0 by repeated measures two-way ANOVA and Dunnetts post-hoc analyses. Differences versus vehicle-treated db/db control mice were considered statistically significant at the p<0.05 level.

EXAMPLES

The invention is further illustrated by the following examples.

Example 1

Synthesis of SEQ ID NO: 4

The solid phase synthesis was carried out on Novabiochem Rink-Amide resin (4-(2',4'-Dimethoxyphenyl-Fmoc-aminomethyl)-phenoxpcetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm-Glu(γOSu)-OtBu was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 2

Synthesis of SEQ ID NO: 5

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm(γOSu) was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 3

Synthesis of SEQ ID NO: 6

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 and in position 40 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Palm-Glu(γOSu)-OtBu was coupled to the liberated amino-group. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 4

Synthesis of SEQ ID NO: 7

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-GABA was coupled to the liberated amino-group employing the coupling reagents HBTU/DIPEA followed by Fmoc-deprotection with 20% piperidine in DMF. Finally palmitic acid was coupled to the amino-group of GABA using HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 5

Synthesis of SEQ ID NO: 8

The solid phase synthesis was carried out on Agilent Technologies Rink-Amide resin (4-[(2,4-Dimethoxyphenyl) (Fmoc-amino)methyl]phenoxyacetomido methyl resin), 75-150 loading of 0.38 mmol/g. The Fmoc-synthesis strategy was applied with HBTU/DIPEA-activation. In position 14 Fmoc-Lys(ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. Stearic acid was coupled onto the resulting amino group after activation with HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 6

Synthesis of SEQ ID NO: 9

The solid phase synthesis was carried out on Agilent Technologies Rink-Amide resin (4-[(2,4-Dimethoxphenyl) (Fmoc-amino)methyl]phenoxyacetomido methyl resin), 75-150 μm, loading of 0.38 mmol/g. The Fmoc-synthesis strategy was applied with HBTU/DIPEA-activation. In position 14 Fmoc-Lys(ivDde)-OH and in position 1 Boc-His (Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. 4-Dodecyloxy benzoic acid was coupled onto the resulting amino group after activation with HBTU/DIPEA. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 7

Synthesis of SEQ ID NO: 10

The solid phase synthesis was carried out on Agilent Technologies Cl-Trt-Cl resin (2,α-Dichlorobenzhydryl-polystyrene crosslinked with divinylbenzene), 75-150 μm, loading of 1.4 mmol/g. Fmoc-Ser-OAllyl was synthesized according to literature (S. Ficht, R. J. Payne, R. T. Guy, C.-H. Wong, Chem. Eur. J. 14, 2008, 3620-3629) and coupled via the side chain hydroxyl function onto Cl-Trt-Cl-resin using DIPEA in dichloromethane. The Fmoc-synthesis strategy was applied with HBTU/DIPEA-activation. In position 14 Fmoc-Lys (ivDde)-OH and in position 1 Boc-His(Boc)-OH were used in the solid phase synthesis protocol. The ivDde-group was cleaved from the peptide on resin according to a modified literature procedure (S. R. Chhabra et al., Tetrahedron Lett. 39, (1998), 1603), using 4% hydrazine hydrate in DMF. Hereafter Fmoc-Glu-OtBu was coupled to the liberated amino-group using HBTU/DIPEA for activation followed by the removal of the Fmoc-group with 20% piperidine in DMF. Palmitic acid was coupled onto the resulting amino group after activation with HBTU/DIPEA. The allyl-ester group was removed employing the procedure described in literature (S. Ficht, R. J. Payne, R. T. Guy, C.-H. Wong, Chem. Eur. J. 14, 2008, 3620-3629) followed by activation of the C-terminus with HOBt/DIC in DMF and addition of n-propylamin. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

In an analogous way, the other peptides listed in Table 2 were synthesized.

TABLE 2

List of synthesized peptides and comparison of calculated vs. found molecular weight

| SEQ ID NO | calc. mass | found mass |
|---|---|---|
| 4 | 4553.1 | 4552.4 |
| 5 | 4422.0 | 4421.4 |
| 6 | 5046.9 | 5046.8 |
| 7 | 4396.0 | 4395.1 |
| 8 | 4610.2 | 4609.8 |
| 9 | 4518.1 | 4518.2 |
| 10 | 4624.2 | 4624.6 |
| 11 | 4425.0 | 4424.4 |
| 12 | 4352.0 | 4351.2 |
| 13 | 4395.0 | 4394.1 |
| 14 | 4396.9 | 4396.0 |
| 15 | 4395.0 | 4394.4 |
| 16 | 4483.0 | 4482.0 |
| 17 | 4483.0 | 4483.2 |
| 18 | 4439.9 | 4439.1 |
| 19 | 4481.1 | 4480.5 |
| 20 | 4440.9 | 4440.0 |
| 21 | 4439.0 | 4438.2 |
| 22 | 4468.0 | 4467.9 |
| 23 | 4537.2 | 4536.5 |
| 24 | 4440.0 | 4439.5 |
| 25 | 4438.0 | 4437.4 |
| 26 | 4468.1 | 4467.2 |
| 27 | 4466.1 | 4465.3 |
| 28 | 4454.0 | 4454.0 |
| 29 | 4438.1 | 4437.3 |
| 30 | 4426.0 | 4425.9 |
| 31 | 4424.0 | 4423.9 |
| 32 | 4310.9 | 4310.3 |
| 33 | 4308.9 | 4308.3 |
| 34 | 4468.0 | 4467.9 |
| 35 | 4439.9 | 4439.4 |
| 36 | 4438.0 | 4437.3 |
| 37 | 4454.0 | 4453.9 |
| 38 | 4452.0 | 4451.9 |
| 39 | 4425.9 | 4425.9 |
| 40 | 4468.0 | 4467.4 |
| 41 | 4466.0 | 4465.4 |
| 42 | 4310.8 | 4310.3 |
| 43 | 4308.9 | 4308.3 |
| 44 | 4468.0 | 4467.4 |
| 45 | 4494.1 | 4493.4 |
| 46 | 4423.0 | 4422.3 |
| 47 | 4482.0 | 4482.0 |
| 48 | 4466.1 | 4465.4 |
| 49 | 4597.1 | 4596.4 |
| 50 | 4424.0 | 4423.5 |
| 51 | 4496.1 | 4495.2 |
| 52 | 4625.2 | 4626.0 |
| 53 | 4452.1 | 4452.0 |
| 54 | 4509.1 | 4509.0 |
| 55 | 4494.0 | 4493.7 |
| 56 | 4450.0 | 4449.6 |
| 57 | 4742.4 | 4741.6 |
| 58 | 4698.4 | 4698.0 |
| 59 | 4538.2 | 4538.3 |
| 60 | 4552.2 | 4552.1 |
| 61 | 4508.1 | 4507.7 |
| 62 | 4490.0 | 4490.2 |
| 63 | 4474.0 | 4474.3 |
| 64 | 4474.0 | 4474.3 |
| 65 | 4496.1 | 4495.5 |
| 66 | 4338.9 | 4338.4 |
| 67 | 4496.1 | 4495.7 |
| 68 | 4551.2 | 4550.5 |
| 69 | 4422.1 | 4421.5 |
| 70 | 4466.1 | 4465.5 |
| 71 | 4539.1 | 4538.8 |
| 72 | 4525.0 | 4524.8 |
| 73 | 4562.1 | 4561.5 |
| 74 | 4539.1 | 4538.4 |
| 75 | 4510.1 | 4509.4 |
| 76 | 4381.0 | 4380.3 |
| 77 | 4551.1 | 4550.5 |
| 78 | 4553.1 | 4552.7 |
| 79 | 4567.1 | 4566.7 |
| 80 | 4583.1 | 4582.4 |
| 81 | 4454.0 | 4453.5 |
| 82 | 4696.3 | 4695.8 |
| 83 | 4567.1 | 4566.7 |
| 84 | 4596.2 | 4595.4 |
| 85 | 4610.2 | 4609.7 |
| 86 | 4513.0 | 4512.8 |
| 87 | 4624.2 | 4623.4 |
| 88 | 4623.2 | 4622.5 |
| 89 | 4856.5 | 4856.3 |
| 90 | 4554.1 | 4553.7 |
| 91 | 4646.1 | 4645.8 |
| 92 | 4626.2 | 4625.5 |
| 93 | 4596.1 | 4595.4 |
| 94 | 4596.1 | 4595.3 |
| 95 | 4610.2 | 4609.5 |
| 96 | 4640.2 | 4639.8 |
| 97 | 4582.1 | 4581.7 |
| 98 | 4651.3 | 4651.1 |
| 99 | 4672.3 | 4672.1 |
| 100 | 4638.3 | 4638.0 |
| 101 | 4638.3 | 4638.2 |
| 102 | 4652.2 | 4652.2 |
| 103 | 4664.2 | 4663.7 |
| 104 | 4830.4 | 4830.3 |
| 105 | 5711.5 | 5711.2 |
| 106 | 4806.6 | 4806.5 |
| 107 | 4766.5 | 4766.0 |
| 108 | 4792.6 | 4792.6 |
| 109 | 4834.6 | 4834.5 |
| 110 | 4778.5 | 4778.9 |
| 111 | 4724.3 | 4723.9 |
| 112 | 4595.2 | 4594.7 |
| 113 | 4637.2 | 4636.7 |
| 114 | 4508.1 | 4507.7 |
| 115 | 4580.1 | 4579.4 |
| 116 | 4596.1 | 4595.4 |
| 117 | 4594.2 | 4593.4 |
| 118 | 4539.1 | 4538.6 |
| 119 | 4424.0 | 4423.4 |
| 120 | 4553.1 | 4552.5 |
| 121 | 4466.1 | 4466.0 |
| 122 | 4337.0 | 4336.5 |
| 123 | 4511.0 | 4511.0 |
| 124 | 4525.1 | 4525.0 |
| 125 | 4624.2 | 4623.7 |
| 126 | 4652.2 | 4651.7 |
| 127 | 4638.2 | 4637.7 |
| 128 | 4555.1 | 4554.3 |

TABLE 2-continued

List of synthesized peptides and comparison of calculated vs. found molecular weight

| SEQ ID NO | calc. mass | found mass |
|---|---|---|
| 129 | 4569.1 | 4568.6 |
| 131 | 4381.0 | 4380.9 |
| 133 | 4506.2 | 4505.4 |
| 134 | 4470.0 | 4470.0 |
| 135 | 4484.0 | 4484.0 |
| 136 | 4468.1 | 4468.0 |
| 137 | 4463.0 | 4462.4 |
| 138 | 4475.2 | 4475.8 |
| 139 | 4495.2 | 4495.6 |
| 140 | 4555.1 | 4554.0 |
| 142 | 4482.1 | 4481.4 |
| 143 | 4468.0 | 4467.0 |
| 144 | 4440.0 | 4439.1 |
| 145 | 4442.0 | 4440.0 |
| 146 | 4468.0 | 4466.1 |
| 147 | 4441.0 | 4438.8 |
| 148 | 4464.1 | 4462.2 |
| 149 | 4506.2 | 4505.4 |
| 150 | 4453.1 | 4453.6 |
| 151 | 4468.0 | 4467.9 |
| 152 | 4593.2 | 4592.1 |
| 153 | 4506.2 | 4505.1 |
| 155 | 4423.9 | 4423.9 |
| 156 | 4452.0 | 4451.9 |
| 157 | 4454.0 | 4453.9 |
| 158 | 4464.1 | 4462.8 |
| 159 | 4506.2 | 4504.8 |
| 161 | 4581.2 | 4580.7 |
| 162 | 4565.2 | 4564.2 |
| 163 | 4567.1 | 4566.4 |
| 164 | 4468.1 | 4468.0 |
| 166 | 4541.1 | 4540.8 |
| 173 | 4442.0 | 4441.9 |
| 174 | 4609.2 | 4608.3 |
| 175 | 4595.2 | 4594.8 |
| 183 | 4214.6 | 4214.1 |
| 184 | 4188.6 | 4190.7 |
| 185 | 4259.7 | 4259.0 |
| 186 | 4231.7 | 4231.0 |
| 187 | 4188.6 | 4188.4 |
| 188 | 4174.6 | 4172.0 |
| 189 | 4075.5 | 4074.8 |
| 190 | 4145.6 | 4145.1 |
| 191 | 4057.4 | 4056.2 |
| 192 | 4043.4 | 4043.4 |
| 193 | 4043.4 | 4043.2 |
| 196 | 4496.1 | 4494.4 |
| 197 | 4577.3 | 4575.6 |
| 198 | 4563.2 | 4561.2 |
| 199 | 4593.2 | 4591.2 |
| 200 | 4591.3 | 4589.7 |
| 201 | 4548.3 | 4546.2 |
| 202 | 4536.2 | 4534.0 |
| 203 | 4534.2 | 4532.4 |
| 204 | 4548.3 | 4546.2 |
| 205 | 4591.3 | 4590.4 |
| 206 | 4565.3 | 4567.0 |
| 207 | 4710.3 | 4710.6 |
| 208 | 4562.1 | 4559.6 |
| 209 | 4620.3 | 4618.8 |
| 210 | 4618.4 | 4616.1 |
| 211 | 4533.3 | 4532.4 |
| 212 | 4575.3 | 4573.5 |
| 213 | 4493.1 | 4493.4 |
| 214 | 4521.1 | 4523.4 |
| 215 | 4535.2 | 4536.9 |
| 217 | 4544.2 | 4545.0 |
| 219 | 4546.2 | 4545.3 |
| 221 | 4495.1 | 4494.4 |
| 222 | 4523.1 | 4522.4 |
| 226 | 4622.2 | 4621.6 |
| 227 | 4631.2 | 4629.6 |

In an analogous way, the following peptides of Table 3 can be synthesized:

TABLE 3

List of peptides that can be synthesized in an analogous way.

| SEQ ID NO |
|---|
| 130 |
| 132 |
| 141 |
| 154 |
| 160 |
| 165 |
| 167 |
| 168 |
| 169 |
| 170 |
| 171 |
| 172 |
| 176 |
| 177 |
| 178 |
| 179 |
| 180 |
| 181 |
| 182 |
| 218 |
| 223 |
| 228 |
| 229 |

Example 8

Chemical Stability and Solubility

Solubility and chemical stability of peptidic compounds were assessed as described in Methods. The results are given in Table 4.

TABLE 4

Chemical stability and solubility

| SEQ ID NO | Stability | | Solubility [mg/ml] | |
|---|---|---|---|---|
|  | pH4.5 | pH7.4 | pH4.5 | pH7.4 |
| 35 | 100 | 100 | >1000 | >1000 |
| 36 | 99.7 | 100 | >1000 | >1000 |
| 44 | 99.1 | 99.4 | >1000 | >1000 |
| 24 | 100 | 100 | >1000 | >1000 |
| 25 | 99.6 | 99.6 | >1000 | >1000 |
| 66 | 100 | 98.1 | >1000 | >1000 |
| 82 | 98.4 | 99.9 | >1000 | >1000 |
| 126 | 99.5 | 91.4 | >1000 | >1000 |
| 85 | 95.9 | 85.8 | >1000 | >968.6 |
| 97 | 99.5 | 96.5 | >2000 | >2000 |
| 70 | 98.2 | 97.5 | >1000 | >1000 |
| 4 | 99.5 | 98.8 | >815 | >910 |
| 117 | 98.3 | 87.2 | >1000 | >1000 |
| 121 | 100 | 90.5 | >1000 | >980 |
| 195 |  |  | 0 | >985 |

Example 9

In Vitro Data on GLP-1 and Glucagon Receptor

Potencies of peptidic compounds at the GLP-1 and glucagon receptors were determined by exposing cells expressing human glucagon receptor (hGlucagon R) or human GLP-1 receptor (hGLP-1 R) to the listed compounds at increasing concentrations and measuring the formed cAMP as described in Methods.

The results are shown in Table 5:

TABLE 5

EC50 values of exendin-4 derivatives at GLP-1 and Glucagon receptors (indicated in pM)

| SEQ ID NO | EC50 hGLP-1R | EC50 hGlucagon-R |
|---|---|---|
| 2 | 0.7 | >10000000 |
| 3 | 56.6 | 1.0 |
| 4 | 5 | 4 |
| 5 | 11 | 109 |
| 6 | 141 | 18.9 |
| 7 | 3.5 | 20.7 |
| 8 | 6.3 | 2.3 |
| 9 | 2.2 | 4.1 |
| 10 | 9.2 | 1.7 |
| 11 | 3.6 | 25.7 |
| 12 | 4.6 | 263 |
| 13 | 3.1 | 281 |
| 14 | 4.6 | 94.7 |
| 15 | 6.6 | 176 |
| 16 | 2.8 | 117 |
| 17 | 1.7 | 93.1 |
| 18 | 2.6 | 152 |
| 19 | 1.9 | 104 |
| 20 | 3.8 | 104 |
| 21 | 3.8 | 144 |
| 22 | 1.1 | 2.4 |
| 23 | 5.6 | 126 |
| 24 | 1.9 | 9.4 |
| 25 | 4.2 | 40.6 |
| 26 | 5.1 | 5.4 |
| 27 | 7.7 | 25.1 |
| 28 | 5.5 | 12.6 |
| 29 | 5.9 | 87.9 |
| 30 | 3.2 | 7 |
| 31 | 1.7 | 9.3 |
| 32 | 10.2 | 188 |
| 33 | 11.2 | 473 |
| 34 | 1.5 | 6.7 |
| 35 | 1.5 | 14.2 |
| 36 | 2.7 | 45.9 |
| 37 | 1.5 | 12.9 |
| 38 | 2.9 | 53.1 |
| 39 | 2.7 | 7.6 |
| 40 | 2.6 | 4.8 |
| 41 | 3.3 | 20.7 |
| 42 | 10.2 | 199 |
| 43 | 4.1 | 443 |
| 44 | 2.7 | 12 |
| 45 | 7.5 | 19.9 |
| 46 | 3.2 | 25.1 |
| 47 | 2.2 | 10.3 |
| 48 | 5.9 | 53.6 |
| 49 | 1.1 | 2.9 |
| 50 | 3.3 | 11.1 |
| 51 | 2.7 | 3 |
| 52 | 1.9 | 2 |
| 53 | 5.4 | 6.5 |
| 54 | 4.8 | 4 |
| 55 | 5.4 | 15.8 |
| 56 | 4.5 | 29.3 |
| 57 | 45 | 8 |
| 58 | 45.6 | 15.1 |
| 59 | 7.9 | 6.8 |
| 60 | 38.4 | 19.3 |
| 61 | 5.3 | 16 |
| 62 | 3.9 | 10.6 |
| 63 | 4.9 | 8.4 |
| 64 | 3.1 | 6.9 |
| 65 | 5 | 5.6 |
| 66 | 8.4 | 113 |
| 67 | 15.7 | 3 |
| 68 | 7.9 | 5.7 |
| 69 | 44.8 | 52.4 |
| 70 | 6.5 | 40.9 |
| 71 | 20.5 | 5.6 |
| 72 | 25.9 | 386 |
| 73 | 4.1 | 1.7 |
| 74 | 4.2 | 1.3 |
| 75 | 11.1 | 12.5 |
| 76 | 44.9 | 162 |
| 77 | 4.3 | 11.9 |
| 78 | 17.8 | 1.6 |
| 79 | 23.3 | 7.5 |
| 80 | 5.8 | 1 |
| 81 | 48 | 7.1 |
| 82 | 11.7 | 4.7 |
| 83 | 53.9 | 41.3 |
| 84 | 8.1 | 4.3 |
| 85 | 8.1 | 10.4 |
| 86 | 4.9 | 3.5 |
| 87 | 3 | 1.3 |
| 88 | 2.4 | 1.6 |
| 89 | 35.6 | 13.7 |
| 90 | 8.8 | 3.7 |
| 91 | 15.1 | 8.9 |
| 92 | 26 | 1 |
| 93 | 10.7 | 2.6 |
| 94 | 5.2 | 2.1 |
| 95 | 20.6 | 9.2 |
| 96 | 74.3 | 3.4 |
| 97 | 3.5 | 1 |
| 98 | 9.6 | 1.4 |
| 99 | 15.9 | 2.6 |
| 100 | 13.5 | 2 |
| 101 | 9.8 | 1.7 |
| 102 | 7.2 | 1.1 |
| 103 | 10.1 | 1.7 |
| 104 | 6.5 | 1.1 |
| 105 | 7.9 | 1 |
| 106 | 210 | 10.5 |
| 107 | 188 | 37.8 |
| 108 | 197 | 9 |
| 109 | 430 | 28.6 |
| 110 | 213 | 7.2 |
| 111 | 8.1 | 2.5 |
| 112 | 33.6 | 21.1 |
| 113 | 11.4 | 5.4 |
| 114 | 62.3 | 31.1 |
| 115 | 2.4 | 1.9 |
| 116 | 6 | 3.6 |
| 117 | 3.8 | 16.5 |
| 118 | 15.3 | 4.3 |
| 119 | 30.8 | 41.2 |
| 121 | 6.1 | 23.7 |
| 122 | 24.9 | 156 |
| 123 | 2.6 | 9.7 |
| 124 | 3 | 8.4 |
| 125 | 31.4 | 6.9 |
| 126 | 6.6 | 6.8 |
| 127 | 14.7 | 9.4 |
| 128 | 6.2 | 1.6 |
| 129 | 14.8 | 4.1 |
| 131 | 9.1 | 24.9 |
| 138 | 5.5 | 9.2 |
| 140 | 1.3 | 1.5 |
| 142 | 4.1 | 2.1 |
| 150 | 6 | 35.5 |
| 152 | 3.2 | 2.3 |
| 155 | 2.5 | 25.1 |
| 156 | 2.9 | 12.5 |
| 161 | 5 | 2.4 |
| 162 | 3.1 | 2.4 |
| 173 | 5.7 | 5.9 |
| 174 | 2.6 | 1.9 |
| 175 | 2.5 | 3.1 |
| 196 | 7.8 | 1.8 |
| 197 | 6.8 | 5.8 |
| 198 | 8.2 | 2.4 |
| 199 | 10.1 | 7.2 |
| 200 | 4.6 | 4.4 |
| 201 | 22.7 | 29.6 |
| 202 | 26.2 | 6.9 |

TABLE 5-continued

EC50 values of exendin-4 derivatives at GLP-1 and Glucagon receptors (indicated in pM)

| SEQ ID NO | EC50 hGLP-1R | EC50 hGlucagon-R |
|---|---|---|
| 203 | 34.9 | 13.1 |
| 204 | 34.1 | 12.5 |
| 205 | 12.3 | 5.2 |
| 206 | 3.2 | 12.5 |
| 207 | 1.1 | 1.2 |
| 208 | 2.0 | 1.3 |
| 209 | 5.4 | 1.9 |
| 210 | 6.7 | 3.0 |
| 211 | 15.5 | 26.4 |
| 212 | 14.1 | 6.6 |
| 213 | 2.7 | 59.1 |
| 214 | 4.2 | 16.0 |
| 215 | 5.3 | 42.6 |
| 216 | 4.7 | 19.5 |
| 217 | 4.3 | 2.1 |
| 219 | 2.1 | 3.7 |
| 220 | 2.0 | 2.3 |
| 221 | 1.5 | 9.2 |
| 222 | 1.8 | 2.9 |
| 226 | 1.4 | 19.1 |
| 227 | 1.4 | 1.1 |

Example 10

Pharmacokinetic Testing

Pharmacokinetic profiles were determined as described in Methods. Calculated $T_{1/2}$ and $c_{max}$ values are shown in Table 6.

TABLE 6

Pharmacokinetic profiles of exendin-4 derivatives.

| SEQ ID NO | $T_{1/2}$ [h] | Cmax [ng/ml] |
|---|---|---|
| 35 | 3.6 | 4910 |
| 36 | 3.8 | 5260 |
| 44 | 3.4 | 2450 |
| 24 | 3.7 | 6560 |
| 8 | 3.3 | 2680 |
| 126 | 1.5 | 3160 |
| 97 | 3.2 | 2000 |
| 4 | 2.8 | 3590 |
| 117 | 2.7 | 5000 |
| 5 | 1.7 | 3180 |

Example 11

Effect of SEQ ID NO: 97 on Gastric Emptying and Intestinal Passage in Female NMRI-Mice Female NMRI-mice, weighing on average 25-30 g, received 0.02 mg/kg of SEQ ID NO: 97, Liraglutide (SEQ ID NO: 195) as reference compound, or phosphate buffered saline (vehicle control) subcutaneously, 30 min prior to the administration of the coloured bolus. 30 min later, the assessment of stomach contents and intestinal passage was done (FIG. 1a, b).

Figure 1C:
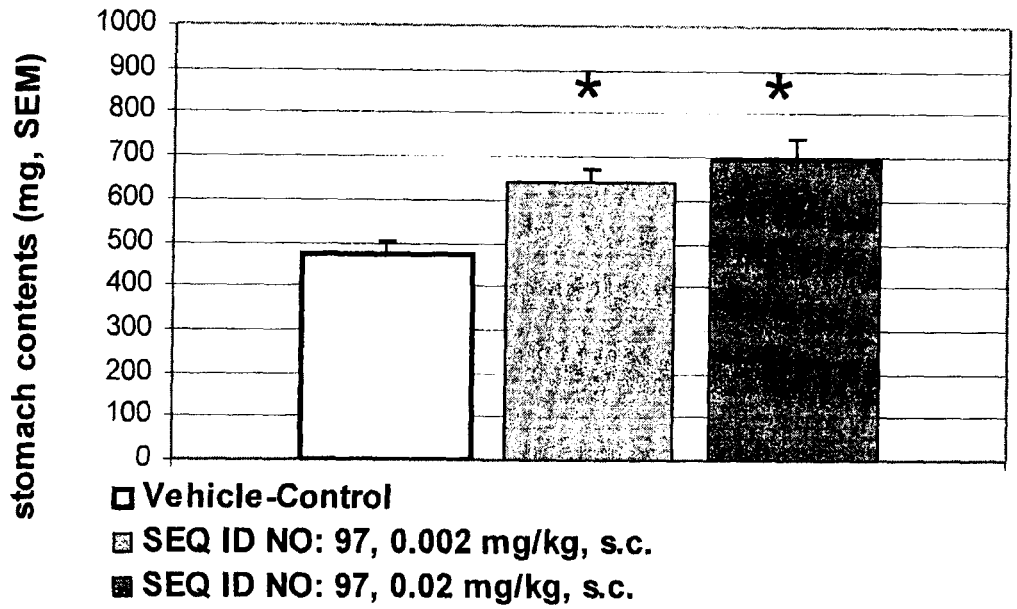
Figure 1D:
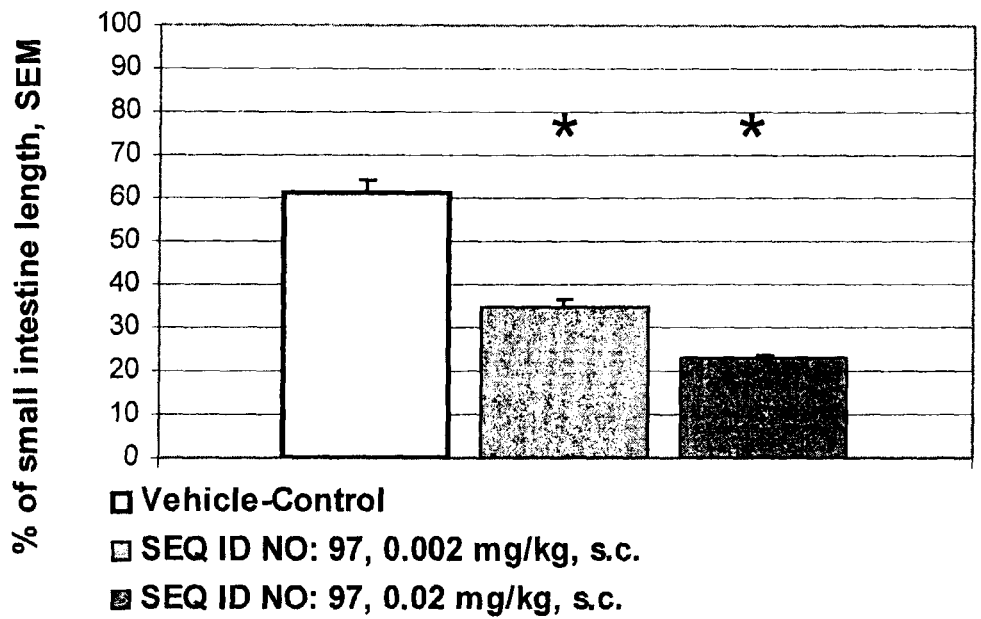

In another study, female NMRI-mice, weighing on average 25-30 g, were administered subcutaneously 0.02 and 0.002 mg/kg of SEQ ID NO: 97 or phosphate buffered saline (vehicle control), 30 min prior to the administration of the coloured bolus. 30 min later, the assessment of stomach contents and intestinal passage was done (FIG. 1c, d).

In the study with reference compound Liraglutide, SEQ ID NO: 97 reduced intestinal passage by 67% (versus 44% and 34%, respectively) and increased gastric content by 90% (versus 19% and 21%, respectively) (p<0.0001 versus vehicle control and versus comparators, 1-W-ANOVA, followed by Newman-Keul's post-hoc test) (FIG. 1a, b).

When SEQ ID NO: 97 was tested at 0.02 and 0.002 mg/kg, s.c. versus PBS-control, intestinal passage was reduced by 43% and 63%, respectively, and gastric content was increased by 37% and 47%, respectively (p<0.0001 versus vehicle control, 1-W-ANOVA, followed by Dunnett's post-hoc test) (FIG. 1c, d).

Example 12

Effect of SEQ ID NO: 97 on 22-Hours Food Intake in Female NMRI-Mice

Fed female NMRI-mice, weighing on average 25-30 g, were administered 0.01 or 0.1 mg/kg of SEQ ID NO: 97 or phosphate buffered saline (vehicle control) subcutaneously, directly prior to start of feeding monitoring (time=0 h). Lights-off phase (dark phase) started 4 hours later.

At the tested doses, SEQ ID NO: 97 demonstrated a dose-dependent reduction of feed intake, reaching 23% (p<0.0001) and 66% (p<0.0001, 2-W-ANOVA-RM, post hoc Dunnett's Test) at the end of the study, respectively (FIG. 2).

Example 13

Acute and Subchronic Effects of SEQ ID NO: 97 after Subcutaneous Treatment on Blood Glucose and Body Weight in Female Diet-Induced Obese (DIO) C57BL/6NCrl Mice (10 Months on High Fat Diet)

1) Glucose Profile

After blood sampling to determine the blood glucose baseline level, fed diet-induced obese female C57BL/6NCrl mice were administered 3, 10 or 100 µg/kg of SEQ ID NO: 97 or phosphate buffered solution (vehicle control on standard or high-fat diet) subcutaneously. At predefined time points, more blood samples were taken to measure blood glucose and generate the blood glucose profile over 24 h.

At the tested doses, SEQ ID NO: 97 demonstrated a significant dose-dependent decrease in blood glucose compared to DIO control mice, lasting at least 8 h in the low and medium dose group and >24 h in the high dose group (p<0.0001, 2-W-ANOVA-RM, post hoc Dunnett's Test; FIG. 3, mean±SEM).

2) Body Weight

Female obese C57BL/6NCrl mice were treated for 4 weeks once daily subcutaneously in the morning, at the beginning of the light phase (12 h lights on) with 3, 10 or 100 µg/kg SEQ ID NO: 97 or vehicle. Body weight was recorded daily, and body fat content was determined before the start of treatment and after 4 weeks of treatment.

Treatment with SEQ ID NO: 97 reduced body weight, whereas in the high-fat diet control group an increase in body weight could be observed. These changes resulted from a decrease (or increase in the HFD control group) in body fat, as shown by the absolute changes in body fat content. These changes reached statistical significance in the medium and high dose group (*: p<0.05, 1-W-ANOVA, post hoc Dunnett's Test, Table 7).

TABLE 7

Weight change in DIO mice over a
4-week treatment period (mean ± SEM)

| Example (Dose) | Overall weight change (g) | Body fat change (g) |
| --- | --- | --- |
| Control standard diet | −0.7 ± 0.5 | −1.1 ± 0.5 |
| Control high-fat diet | 1.3 ± 0.5 | 1.0 ± 0.4 |
| SEQ ID NO: 97 (3 µg/kg) | −0.9 ± 1.0 | −0.5 ± 0.8 |
| SEQ ID NO: 97 (10 µg/kg) | −3.0 ± 1.4* | −2.5 ± 1.0* |
| SEQ ID NO: 97 (100 µg/kg) | −2.3 ± 0.9* | −2.4 ± 0.8* |

Example 14

Acute and Subchronic Effects of SEQ ID NO: 97 after Subcutaneous Treatment on Blood Glucose and HbA1c in Female Leptin-Receptor Deficient Diabetic Db/Db Mice 1. Glucose Profile After blood sampling to determine the blood glucose baseline level, fed diabetic female db/db mice were administered 3, 10 or 100 µg/kg of SEQ ID NO: 97 or phosphate buffered solution (vehicle-treated db/db control) subcutaneously. At predefined time points, more blood samples were taken to measure blood glucose and generate the blood glucose profile over 24 h.

At the tested doses, SEQ ID NO: 97 demonstrated a significant decrease in blood glucose compared to db/db control mice, lasting up to 8 h in the low and medium dose group and >24 h in the high dose group ($p<0.0001$ for lean control mice; $p<0.01$ 1-8 h after treatment for low and medium dose, $p<0.0002$ 4-24 h for high dose; 2-W-ANOVA-RM, post hoc Dunnett's Test; FIG. 4, mean±SEM).

2. Blood Glucose & HbA1c

Female diabetic mice were treated for 4 weeks once daily subcutaneously with 3, 10 or 100 µg/kg SEQ ID NO: 97 or vehicle. Blood glucose and HbA1c were determined before start of treatment and at the end of the study after 4 weeks of treatment.

Before treatment started, no significant differences in blood glucose levels could be detected between db/db groups, only the lean control animals had significant lower glucose levels. During the 4 weeks of treatment, glucose levels increased in the vehicle-treated db/db control group, indicating a worsening of the diabetic situation. All SEQ ID NO: 97-treated animals displayed a significant lower blood glucose level than the db control mice at the end of the study ($p<0.0001$ for lean control mice; $p<0.01$ in SEQ ID NO: 97 groups; 2-W-ANOVA-RM, post hoc Dunnett's Test; FIG. 5, mean±SEM).

Corresponding to blood glucose, at the beginning of the study, no significant differences in HbA1c levels could be detected between db/db groups, only the lean control animals had significant lower levels. During the 4 weeks of treatment, HbA1c increased in the vehicle-treated db/db control group, corresponding to the increasing blood glucose levels. Animals treated with high dose SEQ ID NO: 97 displayed a significant lower HbA1c level than the db control mice at the end of the study ($p<0.0001$, 2-W-ANOVA-RM, post hoc Dunnett's Test; FIG. 6, mean±SEM).

Example 15

Comparison Testing

A selection of inventive exendin-4 derivatives comprising a functionalized amino acid in position 14 has been tested versus corresponding compounds having in this position 14 a 'non-functionalized' amino acid. The reference pair compounds and the corresponding EC50 values at GLP-1 and Glucagon receptors (indicated in pM) are given in Table 8. As shown, the inventive exendin-4 derivatives show a superior activity in comparison to the compounds with a 'non-functionalized' amino acid in position 14.

TABLE 8

Comparison of exendin-4 derivatives comprising a non-functionalized amino acid in position 14 vs. exendin-4 derivatives comprising a functionalized amino acid in position 14. EC50 values at GLP-1 and Glucagon receptors are indicated in pM.

| SEQ ID NO | EC50 hGLP-1R | EC50 hGlucagon-R | residue in position 14 |
| --- | --- | --- | --- |
| 182 | 5.8 | 419.0 | M |
| 115 | 2.4 | 1.9 | K(γE-x53) |
| 183 | 1020.0 | 916.0 | K |
| 97 | 6.8 | 1.2 | K(γE-x53) |
| 194 | 159.0 | 1290.0 | K(Ac) |
| 184 | 85.7 | 991.0 | M |
| 4 | 5.0 | 4.0 | K(γE-x53) |
| 185 | 75.7 | 262.0 | M |
| 125 | 31.4 | 6.9 | K(γE-x53) |
| 186 | 102.0 | 590.0 | M |
| 84 | 8.1 | 4.3 | K(γE-x53) |
| 187 | 152.0 | 195.0 | M |
| 78 | 17.8 | 1.6 | K(γE-x53) |
| 188 | 89.6 | 186.0 | M |
| 74 | 4.2 | 1.3 | K(γE-x53) |
| 189 | 5.6 | 1680.0 | M |
| 24 | 2.0 | 9.8 | K(γE-x53) |
| 190 | 21.3 | 1560.0 | M |
| 75 | 11.1 | 12.5 | K(γE-x53) |
| 192 | 6.8 | 478 | Nle |
| 30 | 3.2 | 7.0 | K(γE-x53) |
| 224 | 1.3 | 2930 | L |
| 216 | 4.7 | 19.5 | K(γE-x70) |
| 225 | 0.7 | 2870 | L |
| 215 | 5.3 | 42.6 | K(γE-x70) |

(M = methionine, K = lysine, Nle = norleucine, γE-x53 = (S)-4-Carboxy-4-hexadecanoylamino-butyryl-, Ac = acetate)

Example 16

Acute and Chronic Effects of SEQ ID NO: 24 after Subcutaneous Treatment on Body Weight in Male Diet-Induced Obese (DIO) C57BL/6NCrl Mice Body Weight Male obese C57BL/6NCrl mice were treated for 3 weeks twice daily subcutaneously with 0.5, 1.5, 5 or 15 µg/kg SEQ ID NO: 24 or vehicle. Body weight was recorded daily, and body fat content was determined before the start and after 3 weeks of treatment.

Treatment with SEQ ID NO: 24 reduced body weight significantly at dosages of 1.5, 5 and 15 µg/kg (*: $p<0.05$, 1-W-ANOVA, post hoc Dunnett's Test, Table 9, FIGS. 7 and 8). These changes resulted from a decrease in body fat, as shown by the absolute changes in body fat content (Table 9, FIG. 9).

TABLE 9

Weight change in DIO mice over a
3-week treatment period (mean ± SEM)

| Example (Dose) | Overall weight change (g) | Body fat change (g) |
| --- | --- | --- |
| Control standard diet | 0.02 ± 0.2 | −0.02 ± 0.22 |
| Control high-fat diet | −0.5 ± 0.3 | −0.8 ± 0.3 |

TABLE 9-continued

Weight change in DIO mice over a
3-week treatment period (mean ± SEM)

| Example (Dose) | Overall weight change (g) | Body fat change (g) |
|---|---|---|
| SEQ ID NO: 24 (0.5 µg/kg bid) | −0.9 ± 0.4 | −0.09 ± 0.3 |
| SEQ ID NO: 24 (1.5 µg/kg bid) | −6.9 ± 0.7 | −3.9 ± 0.5 |
| SEQ ID NO: 24 (5 µg/kg bid) | −7.4 ± 0.8 | −4.4 ± 0.7 |
| SEQ ID NO: 24 (15 µg/kg bid) | −9.1 ± 0.7 | −6.7 ± 0.4 |

Example 17

Acute and Chronic Effects of SEQ ID NO: 24 after Subcutaneous Treatment on Blood Glucose and HbA1c in Female Leptin-Receptor Deficient Diabetic Db/Db Mice 1. Glucose Profile After blood sampling to determine the blood glucose baseline level, fed diabetic female db/db mice were administered 50 µg/kg of SEQ ID NO: 24 or phosphate buffered solution (vehicle-treated db/db control) twice daily subcutaneously. At predefined time points, more blood samples were taken to measure blood glucose and generate the blood glucose profile over 24 h.

At the tested dose, SEQ ID NO: 24 demonstrated a significant decrease in blood glucose compared to db/db control mice, lasting >24 h ($p<0.001$; 2-W-ANOVA-RM, post hoc Dunnett's Test; FIG. 10, mean±SEM).

2. Blood Glucose & HbA1c

Female diabetic mice were treated for 4 weeks subcutaneously with 50 µg/kg SEQ ID NO: 24 or vehicle twice daily. Blood glucose and HbA1c were determined before start of treatment and at the end of the study after 4 weeks of treatment.

Before treatment started, no significant differences in blood glucose levels could be detected between db/db groups, only the lean control animals had significant lower glucose levels. During the 4 weeks of treatment, glucose levels increased in the vehicle-treated db/db control group, indicating a worsening of the diabetic situation. The SEQ ID NO: 24-treated animals displayed a significant lower blood glucose level than the db control mice at the end of the study ($p<0.01$ in SEQ ID NO: 24 group; 2-W-ANOVA-RM, post hoc Dunnett's Test; FIG. 11, mean±SEM).

Corresponding to blood glucose, at the beginning of the study, no significant differences in HbA1c levels could be detected between db/db groups, only the lean control animals had significant lower levels. During the 4 weeks of treatment, HbA1c increased in the vehicle-treated db/db control group, corresponding to the increasing blood glucose levels. Animals treated with SEQ ID NO: 24 displayed a significantly lower HbA1c level than the db control mice at the end of the study ($p<0.001$, 2-W-ANOVA-RM, post hoc Dunnett's Test; FIG. 12, mean±SEM).

TABLE 10

Sequences

| SEQ. ID | sequence |
|---|---|
| 1 | H-G-E-G-T-F-T-S-D-L-S-K-Q-M-E-E-A-V-R-L-F-I-E-W-L-K-N-G-G-P-S-S-G-A-P-P-P-S-NH2 |
| 2 | H-A-E-G-T-F-T-S-D-V-S-S-Y-L-E-G-Q-A-A-K-E-I-A-W-L-V-K-G-R-NH2 |
| 3 | H-S-Q-G-T-F-T-S-D-Y-S-K-Y-L-D-S-R-R-A-Q-D-V-Q-W-L-M-N-T-OH |
| 4 | H-dSer-Q-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 5 | H-Aib-Q-G-T-F-T-S-D-L-S-K-Q-K(x53)-E-S-R-R-A-Q-D-F-I-E-W-L-K-A-G-G-P-S-S-G-A-P-P-P-S-NH2 |
| 6 | H-dSer-Q-G-T-F-T-S-D-L-S-K-Q-K(γE-x53)-E-S-R-R-A-Q-L-F-I-E-W-L-K-A-G-G-P-S-S-G-A-P-P-P-S-K(γE-x53)-NH2 |
| 7 | H-dSer-Q-G-T-F-T-S-D-L-S-K-Q-K(GABA-x53)-E-S-K-A-A-Q-D-F-I-E-W-L-K-A-G-G-P-S-S-G-A-P-P-P-S-NH2 |
| 8 | H-dSer-Q-G-T-F-T-S-D-L-S-K-Q-K(γE-x70)-D-S-R-R-A-Q-D-F-I-E-W-L-K-N-G-G-P-S-S-G-A-P-P-P-S-NH2 |
| 9 | H-dSer-Q-G-T-F-T-S-D-L-S-K-Q-K(γE-x75)-E-S-R-A-A-Q-D-F-I-E-W-L-K-A-G-G-P-S-S-G-A-P-P-P-S-NH2 |
| 10 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(n-Propyl) |
| 11 | H-dSer-Q-G-T-F-T-S-D-L-S-K-Q-K(γE-x70)-E-S-Aib-A-A-Q-D-F-I-E-W-L-K-A-G-G-P-S-S-G-A-P-P-P-S-NH2 |
| 12 | H-dSer-Q-G-T-F-T-S-D-L-S-K-Q-K(γE-x53)-E-S-Aib-A-A-Aib-L-F-I-E-W-L-K-A-G-G-P-S-S-G-A-P-P-P-S-NH2 |
| 13 | H-Aib-Q-G-T-F-T-S-D-L-S-K-Q-K(γE-x53)-E-S-Aib-A-A-Q-D-F-I-E-W-L-K-A-G-G-P-S-S-G-A-P-P-P-S-NH2 |

TABLE 10-continued

Sequences

| SEQ. ID | sequence |
|---|---|
| 14 | H-dSer-Q-G-T-F-T-S-D-L-S-K-Q-K(γE-x53)-E-S-Aib-A-A-Q-D-F-I-E-W-L-K-A-G-G-P-S-S-G-A-P-P-P-S-NH2 |
| 15 | H-dSer-Q-G-T-F-T-S-D-L-S-K-Q-K(γE-x53)-E-S-Aib-A-A-Q-L-F-I-E-W-L-K-A-G-G-P-S-S-G-A-P-P-P-S-NH2 |
| 16 | H-dSer-Q-G-T-F-T-S-D-L-S-K-Q-K(γE-x53)-E-E-A-A-Q-D-F-I-E-W-L-K-A-G-G-P-S-S-G-A-P-P-P-S-NH2 |
| 17 | H-dSer-Q-G-T-F-T-S-D-L-S-K-Q-K(γE-x53)-E-E-A-A-K-D-F-I-E-W-L-K-A-G-G-P-S-S-G-A-P-P-P-S-NH2 |
| 18 | H-dSer-Q-G-T-F-T-S-D-L-S-K-Q-K(γE-x53)-E-E-A-A-Aib-D-F-I-E-W-L-K-A-G-G-P-S-S-G-A-P-P-P-S-NH2 |
| 19 | H-dSer-Q-G-T-F-T-S-D-L-S-K-Q-K(γE-x53)-E-E-A-A-K-L-F-I-E-W-L-K-A-G-G-P-S-S-G-A-P-P-P-S-NH2 |
| 20 | H-dSer-Q-G-T-F-T-S-D-L-S-K-Q-K(γE-x53)-E-S-E-A-A-Q-D-F-I-E-W-L-K-A-G-G-P-S-S-G-A-P-P-P-S-NH2 |
| 21 | H-dSer-Q-G-T-F-T-S-D-L-S-K-Q-K(γE-x53)-E-S-E-A-A-Q-L-F-I-E-W-L-K-A-G-G-P-S-S-G-A-P-P-P-S-NH2 |
| 22 | H-dSer-Q-G-T-F-T-S-D-L-S-K-Q-K(γE-x53)-D-E-K-A-A-Q-D-F-I-E-W-L-K-A-G-G-P-S-S-G-A-P-P-P-S-NH2 |
| 23 | H-dSer-Q-G-T-F-T-S-D-L-S-K-Q-K(γE-x53)-E-E-K-K-A-K-L-F-I-E-W-L-K-A-G-G-P-S-S-G-A-P-P-P-S-NH2 |
| 24 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH2 |
| 25 | H-Aib-Q-G-T-F-T-S-D-L-S-K-Q-K(γE-x53)-E-S-K-A-A-Q-D-F-I-E-W-L-K-A-G-G-P-S-S-G-A-P-P-P-S-NH2 |
| 26 | H-dSer-Q-G-T-F-T-S-D-L-S-K-Q-K(γE-x70)-E-S-K-A-A-Q-D-F-I-E-W-L-K-A-G-G-P-S-S-G-A-P-P-P-S-NH2 |
| 27 | H-dSer-Q-G-T-F-T-S-D-L-S-K-Q-K(γE-x70)-E-S-K-A-A-Q-L-F-I-E-W-L-K-A-G-G-P-S-S-G-A-P-P-P-S-NH2 |
| 28 | H-dSer-Q-G-T-F-T-S-D-L-S-K-Q-K(γE-x53)-E-S-K-A-A-Q-E-F-I-E-W-L-K-A-G-G-P-S-S-G-A-P-P-P-S-NH2 |
| 29 | H-dSer-Q-G-T-F-T-S-D-L-S-K-Q-K(γE-x53)-E-S-K-A-A-Q-L-F-I-E-W-L-K-A-G-G-P-S-S-G-A-P-P-P-S-NH2 |
| 30 | H-dSer-Q-G-T-F-T-S-D-L-S-K-Q-K(γE-x53)-D-S-K-A-A-Q-D-F-I-E-W-L-K-A-G-G-P-S-S-G-A-P-P-P-S-NH2 |
| 31 | H-Aib-Q-G-T-F-T-S-D-L-S-K-Q-K(γE-x53)-D-S-K-A-A-Q-D-F-I-E-W-L-K-A-G-G-P-S-S-G-A-P-P-P-S-NH2 |
| 32 | H-dSer-Q-G-T-F-T-S-D-L-S-K-Q-K(x53)-E-S-K-A-A-Q-D-F-I-E-W-L-K-A-G-G-P-S-S-G-A-P-P-P-S-NH2 |
| 33 | H-Aib-Q-G-T-F-T-S-D-L-S-K-Q-K(x53)-E-S-K-A-A-Q-D-F-I-E-W-L-K-A-G-G-P-S-S-G-A-P-P-P-S-NH2 |
| 34 | H-dSer-Q-G-T-F-T-S-D-L-S-K-Q-K(γE-x53)-D-E-Q-A-A-Q-D-F-I-E-W-L-K-A-G-G-P-S-S-G-A-P-P-P-S-NH2 |
| 35 | H-dSer-Q-G-T-F-T-S-D-L-S-K-Q-K(γE-x53)-E-S-Q-A-A-Q-D-F-I-E-W-L-K-A-G-G-P-S-S-G-A-P-P-P-S-NH2 |
| 36 | H-Aib-Q-G-T-F-T-S-D-L-S-K-Q-K(γE-x53)-E-S-Q-A-A-Q-D-F-I-E-W-L-K-A-G-G-P-S-S-G-A-P-P-P-S-NH2 |
| 37 | H-dSer-Q-G-T-F-T-S-D-L-S-K-Q-K(γE-x53)-E-S-Q-A-A-Q-E-F-I-E-W-L-K-A-G-G-P-S-S-G-A-P-P-P-S-NH2 |
| 38 | H-Aib-Q-G-T-F-T-S-D-L-S-K-Q-K(γE-x53)-E-S-Q-A-A-Q-E-F-I-E-W-L-K-A-G-G-P-S-S-G-A-P-P-P-S-NH2 |

TABLE 10-continued

Sequences

| SEQ. ID | sequence |
|---|---|
| 39 | H-dSer-Q-G-T-F-T-S-D-L-S-K-Q-K(γE-x53)-D-S-Q-A-A-Q-D-F-I-E-W-L-K-A-G-G-P-S-S-G-A-P-P-P-S-NH2 |
| 40 | H-dSer-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 41 | H-Aib-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 42 | H-dSer-Q-G-T-F-T-S-D-L-S-K-Q-K(x53)-E-S-Q-A-A-Q-D-F-I-E-W-L-K-A-G-G-P-S-S-G-A-P-P-P-S-NH2 |
| 43 | H-Aib-Q-G-T-F-T-S-D-L-S-K-Q-K(x53)-E-S-Q-A-A-Q-D-F-I-E-W-L-K-A-G-G-P-S-S-G-A-P-P-P-S-NH2 |
| 44 | H-dSer-Q-G-T-F-T-S-D-L-S-K-Q-K(γE-x53)-E-S-R-A-A-Q-D-F-I-E-W-L-K-A-G-G-P-S-S-G-A-P-P-P-S-NH2 |
| 45 | H-dSer-Q-G-T-F-T-S-D-L-S-K-Q-K(γE-x70)-E-S-R-A-A-Q-L-F-I-E-W-L-K-A-G-G-P-S-S-G-A-P-P-P-S-NH2 |
| 46 | H-dSer-Q-G-T-F-T-S-D-L-S-K-Q-K(γE-x53)-E-S-R-A-A-Aib-L-F-I-E-W-L-K-A-G-G-P-S-S-G-A-P-P-P-S-NH2 |
| 47 | H-dSer-Q-G-T-F-T-S-D-L-S-K-Q-K(γE-x53)-E-S-R-A-A-Q-E-F-I-E-W-L-K-A-G-G-P-S-S-G-A-P-P-P-S-NH2 |
| 48 | H-dSer-Q-G-T-F-T-S-D-L-S-K-Q-K(γE-x53)-E-S-R-A-A-Q-L-F-I-E-W-L-K-A-G-G-P-S-S-G-A-P-P-P-S-NH2 |
| 49 | H-dSer-Q-G-T-F-T-S-D-L-S-K-Q-K(γE-γE-x53)-E-S-R-A-A-Q-D-F-I-E-W-L-K-A-G-G-P-S-S-G-A-P-P-P-S-NH2 |
| 50 | H-dSer-Q-G-T-F-T-S-D-L-S-K-Q-K(GABA-x53)-E-S-R-A-A-Q-D-F-I-E-W-L-K-A-G-G-P-S-S-G-A-P-P-P-S-NH2 |
| 51 | H-dSer-Q-G-T-F-T-S-D-L-S-K-Q-K(γE-x70)-E-S-R-A-A-Q-D-F-I-E-W-L-K-A-G-G-P-S-S-G-A-P-P-P-S-NH2 |
| 52 | H-dSer-Q-G-T-F-T-S-D-L-S-K-Q-K(γE-γE-x70)-E-S-R-A-A-Q-D-F-I-E-W-L-K-A-G-G-P-S-S-G-A-P-P-P-S-NH2 |
| 53 | H-dSer-Q-G-T-F-T-S-D-L-S-K-Q-K(GABA-x70)-E-S-R-A-A-Q-D-F-I-E-W-L-K-A-G-G-P-S-S-G-A-P-P-P-S-NH2 |
| 54 | H-dSer-Q-G-T-F-T-S-D-L-S-K-Q-K(βA-βA-x70)-E-S-R-A-A-Q-D-F-I-E-W-L-K-A-G-G-P-S-S-G-A-P-P-P-S-NH2 |
| 55 | H-dSer-Q-G-T-F-T-S-D-L-S-K-Q-K(γE-x74)-E-S-R-A-A-Q-D-F-I-E-W-L-K-A-G-G-P-S-S-G-A-P-P-P-S-NH2 |
| 56 | H-dSer-Q-G-T-F-T-S-D-L-S-K-Q-K(GABA-x74)-E-S-R-A-A-Q-D-F-I-E-W-L-K-A-G-G-P-S-S-G-A-P-P-P-S-NH2 |
| 57 | H-dSer-Q-G-T-F-T-S-D-L-S-K-Q-K(γE-x60)-E-S-R-A-A-Q-D-F-I-E-W-L-K-A-G-G-P-S-S-G-A-P-P-P-S-NH2 |
| 58 | H-dSer-Q-G-T-F-T-S-D-L-S-K-Q-K(GABA-x60)-E-S-R-A-A-Q-D-F-I-E-W-L-K-A-G-G-P-S-S-G-A-P-P-P-S-NH2 |
| 59 | H-dSer-Q-G-T-F-T-S-D-L-S-K-Q-K(γE-x76)-E-S-R-A-A-Q-D-F-I-E-W-L-K-A-G-G-P-S-S-G-A-P-P-P-S-NH2 |
| 60 | H-dSer-Q-G-T-F-T-S-D-L-S-K-Q-K(γE-x77)-E-S-R-A-A-Q-D-F-I-E-W-L-K-A-G-G-P-S-S-G-A-P-P-P-S-NH2 |
| 61 | H-dSer-Q-G-T-F-T-S-D-L-S-K-Q-K(γE-x79)-E-S-R-A-A-Q-D-F-I-E-W-L-K-A-G-G-P-S-S-G-A-P-P-P-S-NH2 |
| 62 | H-dSer-Q-G-T-F-T-S-D-L-S-K-Q-K(γE-x80)-E-S-R-A-A-Q-D-F-I-E-W-L-K-A-G-G-P-S-S-G-A-P-P-P-S-NH2 |
| 63 | H-dSer-Q-G-T-F-T-S-D-L-S-K-Q-K(γE-x81)-E-S-R-A-A-Q-D-F-I-E-W-L-K-A-G-G-P-S-S-G-A-P-P-P-S-NH2 |

TABLE 10-continued

Sequences

| SEQ. ID | sequence |
|---|---|
| 64 | H-dSer-Q-G-T-F-T-S-D-L-S-K-Q-K(γE-x82)-E-S-R-A-A-Q-D-F-I-E-W-L-K-A-G-G-P-S-S-G-A-P-P-P-S-NH2 |
| 65 | H-dSer-Q-G-T-F-T-S-D-L-S-K-Q-K(γE-x70)-E-S-R-A-A-Q-D-F-I-E-W-L-K-A-G-G-P-S-S-G-A-P-P-P-S-NH2 |
| 66 | H-dSer-Q-G-T-F-T-S-D-L-S-K-Q-K(x53)-E-S-R-A-A-Q-D-F-I-E-W-L-K-A-G-G-P-S-S-G-A-P-P-P-S-NH2 |
| 67 | H-dSer-Q-G-T-F-T-S-D-L-S-K-Q-K(γE-x53)-D-S-R-R-A-Aib-D-F-I-E-W-L-K-A-G-G-P-S-S-G-A-P-P-P-S-NH2 |
| 68 | H-dSer-Q-G-T-F-T-S-D-L-S-K-Q-K(γE-x53)-E-S-R-R-A-Q-L-F-I-E-W-L-K-A-G-G-P-S-S-G-A-P-P-P-S-NH2 |
| 69 | H-dSer-Q-G-T-F-T-S-D-L-S-K-Q-K(x53)-E-S-R-R-A-Q-L-F-I-E-W-L-K-A-G-G-P-S-S-G-A-P-P-P-S-NH2 |
| 70 | H-dSer-Q-G-T-F-T-S-D-L-S-K-Q-K(γE-x53)-E-S-R-A-A-Q-L-F-I-E-W-L-K-A-G-G-P-S-S-G-A-P-P-P-S-NH2 |
| 71 | H-dSer-Q-G-T-F-T-S-D-L-S-K-Q-Orn(γE-x53)-E-S-R-R-A-Q-D-F-I-E-W-L-K-A-G-G-P-S-S-G-A-P-P-P-S-NH2 |
| 72 | H-dSer-Q-G-T-F-T-S-D-L-S-K-Q-Dab(γE-x53)-E-S-R-R-A-Q-D-F-I-E-W-L-K-A-G-G-P-S-S-G-A-P-P-P-S-NH2 |
| 73 | H-dSer-H-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 74 | H-dSer-Q-G-T-F-T-S-D-L-S-K-Q-K(γE-x53)-D-S-R-R-A-Q-D-F-I-E-W-L-K-A-G-G-P-S-S-G-A-P-P-P-S-NH2 |
| 75 | H-dSer-Q-G-T-F-T-S-D-L-S-K-Q-K(γE-x53)-E-S-R-R-A-Aib-D-F-I-E-W-L-K-A-G-G-P-S-S-G-A-P-P-P-S-NH2 |
| 76 | H-dSer-Q-G-T-F-T-S-D-L-S-K-Q-K(x53)-E-S-R-R-A-Aib-D-F-I-E-W-L-K-A-G-G-P-S-S-G-A-P-P-P-S-NH2 |
| 77 | H-Aib-Q-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 78 | H-dSer-Q-G-T-F-T-S-D-L-S-K-Q-K(γE-x53)-D-S-R-R-A-Q-D-F-I-E-W-L-K-Aib-G-G-P-S-S-G-A-P-P-P-S-NH2 |
| 79 | H-dSer-Q-G-T-F-T-S-D-L-S-K-Q-K(γE-x53)-E-S-R-R-A-Q-D-F-I-E-W-L-K-Aib-G-G-P-S-S-G-A-P-P-P-S-NH2 |
| 80 | H-dSer-Q-G-T-F-T-S-D-L-S-K-Q-K(γE-x53)-D-S-R-R-A-Q-D-F-I-E-W-L-K-D-G-G-P-S-S-G-A-P-P-P-S-NH2 |
| 81 | H-dSer-Q-G-T-F-T-S-D-L-S-K-Q-K(x53)-D-S-R-R-A-Q-D-F-I-E-W-L-K-D-G-G-P-S-S-G-A-P-P-P-S-NH2 |
| 82 | H-dSer-Q-G-T-F-T-S-D-L-S-K-Q-K(γE-x53)-E-S-R-R-A-Q-D-F-I-E-W-L-K-E-G-G-P-S-S-G-R-P-P-P-S-NH2 |
| 83 | H-dSer-Q-G-T-F-T-S-D-L-S-K-Q-K(x53)-E-S-R-R-A-Q-D-F-I-E-W-L-K-E-G-G-P-S-S-G-R-P-P-P-S-NH2 |
| 84 | H-dSer-Q-G-T-F-T-S-D-L-S-K-Q-K(γE-x53)-D-S-R-R-A-Q-D-F-I-E-W-L-K-K-G-G-P-S-S-G-A-P-P-P-S-NH2 |
| 85 | H-dSer-Q-G-T-F-T-S-D-L-S-K-Q-K(γE-x53)-E-S-R-R-A-Q-D-F-I-E-W-L-K-K-G-G-P-S-S-G-A-P-P-P-S-NH2 |
| 86 | H-dSer-Q-G-T-F-T-S-D-L-S-K-Q-K(γE-x53)-D-S-Q-A-A-Q-D-F-I-E-W-L-K-N-T-G-P-S-S-G-A-P-P-P-S-NH2 |
| 87 | H-dSer-Q-G-T-F-T-S-D-L-S-K-Q-K(γE-x53)-D-E-R-R-A-K-D-F-I-E-W-L-K-N-G-G-P-S-S-G-A-P-P-P-S-NH2 |
| 88 | H-dSer-Q-G-T-F-T-S-D-L-S-K-Q-K(γE-x53)-E-K-R-R-A-Q-D-F-I-E-W-L-K-N-G-G-P-S-S-G-A-P-P-P-S-NH2 |

TABLE 10-continued

Sequences

| SEQ. ID | sequence |
|---|---|
| 89 | H-dSer-Q-G-T-F-T-S-D-L-S-K-Q-K(γE-x60)-D-S-R-R-A-Q-D-F-I-E-W-L-K-N-G-G-P-S-S-G-A-P-P-P-S-NH2 |
| 90 | H-dSer-Q-G-T-F-T-S-D-L-S-K-Q-K(γE-x69)-D-S-R-R-A-Q-D-F-I-E-W-L-K-N-G-G-P-S-S-G-A-P-P-P-S-NH2 |
| 91 | H-dSer-Q-G-T-F-T-S-D-L-S-K-Q-K(γE-x72)-D-S-R-R-A-Q-D-F-I-E-W-L-K-N-G-G-P-S-S-G-A-P-P-P-S-NH2 |
| 92 | H-dSer-Q-G-T-F-T-S-D-L-S-K-Q-K(γE-x53)-D-S-R-R-A-Q-D-F-I-E-W-L-K-N-T-G-P-S-S-G-A-P-P-P-S-NH2 |
| 93 | H-dSer-Q-G-T-F-T-S-D-L-S-K-Q-K(γE-x53)-D-S-R-R-A-Q-D-F-I-E-W-L-K-N-A-G-P-S-S-G-A-P-P-P-S-NH2 |
| 94 | H-dSer-Q-G-T-F-T-S-D-L-S-K-Q-K(γE-x53)-D-S-R-R-A-Q-D-F-I-E-W-L-K-N-dAla-G-P-S-S-G-A-P-P-P-S-NH2 |
| 95 | H-dSer-Q-G-T-F-T-S-D-L-S-K-Q-K(γE-x53)-E-S-R-R-A-Q-D-F-I-E-W-L-K-N-A-G-P-S-S-G-A-P-P-P-S-NH2 |
| 96 | H-dSer-Q-G-T-F-T-S-D-L-S-K-Q-K(γE-x53)-E-S-R-R-A-Q-D-F-I-E-W-L-K-N-T-G-P-S-S-G-A-P-P-P-S-NH2 |
| 97 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH2 |
| 98 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(pyrrolidin) |
| 99 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(benzyl) |
| 100 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(tert.butyl) |
| 101 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-N(diethyl) |
| 102 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-N(morpholin) |
| 103 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(CH2—CF3) |
| 104 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2—CH2—O)4-CH2—CH2—COOH] |
| 105 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2—CH2—O)24-CH2—CH2—COOH] |
| 106 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)15-CH3] |
| 107 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)12-OH] |
| 108 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(CH2)14-CH3] |
| 109 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH[(CH2)17-CH3] |
| 110 | H-dSer-Q-G-T-F-T-S-D-L-S-K-Q-K(γE-x53)-D-S-R-R-A-Q-D-F-I-E-W-L-K-N-G-G-P-S-S-G-A-P-P-P-S-NH(CH2)13-CH3] |
| 111 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-S-K-NH2 |
| 112 | H-dSer-Q-G-T-F-T-S-D-L-S-K-Q-K(x53)-E-S-R-R-A-Q-D-F-I-E-W-L-K-N-G-G-P-S-S-G-A-P-P-P-S-K-NH2 |

TABLE 10-continued

Sequences

| SEQ. ID | sequence |
|---|---|
| 113 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-K-NH2 |
| 114 | H-dSer-Q-G-T-F-T-S-D-L-S-K-Q-K(x53)-E-S-R-R-A-Q-D-F-I-E-W-L-K-N-G-G-P-S-S-G-A-P-P-P-K-NH2 |
| 115 | H-Aib-Q-G-T-F-T-S-D-L-S-K-Q-K(γE-x53)-D-S-R-R-A-Q-D-F-I-E-W-L-K-N-G-G-P-S-S-G-A-P-P-P-S-NH2 |
| 116 | H-dSer-Q-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 117 | H-Aib-Q-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 118 | H-dSer-Q-G-T-F-T-S-D-L-S-K-Q-K(γE-x53)-D-S-R-R-A-Aib-D-F-I-E-W-L-K-N-G-G-P-S-S-G-A-P-P-P-S-NH2 |
| 119 | H-dSer-Q-G-T-F-T-S-D-L-S-K-Q-K(x53)-E-S-R-R-A-Aib-D-F-I-E-W-L-K-N-G-G-P-S-S-G-A-P-P-P-S-NH2 |
| 120 | H-dSer-Q-G-T-F-T-S-D-L-S-K-Q-K(γE-x53)-E-S-R-R-A-Aib-D-F-I-E-W-L-K-N-G-G-P-S-S-G-A-P-P-P-S-NH2 |
| 121 | H-dSer-Q-G-T-F-T-S-D-L-S-K-Q-K(γE-x53)-E-S-R-R-A-Aib-L-F-I-E-W-L-K-N-G-G-P-S-S-G-A-P-P-P-S-NH2 |
| 122 | H-dSer-Q-G-T-F-T-S-D-L-S-K-Q-K(x53)-E-S-R-A-A-Aib-L-F-I-E-W-L-K-N-G-G-P-S-S-G-A-P-P-P-S-NH2 |
| 123 | H-dSer-Q-G-T-F-T-S-D-L-S-K-Q-K(γE-x53)-D-S-Q-A-A-Q-D-F-I-E-W-L-K-R-G-G-P-S-S-G-A-P-P-P-S-NH2 |
| 124 | H-dSer-Q-G-T-F-T-S-D-L-S-K-Q-K(γE-x53)-D-S-Q-A-A-Q-D-F-I-E-W-L-K-R-A-G-P-S-S-G-A-P-P-P-S-NH2 |
| 125 | H-dSer-Q-G-T-F-T-S-D-L-S-K-Q-K(γE-x53)-D-S-R-R-A-Q-D-F-I-E-W-L-K-R-G-G-P-S-S-G-A-P-P-P-S-NH2 |
| 126 | H-dSer-Q-G-T-F-T-S-D-L-S-K-Q-K(γE-x53)-E-S-R-R-A-Q-D-F-I-E-W-L-K-R-dAla-G-P-S-S-G-A-P-P-P-S-NH2 |
| 127 | H-dSer-Q-G-T-F-T-S-D-L-S-K-Q-K(γE-x53)-E-S-R-R-A-Q-D-F-I-E-W-L-K-R-G-G-P-S-S-G-A-P-P-P-S-NH2 |
| 128 | H-dSer-Q-G-T-F-T-S-D-L-S-K-Q-K(γE-x53)-D-S-R-R-A-Q-D-F-I-E-W-L-K-S-G-G-P-S-S-G-A-P-P-P-S-NH2 |
| 129 | H-dSer-Q-G-T-F-T-S-D-L-S-K-Q-K(γE-x53)-E-S-R-R-A-Q-D-F-I-E-W-L-K-S-G-G-P-S-S-G-A-P-P-P-S-NH2 |
| 130 | H-dSer-Q-G-T-F-T-S-D-L-S-K-Q-K(γE-x70)-E-S-Aib-A-A-Q-L-F-I-E-W-L-K-A-G-G-P-S-S-G-A-P-P-P-S-NH2 |
| 131 | H-dSer-Q-G-T-F-T-S-D-L-S-K-Q-K(GABA-x70)-E-S-Aib-A-A-Q-L-F-I-E-W-L-K-A-G-G-P-S-S-G-A-P-P-P-S-NH2 |
| 132 | H-Aib-Q-G-T-F-T-S-D-L-S-K-Q-K(γE-x53)-E-S-Aib-A-A-Q-L-F-I-E-W-L-K-A-G-G-P-S-S-G-A-P-P-P-S-NH2 |
| 133 | H-Aib-Q-G-T-F-T-S-D-L-S-K-Q-K(γE-x70)-E-S-K-A-A-K-L-F-I-E-W-L-K-A-dAla-G-P-S-S-G-A-P-P-P-S-NH2 |
| 134 | H-dSer-Q-G-T-F-T-S-D-L-S-K-Q-K(x52)-E-S-K-A-A-Q-D-F-I-E-W-L-K-A-G-G-P-S-S-G-A-P-P-P-S-NH2 |
| 135 | H-dSer-Q-G-T-F-T-S-D-L-S-K-Q-K(x52)-E-S-K-A-A-Q-E-F-I-E-W-L-K-A-G-G-P-S-S-G-A-P-P-P-S-NH2 |
| 136 | H-dSer-Q-G-T-F-T-S-D-L-S-K-Q-K(x52)-E-S-K-A-A-Q-L-F-I-E-W-L-K-A-G-G-P-S-S-G-A-P-P-P-S-NH2 |
| 137 | H-dSer-H-G-T-F-T-S-D-L-S-K-Q-K(γE-X70)-D-S-K-A-A-Q-D-F-I-E-W-L-K-A-G-G-P-S-S-G-A-P-P-P-S-NH2 |

TABLE 10-continued

Sequences

| SEQ. ID | sequence |
|---|---|
| 138 | H-dSer-H-G-T-F-T-S-D-L-S-K-Q-K(γE-X70)-D-S-K-A-A-Q-L-F-I-E-W-L-K-A-dAla-G-P-S-S-G-A-P-P-P-S-NH2 |
| 139 | H-dSer-Q-G-T-F-T-S-D-L-S-K-Q-K(γE-x76)-D-S-K-A-A-Q-D-F-I-E-W-L-K-A-G-G-P-S-S-G-A-P-P-P-S-NH2 |
| 140 | H-dSer-Q-G-T-F-T-S-D-L-S-K-Q-K(γE-γE-x53)-D-S-K-A-A-Q-D-F-I-E-W-L-K-A-G-G-P-S-S-G-A-P-P-P-S-NH2 |
| 141 | H-dSer-Q-G-T-F-T-S-D-L-S-K-Q-K(Phospho1)-D-S-K-A-A-Q-D-F-I-E-W-L-K-A-G-G-P-S-S-G-A-P-P-P-S-NH2 |
| 142 | H-dSer-Q-G-T-F-T-S-D-L-S-K-Q-K(γE-X95)-D-S-K-A-A-Q-D-F-I-E-W-L-K-A-G-G-P-S-S-G-A-P-P-P-S-NH2 |
| 143 | H-dSer-Q-G-T-F-T-S-D-L-S-K-Q-K(γE-X70)-D-S-K-A-A-Q-D-F-I-E-W-L-K-A-dAla-G-P-S-S-G-A-P-P-P-S-NH2 |
| 144 | H-dSer-Q-G-T-F-T-S-D-L-S-K-Q-K(γE-x53)-D-S-K-A-Aib-Q-D-F-I-E-W-L-K-A-G-G-P-S-S-G-A-P-P-P-S-NH2 |
| 145 | H-dSer-Q-G-T-F-T-S-D-L-S-K-Q-K(γE-x53)-D-S-K-A-S-Q-D-F-I-E-W-L-K-A-G-G-P-S-S-G-A-P-P-P-S-NH2 |
| 146 | H-dSer-Q-G-T-F-T-S-D-L-S-K-Q-K(γE-x53)-D-S-K-A-L-Q-D-F-I-E-W-L-K-A-G-G-P-S-S-G-A-P-P-P-S-NH2 |
| 147 | H-dSer-Q-G-T-F-T-S-D-L-S-K-Q-K(γE-x53)-D-S-K-A-A-Q-D-F-I-E-W-L-K-A-G-G-P-S-S-G-A-P-P-P-S-NH2 |
| 148 | H-Aib-Q-G-T-F-T-S-D-L-S-K-Q-K(γE-x70)-D-S-K-A-A-Q-L-F-I-E-W-K-K-A-dAla-G-P-S-S-G-A-P-P-P-S-NH2 |
| 149 | H-Aib-Q-G-T-F-T-S-D-L-S-K-Q-K(γE-x76)-D-S-K-A-A-Q-L-F-I-E-W-L-K-A-dAla-G-P-S-S-G-A-P-P-P-S-NH2 |
| 150 | H-dSer-Q-G-T-F-T-S-D-L-S-K-Q-K(γE-x53)-E-S-L-A-A-Q-D-F-I-E-W-L-K-A-G-G-P-S-S-G-A-P-P-P-S-NH2 |
| 151 | H-dSer-Q-G-T-F-T-S-D-L-S-K-Q-K(γE-x53)-D-E-Q-A-A-K-D-F-I-E-W-L-K-A-G-G-P-S-S-G-A-P-P-P-S-NH2 |
| 152 | H-Aib-Q-G-T-F-T-S-D-L-S-K-Q-K(γE-x70)-D-E-Q-R-A-K-E-F-I-E-W-L-K-A-G-G-P-S-S-G-A-P-P-P-S-NH2 |
| 153 | H-Aib-Q-G-T-F-T-S-D-L-S-K-Q-K(γE-x70)-D-E-Q-A-A-K-L-F-I-E-W-L-K-A-dAla-G-P-S-S-G-A-P-P-P-S-NH2 |
| 154 | H-Aib-Q-G-T-F-T-S-D-L-S-K-Q-K(γE-x70)-E-S-Q-A-A-Q-D-F-I-E-W-L-K-A-G-G-P-S-S-G-A-P-P-P-S-NH2 |
| 155 | H-Aib-Q-G-T-F-T-S-D-L-S-K-Q-K(γE-x53)-D-S-Q-A-A-Q-D-F-I-E-W-L-K-A-G-G-P-S-S-G-A-P-P-P-S-NH2 |
| 156 | H-Aib-Q-G-T-F-T-S-D-L-S-K-Q-K(γE-X70)-D-S-Q-A-A-Q-D-F-I-E-W-L-K-A-G-G-P-S-S-G-A-P-P-P-S-NH2 |
| 157 | H-dSer-Q-G-T-F-T-S-D-L-S-K-Q-K(γE-X70)-D-S-Q-A-A-Q-D-F-I-E-W-L-K-A-G-G-P-S-S-G-A-P-P-P-S-NH2 |
| 158 | H-Aib-Q-G-T-F-T-S-D-L-S-K-Q-K(γE-x70)-D-S-Q-A-A-Q-L-F-I-E-W-L-K-A-dAla-G-P-S-S-G-A-P-P-P-S-NH2 |
| 159 | H-Aib-Q-G-T-F-T-S-D-L-S-K-Q-K(γE-x76)-D-S-Q-A-A-Q-L-F-I-E-W-L-K-A-dAla-G-P-S-S-G-A-P-P-P-S-NH2 |
| 160 | H-dSer-Q-G-T-F-T-S-D-L-S-K-Q-K(γE-x61)-E-S-R-A-A-Q-D-F-I-E-W-L-K-A-G-G-P-S-S-G-A-P-P-P-S-NH2 |
| 161 | H-dSer-Q-G-T-F-T-S-D-L-S-K-Q-K(γE-X70)-D-S-R-R-A-Q-D-F-I-E-W-L-K-A-dAla-G-P-S-S-G-A-P-P-P-S-NH2 |
| 162 | H-Aib-Q-G-T-F-T-S-D-L-S-K-Q-K(γE-X70)-D-S-R-R-A-Q-D-F-I-E-W-L-K-A-G-G-P-S-S-G-A-P-P-P-S-NH2 |

TABLE 10-continued

Sequences

| SEQ. ID | sequence |
|---|---|
| 163 | H-dSer-Q-G-T-F-T-S-D-L-S-K-Q-K(γE-X70)-D-S-R-R-A-Q-D-F-I-E-W-L-K-A-G-G-P-S-S-G-A-P-P-P-S-NH2 |
| 164 | H-dSer-Q-G-T-F-T-S-D-L-S-K-Q-K(γE-X70)-D-S-K-A-A-Q-D-F-I-E-W-L-K-Aib-G-G-P-S-S-G-A-P-P-P-S-NH2 |
| 165 | H-dSer-Q-G-T-F-T-S-D-L-S-K-Q-K(γE-x53)-E-S-R-R-A-Q-D-F-I-E-W-L-K-E-G-G-P-S-S-G-K-P-P-P-S-NH2 |
| 166 | H-dSer-Q-G-T-F-T-S-D-L-S-K-Q-K(γE-X70)-D-S-Q-A-A-Q-D-F-I-E-W-L-K-N-T-G-P-S-S-G-A-P-P-P-S-NH2 |
| 167 | H-dSer-Q-G-T-F-T-S-D-L-S-K-Q-K(γE-x59)-D-S-R-R-A-Q-D-F-I-E-W-L-K-N-G-G-P-S-S-G-A-P-P-P-S-NH2 |
| 168 | H-dSer-Q-G-T-F-T-S-D-L-S-K-Q-K(γE-x61)-D-S-R-R-A-Q-D-F-I-E-W-L-K-N-G-G-P-S-S-G-A-P-P-P-S-NH2 |
| 169 | H-dSer-Q-G-T-F-T-S-D-L-S-K-Q-K(γE-x64)-D-S-R-R-A-Q-D-F-I-E-W-L-K-N-G-G-P-S-S-G-A-P-P-P-S-NH2 |
| 170 | H-dSer-Q-G-T-F-T-S-D-L-S-K-Q-K(γE-x65)-D-S-R-R-A-Q-D-F-I-E-W-L-K-N-G-G-P-S-S-G-A-P-P-P-S-NH2 |
| 171 | H-dSer-Q-G-T-F-T-S-D-L-S-K-Q-K(γE-x73)-D-S-R-R-A-Q-D-F-I-E-W-L-K-N-G-G-P-S-S-G-A-P-P-P-S-NH2 |
| 172 | H-dSer-Q-G-T-F-T-S-D-L-S-K-Q-K(γE-x53)-E-S-R-R-A-Q-D-F-I-E-W-L-K-R-G-G-P-S-S-G-E-P-P-P-S-NH2 |
| 173 | H-dSer-Q-G-T-F-T-S-D-L-S-K-Q-K(γE-x53)-D-S-K-A-A-Q-D-F-I-E-W-L-K-S-G-G-P-S-S-G-A-P-P-P-S-NH2 |
| 174 | H-Aib-Q-G-T-F-T-S-D-L-S-K-Q-K(γE-X70)-D-E-Q-R-A-K-E-F-I-E-W-L-K-S-G-G-P-S-S-G-A-P-P-P-S-NH2 |
| 175 | H-Aib-Q-G-T-F-T-S-D-L-S-K-Q-K(γE-X70)-D-E-Q-R-A-K-D-F-I-E-W-L-K-S-G-G-P-S-S-G-A-P-P-P-S-NH2 |
| 176 | H-Aib-Q-G-T-F-T-S-D-L-S-K-Q-K(γE-X70)-D-E-Q-R-A-K-E-F-I-E-W-L-K-S-G-G-P-S-S-G-A-P-P-P-S-NH2 |
| 177 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH[(CH2—CH2—O)24-CH2—CH2—COOH] |
| 178 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH[(CH2—CH2—O)4-CH2—CH2—COOH] |
| 179 | H-S-MeQ-G-T-F-T-S-D-L-S-K-Q-K(γE-x53)-E-S-R-R-A-Q-D-F-I-E-W-L-K-N-G-G-P-S-S-G-A-P-P-P-S-NH2 |
| 180 | H-S-MeQ-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 181 | H-Aib-Q-G-T-F-T-S-D-L-S-K-Q-K(γE-x53)-D-S-R-R-A-Q-D-F-I-E-W-L-K-A-G-G-P-S-S-G-A-P-P-P-S-NH2 |
| 182 | H-Aib-Q-G-T-F-T-S-D-L-S-K-Q-M-D-S-R-R-A-Q-D-F-I-E-W-L-K-N-G-G-P-S-S-G-A-P-P-P-S-NH2 |
| 183 | H-dSer-Q-G-T-F-T-S-D-L-S-K-Q-K-D-S-R-R-A-Q-D-F-I-E-W-L-K-N-G-G-P-S-S-G-A-P-P-P-S-NH2 |
| 184 | H-dSer-Q-G-T-F-T-S-D-L-S-K-Q-M-E-S-R-R-A-Q-D-F-I-E-W-L-K-A-G-G-P-S-S-G-A-P-P-P-S-NH2 |
| 185 | H-dSer-Q-G-T-F-T-S-D-L-S-K-Q-M-D-S-R-R-A-Q-D-F-I-E-W-L-K-R-G-G-P-S-S-G-A-P-P-P-S-NH2 |
| 186 | H-dSer-Q-G-T-F-T-S-D-L-S-K-Q-M-D-S-R-R-A-Q-D-F-I-E-W-L-K-K-G-G-P-S-S-G-A-P-P-P-S-NH2 |

TABLE 10-continued

Sequences

| SEQ. ID | sequence |
|---|---|
| 187 | H-dSer-Q-G-T-F-T-S-D-L-S-K-Q-M-D-S-R-R-A-Q-D-F-I-E-W-L-K-Aib-G-G-P-S-S-G-A-P-P-P-S-NH2 |
| 188 | H-dSer-Q-G-T-F-T-S-D-L-S-K-Q-M-D-S-R-R-A-Q-D-F-I-E-W-L-K-A-G-G-P-S-S-G-A-P-P-P-S-NH2 |
| 189 | H-dSer-Q-G-T-F-T-S-D-L-S-K-Q-M-E-S-K-A-A-Q-D-F-I-E-W-L-K-A-G-G-P-S-S-G-A-P-P-P-S-NH2 |
| 190 | H-dSer-Q-G-T-F-T-S-D-L-S-K-Q-M-E-S-R-R-A-Aib-D-F-I-E-W-L-K-A-G-G-P-S-S-G-A-P-P-P-S-NH2 |
| 191 | H-dSer-Q-G-T-F-T-S-D-L-S-K-Q-Nle-E-S-Q-A-A-Q-D-F-I-E-W-L-K-A-G-G-P-S-S-G-A-P-P-P-S-NH2 |
| 192 | H-dSer-Q-G-T-F-T-S-D-L-S-K-Q-Nle-D-S-K-A-A-Q-D-F-I-E-W-L-K-A-G-G-P-S-S-G-A-P-P-P-S-NH2 |
| 193 | H-dSer-Q-G-T-F-T-S-D-L-S-K-Q-Nle-D-S-Q-A-A-Q-D-F-I-E-W-L-K-A-G-G-P-S-S-G-A-P-P-P-S-NH2 |
| 194 | H-dSer-Q-G-T-F-T-S-D-L-S-K-Q-K(Ac)-E-S-R-R-A-Q-D-F-I-E-W-L-K-A-G-G-P-S-S-G-A-P-P-P-S-NH2 |
| 195 | H-A-E-G-T-F-T-S-D-V-S-S-Y-L-E-G-Q-A-A-K(γE-x53)-E-I-A-W-L-V-R-G-R-G-OH |
| 196 | H-dSer-Q-G-T-F-T-S-D-L-S-K-Q-K(γE-x70)-D-S-K-R-A-Aib-D-F-I-E-W-L-K-A-G-G-P-S-S-G-A-P-P-P-S-NH2 |
| 197 | H-Aib-Q-G-T-F-T-S-D-L-S-K-Q-K(γE-x70)-D-E-Q-R-A-K-L-F-I-E-W-L-K-A-G-G-P-S-S-G-A-P-P-P-S-NH2 |
| 198 | H-Aib-Q-G-T-F-T-S-D-L-S-K-Q-K(γE-x70)-D-S-R-R-A-Q-L-F-I-E-W-L-K-A-G-G-P-S-S-G-A-P-P-P-S-NH2 |
| 199 | H-Aib-Q-G-T-F-T-S-D-L-S-K-Q-K(γE-x70)-D-E-Q-R-A-K-D-F-I-E-W-L-K-A-dAla-G-P-S-S-G-A-P-P-P-S-NH2 |
| 200 | H-Aib-Q-G-T-F-T-S-D-L-S-K-Q-K(γE-x70)-D-E-Q-R-A-K-L-F-I-E-W-L-K-A-dAla-G-P-S-S-G-A-P-P-P-S-NH2 |
| 201 | H-Aib-Q-G-T-F-T-S-D-L-S-K-Q-K(γE-x76)-D-E-Q-A-A-K-L-F-I-E-W-L-K-A-dAla-G-P-S-S-G-A-P-P-P-S-NH2 |
| 202 | H-Aib-Q-G-T-F-T-S-D-L-S-K-Q-K(γE-x76)-E-S-R-A-A-Q-D-F-I-E-W-L-K-A-G-G-P-S-S-G-A-P-P-P-S-NH2 |
| 203 | H-Aib-Q-G-T-F-T-S-D-L-S-K-Q-K(γE-x76)-E-S-R-A-A-Q-L-F-I-E-W-L-K-A-G-G-P-S-S-G-A-P-P-P-S-NH2 |
| 204 | H-Aib-Q-G-T-F-T-S-D-L-S-K-Q-K(γE-x76)-E-S-R-A-A-Q-L-F-I-E-W-L-K-A-dAla-G-P-S-S-G-A-P-P-P-S-NH2 |
| 205 | H-Aib-Q-G-T-F-T-S-D-L-S-K-Q-K(γE-x70)-E-S-R-A-A-Q-L-F-I-E-W-L-K-A-dAla-G-P-S-S-G-A-P-P-P-S-NH2 |
| 206 | H-Aib-Q-G-T-F-T-S-D-L-S-K-Q-K(γE-x70)-D-E-Q-K-A-K-L-F-I-E-W-L-K-S-G-G-P-S-S-G-A-P-P-P-S-NH2 |
| 207 | H-Aib-Q-G-T-F-T-S-D-L-S-K-Q-K(γE-γE-x53)-D-E-Q-R-A-K-E-F-I-E-W-L-K-S-G-G-P-S-S-G-A-P-P-P-S-NH2 |
| 208 | H-S-H-G-T-F-T-S-D-L-S-K-Q-K(γE-x53)-E-S-R-R-A-Q-D-F-I-E-W-L-K-A-G-G-P-S-S-G-A-P-P-P-S-NH2 |
| 209 | H-Aib-Q-G-T-F-T-S-D-L-S-K-Q-K(γE-x70)-D-K-R-A-Q-D-F-I-E-W-L-K-A-dAla-G-P-S-S-G-A-P-P-P-S-NH2 |
| 210 | H-Aib-Q-G-T-F-T-S-D-L-S-K-Q-K(γE-x70)-D-K-R-A-A-Q-L-F-I-E-W-L-K-A-dAla-G-P-S-S-G-A-P-P-P-S-NH2 |
| 211 | H-Aib-Q-G-T-F-T-S-D-L-S-K-Q-K(γE-x70)-D-K-R-A-A-Q-L-F-I-E-W-L-K-A-dAla-G-P-S-S-G-A-P-P-P-S-NH2 |

TABLE 10-continued

| SEQ. ID | sequence |
|---|---|
| 212 | H-Aib-Q-G-T-F-T-S-D-L-S-K-Q-K(γE-x76)-D-K-R-A-A-Q-L-F-I-E-W-L-K-A-dAla-G-P-S-S-G-A-P-P-P-S-NH2 |
| 213 | H-Aib-Q-G-T-F-T-S-D-L-S-K-Q-K(γE-x70)-D-E-A-A-K-L-F-I-E-W-L-K-A-G-G-P-S-S-G-A-P-P-P-S-NH2 |
| 214 | H-Aib-Q-G-T-F-T-S-D-L-S-K-Q-K(γE-X70)-D-E-A-A-R-L-F-I-E-W-L-K-A-G-G-P-S-S-G-A-P-P-P-S-NH2 |
| 215 | H-Aib-Q-G-T-F-T-S-D-L-S-K-Q-K(γE-X70)-E-E-A-A-R-L-F-I-E-W-L-K-A-G-G-P-S-S-G-A-P-P-P-S-NH2 |
| 216 | H-Aib-Q-G-T-F-T-S-D-L-S-K-Q-K(γE-X70)-D-E-A-A-R-L-F-I-E-W-L-K-A-G-G-P-S-S-G-A-P-P-P-S-NH2 |
| 217 | H-Aib-H-G-T-F-T-S-D-L-S-K-Q-K(γE-X70)-E-E-A-A-R-L-F-I-E-W-L-K-A-G-G-P-S-S-G-A-P-P-P-S-NH2 |
| 218 | H-Aib-H-G-T-F-T-S-D-L-S-K-Q-K(γE-X70)-D-E-A-A-R-L-F-I-E-W-L-K-A-G-G-P-S-S-G-A-P-P-P-S-NH2 |
| 219 | H-dSer-H-G-T-F-T-S-D-L-S-K-Q-K(γE-X70)-E-E-A-A-R-L-F-I-E-W-L-K-A-G-G-P-S-S-G-A-P-P-P-S-NH2 |
| 220 | H-dSer-H-G-T-F-T-S-D-L-S-K-Q-K(γE-X70)-D-E-A-A-R-L-F-I-E-W-L-K-A-G-G-P-S-S-G-A-P-P-P-S-NH2 |
| 221 | H-dSer-Q-G-T-F-T-S-D-L-S-K-Q-K(γE-x53)-D-E-A-A-R-L-F-I-E-W-L-K-A-G-G-P-S-S-G-A-P-P-P-S-NH2 |
| 222 | H-dSer-Q-G-T-F-T-S-D-L-S-K-Q-K(γE-X70)-D-E-A-A-R-L-F-I-E-W-L-K-A-G-G-P-S-S-G-A-P-P-P-S-NH2 |
| 223 | H-dSer-Q-G-T-F-T-S-D-L-S-K-Q-K(γE-x70)-E-E-A-A-R-L-F-I-E-W-L-K-A-G-G-P-S-S-G-A-P-P-P-S-NH2 |
| 224 | H-Aib-Q-G-T-F-T-S-D-L-S-K-Q-L-D-E-E-A-A-R-L-F-I-E-W-L-K-A-G-G-P-S-S-G-A-P-P-P-S-NH2 |
| 225 | H-Aib-Q-G-T-F-T-S-D-L-S-K-Q-L-E-E-E-A-A-R-L-F-I-E-W-L-K-A-G-G-P-S-S-G-A-P-P-P-S-NH2 |
| 226 | H-Aib-Q-G-T-F-T-S-D-L-S-K-Q-K(γE-γE-x53)-D-E-A-A-R-L-F-I-E-W-L-K-A-G-G-P-S-S-G-A-P-P-P-S-NH2 |
| 227 | H-Aib-H-G-T-F-T-S-D-L-S-K-Q-K(γE-γE-x53)-D-E-A-A-R-L-F-I-E-W-L-K-A-G-G-P-S-S-G-A-P-P-P-S-NH2 |
| 228 | H-Aib-Q-G-T-F-T-S-D-L-S-K-Q-K(γE-γE-x53)-E-E-A-A-R-L-F-I-E-W-L-K-A-G-G-P-S-S-G-A-P-P-P-S-NH2 |
| 229 | H-Aib-H-G-T-F-T-S-D-L-S-K-Q-K(γE-γE-x53)-E-E-A-A-R-L-F-I-E-W-L-K-A-G-G-P-S-S-G-A-P-P-P-S-NH2 |

The invention claimed is:
1. A peptidic compound having formula (I):

$$R^1-Z-R^2 \quad (I)$$

or a salt, or solvate thereof,
wherein Z is a peptide moiety having formula (II)

His-X2-X3-Gly-Thr-Phe-Thr-Ser-Asp-Leu-Ser-Lys-Gln X14-X15-X16-X17-X18-Ala-X20-X21-Phe-Ile-Glu-Trp-Leu-Lys-X28-X29-Gly-Pro-Ser-Ser-Gly-X35-Pro-Pro-Pro-X39-X40 (II)

wherein
X2 is an amino acid residue selected from Ser, D-Ser, or Aib,
X3 is an amino acid residue selected from Gln, His, and α-amino-functionalized Gln, wherein Gln is optionally functionalized in that an H of the α-amino group is substituted by ($C_1$-$C_4$)-alkyl,
X14 is an amino acid residue having a side chain with a functionalized —$NH_2$ group, wherein the functionalized —$NH_2$ side chain group is functionalized by —C(O)—$R^5$, —C(O)O—$R^5$, —C(O)NH—$R^5$, —S(O)$_2$—$R^5$ or —$R^5$, wherein $R^5$ is a moiety up to 100 carbon atoms and optionally heteroatoms independently selected from halogen, N, O, S, P and combinations thereof,
X15 is an amino acid residue selected from Glu and Asp,
X16 is an amino acid residue selected from Ser, Glu, and Lys,
X17 is an amino acid residue selected from Arg, Glu, Gln, Leu, Aib, and Lys,
X18 is an amino acid residue selected from Arg, Ala, and Lys,
X20 is an amino acid residue selected from Gln, Arg, Lys, His, Glu, and Aib,
X21 is an amino acid residue selected from Asp, Leu, and Glu,
X28 is an amino acid residue selected from Asn, Arg, Lys, Aib, Ser, Glu, Ala, and Asp,
X29 is an amino acid residue selected from Gly, Ala, D-Ala, and Thr,
X35 is an amino acid residue selected from Ala, Glu, Arg, and Lys,
X39 is Ser or is absent, and
X40 is absent or is an amino acid residue having a side chain with an —$NH_2$ group, wherein the —$NH_2$ side chain group is optionally functionalized by —C(O)—$R^5$, —C(O)O—$R^5$, —C(O)NH—$R^5$, —S(O)$_2$—$R^5$ or —$R^5$, wherein $R^5$ is a moiety comprising up to 100 carbon atoms and optionally heteroatoms independently selected from halogen, N, O, S, P and combinations thereof,
$R^1$ is the N-terminal group of the peptidic compound and is selected from —$NH_2$ or mono- or bisfunctionalized $NH_2$,
wherein the mono- or bisfunctionalized $NH_2$ is selected from the group consisting of —NH[($C_1$-$C_5$)alkyl], —N[($C_1$-$C_5$)alkyl]$_2$, —NH[($C_0$-$C_4$)alkylene-($C_3$-$C_8$)cycloalkyl], —NH—C(O)—H, —NH—C(O)—($C_1$-$C_5$)-alkyl, and —NH—C(O)—($C_0$-$C_3$)alkylene-($C_3$-$C_8$)cycloalkyl, in which alkyl or cycloalkyl is unsubstituted or up to 5-fold substituted by —OH or halogen selected from F, Cl, Br, and I,
$R^2$ is the C-terminal group of the peptidic compound and is selected from (i) —OH and functionalized —OH,
wherein the functionalized —OH is selected from —O—($C_1$-$C_{20}$)alkyl and —O($C_0$-$C_8$)alkylene-($C_3$-$C_8$)cycloalkyl, or
(ii) —$NH_2$ or mono- or bisfunctionalized $NH_2$,
wherein the mono- or bisfunctionalized $NH_2$ is selected from the group consisting of —NH[($C_1$-$C_{30}$)alkyl], —N[($C_1$-$C_{30}$)alkyl]$_2$, —NH[($C_0$-$C_8$)alkylene-($C_3$-$C_8$)cycloalkyl], —N[$C_0$-$C_8$)alkylene-($C_3$-$C_8$)cycloalkyl]$_2$, —NH[($CH_2$—$CH_2$—O)$_{1-40}$—($C_1$-$C_4$)alkyl], —NH—($C_3$-$C_8$) heterocyclyl, and —NH—($C_0$-$C_8$)alkylene-aryl,
wherein aryl is selected from phenyl or naphthyl,
the ($C_3$-$C_8$)-heterocyclyl contains 1 N-atom and optionally two additional heteroatoms selected from O, N, and S, and
alkyl or cycloalkyl is unsubstituted or up to 5-fold substituted by —OH or a halogen selected from F, Cl, Br, and I.

2. The compound, salt, or solvate according to claim 1, wherein
X14 is an amino acid residue selected from Lys, Orn, Dab, and Dap, wherein the —$NH_2$ side chain group is functionalized by —C(O)—$R^5$, and
X40 is an amino acid residue selected from Lys, Orn, Dab, and Dap, wherein the —$NH_2$ side chain group is optionally functionalized by —C(O)—$R^5$,
where $R^5$ is a lipophilic moiety selected from an acyclic ($C_4$-$C_{30}$) hydrocarbon group which is linear, branched, saturated, or unsaturated, or a cyclic hydrocarbon group which is saturated, unsaturated, or aromatic, wherein the lipophilic moiety is optionally attached to the —$NH_2$ side chain group by a linker selected from the group consisting of (β-Ala)$_{1-4}$, (γ-Glu)$_{1-4}$, (ε-Ahx)$_{1-4}$, and (GABA)$_{1-4}$ in all stereoisomeric forms.

3. The compound, salt, or solvate according to claim 1, wherein
X14 is an amino acid residue selected from Lys, Orn, Dab, and Dap, wherein the —$NH_2$ side chain group is functionalized by —C(O)—$R^5$,
X40 is an amino acid residue selected from Lys, Orn, Dab, and Dap, wherein the —$NH_2$ side chain group is optionally functionalized by —C(O)—$R^5$, and —C(O)—$R^5$ is selected from the group consisting of (S)-4-Carboxy-4-hexadecanoylamino-butyryl-, (S)-4-Carboxy-4-octadecanoylamino-butyryl-,4-Hexadecanoylamino-butyryl-, 4-{3-[(R)-2,5,7,8-tetramethyl-2-((4R,8R)-4,8, 12-trimethyl-tridecyl)-chroman-6-yloxycarbonyl]-propionylamino}-butyryl-, 4-octadecanoylamino-butyryl-, 4-((Z)-octadec-9-enoylamino)-butyryl-, 6-[(4,4-Diphenyl-cyclohexyloxy)-hydroxy-phosphoryloxy]-hexanoyl-, Hexadecanoyl-, (S)-4-Carboxy-4-(15-carboxy-pentadecanoylamino)-butyryl-, (S)-4-Carboxy-4-{3-[3-((2S,3R,4S,5R)-5-carboxy-2,3,4,5-tetrahydroxy-pentanoylamino)-propionylamino]-propionylamino}-butyryl, (S)-4-Carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-Carboxy-4-((9Z,12Z)-octadeca-9, 12-dienoylamino)-butyryl-, (S)-4-Carboxy-4-[6-((2S,3R,4S,5R)-5-carboxy-2,3,4, 5-tetrahydroxy-pentanoylamino)-hexanoylamino]-butyryl, (S)-4-Carboxy-4-((2S,3R,4S, 5R)-5-carboxy-2,3,4,5-tetrahydroxy-pentanoylamino)-butyryl, (S)-4-Carboxy-4-tetradecanoylamino-butyryl-, (S)-4-(11-Benzyloxycarbonyl-undecanoylamino)-4-carboxy-butyryl, (S)-4-Carboxy-4-[11-((2S,3R,4R, 5R)-2,3,4,5,6-pentahydroxy-hexylcarbamoyl)-undecanoylamino]-butyryl-, (S)-4-Carboxy-4-((Z)-octadec- 9-enoylamino)-butyryl-, (S)-4-Carboxy-4-(4-dodecyloxy-benzoylamino)-butyryl-, (S)-4-Carboxy-4-henicosanoylamino-butyryl-, (S)-4-Carboxy-4-docosanoylamino-butyryl-, (S)-4-Carboxy-4-((Z)-nonadec-10-enoylamino)-butyryl-, (S)-4-Carboxy-4-(4-decyloxy-benzoylamino)-butyryl-, (S)-4-Carboxy-4-[(4'-octyloxy-biphenyl-4-carbonyl)-amino]-butyryl-, (S)-4-Carboxy-4-(12-phenyl-dodecanoylamino)-butyryl-, (S)-4-Carboxy-4-icosanoylamino-butyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylamino-propionylamino)-propionyl-, 3-(3-Hexadecanoylamino-propionylamino)-propionyl-, 3-Hexadecanoylamino-propionyl-, (S)-4-Carboxy-4-[(R)-4-((3R,5S,7R,8R,9R,10S,12S,13R,14R,17R)-3,7,12-trihydroxy-8,10,13-trimethyl-hexadecahydro-cyclopenta[a]phenanthren-17-yl)-pentanoylamino]-butyryl-, (S)-4-Carboxy-4-[(R)-4-((3R,5R,8R,9S,10S,13R,14S,17R)-3-hydroxy-10,13-dimethyl-hexadecahydro-cyclopenta[a]phenanthren-17-yl)-pentanoylamino]-butyryl-, (S)-4-Carboxy-4-((9S,10R)-9,10,16-trihydroxy-hexadecanoylamino)-butyryl-, Tetradecanoyl-, 11-Carboxy-undecanoyl-, 11-Benzyloxycarbonyl-undecanoyl, (S)-4-Carboxy-4-((S)-4-carboxy-4-tetradecanoylamino-butyrylamino)-butyryl-, 6-[Hydroxy-(naphthalen-2-yloxy)-phosphoryloxy]-hexanoyl-, 6-[Hydroxy-(5-phenyl-pentyloxy)-phosphoryloxy]-hexanoyl-, 4-(Naphthalene-2-sulfonylamino)-4-oxo-butyryl-, 4-(Biphenyl-4-sulfonylamino)-4-oxo-butyryl-, (S)-4-Carboxy-4-{(S)-4-carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl-, (S)-4-Carboxy-4-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl, (S)-4-Carboxy-2-{(S)-4-carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyrylamino}-butyryl, (S)-4-Carboxy-2-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetylamino]-butyryl, (S)-4-Carboxy-4-{(S)-4-carboxy-4-[2-(2-{2-[(S)-4-carboxy-4-(17-carboxy-heptadecanoylamino)-butyrylamino]-ethoxy}-ethoxy)-acetylamino]-butyrylamino}-butyryl, (S)-4-Carboxy-4-[2-(2-{2-[(S)-4-carboxy-4-(17-carboxy-heptadecanoylamino)-butyrylamino]-ethoxy}-ethoxy)-acetylamino]-butyryl, (S)-4-Carboxy-2-{(S)-4-carboxy-2-[2-(2-{2-[(S)-4-carboxy-4-(17-carboxy-heptadecanoylamino)-butyrylamino]-ethoxy}-ethoxy)-acetylamino]-butyrylamino}-butyryl, (S)-4-Carboxy-2-[2-(2-{2-[(S)-4-carboxy-4-(17-carboxy-heptadecanoylamino)-butyrylamino]-ethoxy}-ethoxy)-acetylamino]-butyryl, 2-(2-{2-[2-(2-{2-[(S)-4-Carboxy-4-(17-carboxy-heptadecanoylamino)-butyrylamino]-ethoxy}-ethoxy)-acetylamino]-ethoxy}-ethoxy)-acetyl-, 2-(2-{2-[(S)-4-Carboxy-4-(17-carboxy-heptadecanoylamino)-butyrylamino]-ethoxy}-ethoxy)-acetyl, (S)-4-Carboxy-4-((S)-4-carboxy-4-{(S)-4-carboxy-4-[(S)-4-carboxy-4-(19-carboxy-nonadecanoylamino)-butyrylamino]-butyrylamino}-butyrylamino)-butyryl, 2-(2-{2-[2-(2-{2-[(S)-4-Carboxy-4-(16-1H-tetrazol-5-yl-hexadecanoylamino)-butyrylamino]-ethoxy}-ethoxy)-acetylamino]-ethoxy}-ethoxy)-acetyl, 2-(2-{2-[2-(2-{2-[(S)-4-Carboxy-4-(16-carboxy-hexadecanoylamino)-butyrylamino]-ethoxy}-ethoxy)-acetylamino]-ethoxy}-ethoxy)-acetyl, (S)-4-Carboxy-4-{(S)-4-carboxy-4-[(S)-4-carboxy-4-(17-carboxy-heptadecanoylamino)-butyrylamino]-butyrylamino}-butyryl, (S)-4-Carboxy-4-((S)-4-carboxy-4-{2-[2-(2-{2-[2-(2-{(S)-4-carboxy-4-[10-(4-carboxy-phenoxy)-decanoylamino]-butyrylamino}-ethoxy)-ethoxy]-acetylamino}-ethoxy)-ethoxy]-acetylamino}-butyryl, (S)-4-Carboxy-4-{(S)-4-carboxy-4-[2-(2-{2-[2-(2-{2-[(S)-4-carboxy-4-(7-carboxy-heptanoylamino)-butyrylamino]-ethoxy}-ethoxy)-acetylamino]-ethoxy}-ethoxy)-acetylamino]-butyrylamino}-butyryl, (S)-4-Carboxy-4-{(S)-4-carboxy-4-[2-(2-{2-[2-(2-{2-[(S)-4-carboxy-4-(11-carboxy-undecanoylamino)-butyrylamino]-ethoxy}-ethoxy)-acetylamino]-ethoxy}-ethoxy)-acetylamino]-butyrylamino}-butyryl, (S)-4-Carboxy-4-{(S)-4-carboxy-4-[2-(2-{2-[2-(2-{2-[(S)-4-carboxy-4-(13-carboxy-tridecanoylamino)-butyrylamino]-ethoxy}-ethoxy)-acetylamino]-ethoxy}-ethoxy)-acetylamino]-butyrylamino}-butyryl, (S)-4-Carboxy-4-{(S)-4-carboxy-4-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetylamino]-butyrylamino}-butyryl, and (S)-4-Carboxy-4-{(S)-4-carboxy-4-[2-(2-{2-[2-(4-[2-{2-[(S)-4-carboxy-4-(19-carboxy-nonadecanoylamino)-butyrylamino]-ethoxy}-ethoxy)-acetylamino]-ethoxy}-ethoxy)-acetylamino]-butyrylamino}-butyryl.

4. The compound, salt or solvate according to claim 1, wherein
   $R^1$ is —NH$_2$,
   $R^2$ is —NH$_2$, or
   $R^1$ and $R^2$ are —NH$_2$.

5. The compound, salt or solvate according to claim 1 wherein X14 is Lys, which is functionalized with a group —C(O)R$^5$, wherein R$^5$ is a moiety comprising up to 100 carbon atoms and optionally heteroatoms independently selected from halogen, N, O, S, P and combinations thereof.

6. The compound, salt or solvate according to claim 1, wherein
   X14 is Lys, which is functionalized with a group —C(O)R$^5$, wherein R$^5$ is an acyclic linear or branched (C$_{12}$-C$_{22}$) saturated hydrocarbon group attached directly to the —NH$_2$ side chain group or attached to the —NH$_2$ side chain group by a linker selected from the group consisting of β-Ala, γ-Glu, β-Ala-β-Ala, and γ-Glu-γ-Glu in all stereoisomeric forms.

7. The compound, salt or solvate according to claim 1, wherein
   X2 is an amino acid residue selected from Ser, D-Ser, and Aib,
   X3 is an amino acid residue selected from Gln, His, or α-amino-functionalized Gln, wherein Gln is optionally functionalized in that an H of the α-amino group is substituted by (C$_1$-C$_4$)-alkyl,
   X14 is an amino acid residue selected from Lys, Orn, Dab, and Dap, wherein the —NH$_2$ side chain group is functionalized by —C(O)—R$^5$,
   X15 is an amino acid residue selected from Glu and Asp,
   X16 is an amino acid residue selected from Ser, Lys, and Glu,
   X17 is an amino acid residue selected from Arg, Glu, Gln, Leu, and Lys,
   X18 is an amino acid residue selected from Arg and Ala, X20 is an amino acid residue selected from Gln, Arg, Lys, and Aib, X21 is an amino acid residue selected from Asp, Leu, and Glu, X28 is an amino acid residue selected from Asn, Arg, Lys, Aib, Ser, Glu, Asp, and Ala, X29 is an amino acid residue selected from Gly, Ala, D-Ala, and Thr, X35 is an amino acid residue selected from Ala and Glu, X39 is Ser or is absent, and X40 is either absent or is Lys, wherein the —NH$_2$ side chain group is optionally functionalized by —C(O)—R$^5$, wherein R$^5$ is a lipophilic moiety selected from an acyclic (C$_4$-C$_{30}$) hydrocarbon group which is linear, branched, saturated, or unsaturated, or a cyclic hydrocarbon group, which is saturated, unsaturated, or aromatic, wherein the lipophilic moiety is optionally attached to the —NH$_2$ side chain group by a linker selected from the group consisting of (β-Ala)$_{1-4}$, (γ-Glu)$_{1-4}$, (ε-Ahx)$_{1-4}$, and (GABA)$_{1-4}$ in all stereoisomeric forms.

8. The compound, salt or solvate according to claim 1, wherein

X2 is an amino acid residue selected from D-Ser and Aib,

X3 is Gln,

X14 is an amino acid residue selected from Lys or Orn, wherein the —NH$_2$ side chain group is functionalized by —C(O)—R$^5$, X15 is an amino acid residue selected from Glu and Asp, X16 is an amino acid residue selected from Ser and Glu, X17 is an amino acid residue selected from Arg, Gln, and Lys, X18 is an amino acid residue selected from Arg and Ala, X20 is an amino acid residue selected from Gln, Arg, Lys, and Aib, X21 is an amino acid residue selected from Asp, Leu, and Glu, X28 is an amino acid residue selected from Asn, Arg, Lys, Aib, Ser, and Ala, X29 is an amino acid residue selected from Gly, Ala, and Thr, X35 is Ala, X39 is Ser or is absent, and X40 is either absent or is Lys, wherein the —NH$_2$ side chain group is optionally functionalized by —C(O)—R$^5$, wherein R$^5$ is a lipophilic moiety selected from an acyclic (C$_4$-C$_{30}$) hydrocarbon group which is linear, branched, saturated, or unsaturated, or a cyclic hydrocarbon group which is saturated, unsaturated, or aromatic, wherein the lipophilic moiety is optionally attached to the —NH$_2$ side chain group by a linker selected from the group consisting of (β-Ala)$_{1-4}$, (γ-Glu)$_{1-4}$, (ε-Ahx)$_{1-4}$, and (GABA)$_{1-4}$ in all stereoisomeric forms.

9. The compound, or salt or solvate thereof, according to claim 1, wherein X20 is an amino acid residue selected from Gln, Lys, and Aib.

10. The compound, salt or solvate according to claim 1, wherein

X2 is an amino acid residue selected from D-Ser and Aib,

X3 is Gln,

X14 is Lys, wherein the —NH$_2$ side chain group is functionalized by one of the functional groups selected from the group consisting of 3-(3-octadecanoylamino-propionyl-amino)-propionyl-, 4-hexadecanoylamino-butyryl-, 4-{3-[(R)-2,5,7,8-tetramethyl-2-((4R,8R)-4,8,12-trimethyl-tridecyl)-chroman-6-yloxycarbonyl]-propionylamino}-butyryl-, 4-octadecanoylamino-butyryl-, 4-((Z)-octadec-9-enoylamino)-butyryl-, hexadecanoyl-, (S)-4-carboxy-4-((Z)-octadec-9-enoylamino)-butyryl-, (S)-4-carboxy-4-(4-dodecyloxy-benzoylamino)-butyryl-, (S)-4-carboxy-4-henicosanoylamino-butyryl-, (S)-4-carboxy-4-docosanoylamino-butyryl-, (S)-4-carboxy-4-((Z)-nonadec-10-enoylamino)-butyryl-, (S)-4-carboxy-4-(4-decyloxy-benzoylamino)-butyryl-, (S)-4-carboxy-4-[(4'-octyloxy-biphenyl-4-carbonyl)-amino]-butyryl-, (S)-4-carboxy-4-(12-phenyl-dodecanoylamino)-butyryl-, (S)-4-carboxy-4-((S)-4-carboxy-4-hexadecanoylamino-butyrylamino)-butyryl-, (S)-4-carboxy-4-((S)-4-carboxy-4-octadecanoylamino-butyrylamino)-butyryl-, (S)-4-carboxy-4-{3-[(R)-2,5,7,8-tetramethyl-2-((4R,8R)-4,8,12-trimethyl-tridecyl)-chroman-6-yloxycarbonyl]-propionylamino}-butyryl-, (S)-4-carboxy-4-((9Z,12Z)-octadeca-9,12-dienoylamino)-butyryl-, (S)-4-carboxy-4-octadecanoylamino-butyryl-, and (S)-4-carboxy-4-hexadecanoylamino-butyryl-, X15 is Glu, X16 is Ser, X17 is an amino acid residue selected from Arg, Gln, and Lys, X18 is Ala, X20 is Gln, X21 is Asp, X28 is Ala, X29 is Gly, X35 is Ala, X39 is Ser, and X40 is absent.

11. The compound, salt or solvate according to claim 1, wherein

X2 is Aib,

X3 is Gln,

X14 is Lys, wherein the —NH$_2$ side chain group is optionally functionalized by (S)-4-Carboxy-4-hexadecanoylamino-butyryl- or (S)-4-Carboxy-4-octadecanoylamino-butyryl-, X15 is an amino acid residue selected from Asp and Glu, X16 is an amino acid residue selected from Ser and Glu, X17 is an amino acid residue selected from Gln and Lys, X18 is Ala, X20 is an amino acid residue selected from Gln and Lys, X21 is an amino acid residue selected from Asp and Leu, X28 is Ala, X29 is an amino acid residue selected from Gly and D-Ala, X35 is Ala, X39 is Ser, and X40 is absent.

12. The compound, salt or solvate according to claim 1, wherein

X2 is D-Ser,

X3 is Gln,

X14 is Lys, wherein the —NH$_2$ side chain group is optionally functionalized by (S)-4-carboxy-4-hexadecanoylamino-butyryl- or hexadecanoyl-, X15 is an amino acid residue selected from Glu and Asp, X16 is an amino acid residue selected from Ser and Glu, X17 is an amino acid residue selected from Arg, Glu, Lys, and Aib, X18 is an amino acid residue selected from Arg, Lys, and Ala, X20 is an amino acid residue selected from Gln, Lys, and Aib, X21 is an amino acid residue selected from Asp and Leu,
X28 is an amino acid residue selected from Ala and Asn,
X29 is Gly,
X35 is Ala,
X39 is Ser, and
X40 is absent.

13. The compound, salt or solvate according to claim 1, wherein
X2 is an amino acid residue selected from Aib and D-Ser;
X3 is an amino acid residue selected from Gln and His;
X14 is Lys, wherein the —NH$_2$ side chain group is functionalized by one of the functional groups selected from the group consisting of (S)-4-Carboxy-4-hexadecanoylamino-butyryl-, (S)-4-Carboxy-4-octadecanoylaminobutyryl-, (S)-4-Carboxy-4-((S)-4-carboxy-4-hexadecanoylamino-butyrylamino)-butyryl-, (S)-4-Carboxy-4-((S)-4-carboxy-4-octadecanoylamino-butyrylamino)-butyryl-, 3-(3-Octadecanoylaminopropionylamino)propionyl-, 3-(3-Hexadecanoylaminopropionylamino)-propionyl-, (S)-4-Carboxy-4-henicosanoylamino-butyryl-, 4-Hexadecanoylaminobutyryl-, and 4-octadecanoylamino-butyryl-,
X15 is an amino acid residue selected from Asp and Glu;
X16 is an amino acid residue selected from Ser and Glu;
X17 is an amino acid residue selected from Arg, Gln, Lys, Aib, and Leu;
X18 is an amino acid residue selected from Arg and Ala;
X20 is an amino acid residue selected from Gln, Aib, and Lys;
X21 is an amino acid residue selected from Asp, Glu, and Lys;
X28 is an amino acid residue selected from Asn, Ser, Aib, Ala, and Arg;
X29 is an amino acid residue selected from Gly, Thr, Ala, and D-Ala;
X35 is Ala;
X39 is Ser; and
X40 is absent.

14. The compound, salt or solvate according to claim 1, wherein X14 is functionalized Lys which is functionalized at its ε-amino group with —C(O)—R$^5$, wherein —C(O)—R$^5$ is (S)-4-carboxy-4-hexadecanoyl-amino-butyryl, (S)-4-carboxy-4-octadecanoylamino-butyryl, hexadecanoyl, or octadecanoyl.

15. The compound, salt or solvate according to claim 14, wherein
X2 is an amino acid residue selected from Aib and D-Ser;
X3 is Gln;
X14 is Lys, wherein the —NH$_2$ side chain group is functionalized by one of the functional groups selected from the group consisting of (S)-4-carboxy-4-hexadecanoylamino-butyryl, (S)-4-carboxy-4-octadecanoylaminobutyryl, hexadecanoyl, and octadecanoyl;
X15 is Glu;
X16 is Ser;
X17 is an amino acid residue selected from Arg, Gln, and Lys;
X18 is Ala;
X20 is Gln;
X21 is Asp;
X28 is Ala;
X29 is Gly;
X35 is Ala;
X39 is Ser; and
X40 is absent.

16. The compound, salt or solvate according to claim 1, wherein
X2 is Aib,
X3 is Gln,
X14 is Lys, wherein the —NH$_2$ side chain group is optionally functionalized by (S)-4-Carboxy-4-henicosanoylamino-butyryl- or (S)-4-Carboxy-4-octadecanoylamino-butyryl-,
X15 is Asp,
X16 is an amino acid residue selected from Lys and Glu,
X17 is an amino acid residue selected from Arg and Glu,
X18 is an amino acid residue selected from Ala and Arg,
X20 is an amino acid residue selected from Gln and Lys,
X21 is an amino acid residue selected from Asp and Leu,
X28 is Ala,
X29 is an amino acid residue selected from Gly and D-Ala,
X35 is Ala,
X39 is Ser, and
X40 is absent.

17. The compound, salt or solvate according to claim 1, wherein the compound is any one of SEQ ID NO. 4-181, or a salt or solvate thereof.

18. The compound, salt or solvate according to claim 1, wherein the compound is any one of SEQ ID NO. 4-181, 196-223, 226-229, or a salt or solvate thereof.

19. The compound, salt or solvate according to claim 1, wherein the compound has a high solubility at least one pH value selected from an acidic pH value or at physiological pH value, and wherein the solubility at said at least one pH value is at least 0.5 mg/ml.

20. A pharmaceutical composition comprising the compound, salt or solvate according to claim 1 as an active agent together and at least one pharmaceutically acceptable carrier.

21. The pharmaceutical composition according to claim 20 further comprising at least one additional therapeutically active agent, wherein said additional therapeutically active agent is selected from the group consisting of insulin and insulinic compounds; GLP-1, GLP-1 analogues, and GLP-1 receptor agonists selected from the group consisting of lixisenatide, AVE0010, ZP10, exenatide, exendin-4, ITCA 650, AC-2993, liraglutide, semaglutide, taspoglutide, albiglutide, dulaglutide, recombinant exendin-4, CJC-1134-PC, PB-1023, TTP-054, langlenatide, HM-11260C, CM-3, ORMD-0901, NN-9924, NN-9926, NN-9927, Nodexen, CVX-096, ZYOG-1, ZYD-1, GSK-2374697, DA-3091, MAR-701, MAR709, ZP-2929, ZP-3022, TT-401, BHM-034, MOD-6030, CAM-2036, DA-15864, ARI-2651, ARI-2255, xtenylated exenatide and xtenylated glucagon, and wherein the GLP-1 and GLP-1 analogues are optionally bound by a polymer; dual GLP1/GIP agonists; PYY3-36; pancreatic polypeptide; glucagon receptor agonists; GIP receptor agonists or antagonists; ghrelin antagonists or inverse agonists; xenin; DDP-IV inhibitors; SGLT2 inhibitors; dual SGLT2/SGLT1 inhibitors; biguanides; thiazolidinediones; dual PPAR agonists; sulfonylureas; meglitinides; alpha-glucosidase inhibitors; amylin and pramlintide; GPR119 agonists; GPR40 agonists; GPR120 agonists; GPR142 agonists; systemic or low-absorbable TGR5 agonists; bromocriptine mesylate; inhibitors of 11-beta-HSD; activators of glucokinase; inhibitors of DGAT; inhibitors of protein tyrosinephosphatase 1; inhibitors of glucose-6-phosphatase; inhibitors of fructose-1,6-bisphosphatase; inhibitors of glycogen phosphorylase; inhibitors of phosphoenol pyruvate carboxykinase; inhibitors of glycogen synthase kinase; inhibitors of pyruvate dehydrogenase kinase; alpha2-antagonists; CCR-2 antagonists; modulators of glucose transporter-4; somatostatin receptor 3 agonists; HMG-CoA-reductase inhibitors; fibrates; nicotinic acid and derivatives thereof; nicotinic acid receptor 1 agonists; PPAR-alpha, gamma, or alpha/gamma agonists or modulators; PPAR-delta agonists; ACAT inhibitors; cholesterol absorption inhibitors; bile acid-binding substances; IBAT inhibitors; MTP inhibitors; modulators of PCSK9; HDL-raising compounds; lipid metabolism modulators; PLA2 inhibitors; ApoA-I enhancers; thyroid hormone receptor agonists; cholesterol synthesis inhibitors; omega-3 fatty acids and derivatives thereof; substances for the treatment of obesity selected from the group consisting of sibutramine, tesofensine, tetrahydrolipstatin, CB-1receptor antagonists, MCH-1 antagonists, MC4 receptor agonists and partial agonists, NPY5 or NPY2 antagonists, NPY4 agonists, beta-3-agonists, leptin or leptin mimetics, agonists of the 5HT2c receptor, combinations of bupropione/naltrexone, combinations of bupropione/zonisamide, combinations of bupropione/phentermine, combinations of pramlintide/metreleptin, and combinations of phentermine/topiramate; lipase inhibitors; angiogenesis inhibitors; H3 antagonists; AgRP inhibitors; triple monoamine uptake inhibitors; MetAP2 inhibitors; nasal formulations of the calcium channel blocker diltiazem; inhibitors of fibroblast growth factor receptor 4; prohibitin targeting peptide-1; and drugs for influencing high blood pressure, chronic heart failure, or atherosclerosis selected from the group consisting of angiotensin II receptor antagonists, ACE inhibitors, ECE inhibitors, diuretics, beta-blockers, calcium antagonists, centrally acting hypertensives, antagonists of the alpha-2-adrenergic receptor, inhibitors of neutral endopeptidase, and thrombocyte aggregation inhibitors.

22. The pharmaceutical composition according to claim 20 further comprising at least one additional therapeutically active agent, wherein said at least one additional therapeutically active agent is selected from a GLP-1 compound, an insulinic compound, and a gastrointestinal peptide.

23. The pharmaceutical composition according to claim 20 further comprising at least one additional therapeutically active agent, wherein said additional therapeutically active agent is insulin or an insulinic compound.

24. The compound, salt or solvate according to claim 19, said compound having a high solubility at acidic pH values of pH 4.5 at 25° C., and/or at physiological pH values of pH 7.4 at 25° C.

25. The compound, salt or solvate according to claim 19, wherein the solubility at said acidic pH value and/or at said physiological pH value is at least 1.0 mg/ml.

26. The compound, salt or solvate according to claim 11, wherein X14 is Lys, wherein the —$NH_2$ side chain group is functionalized by (S)-4-Carboxy-4-hexadecanoylamino-butyryl- or (S)-4-Carboxy-4-octadecanoylamino-butyryl-.

27. The compound, salt or solvate according to claim 12, wherein X14 is Lys, wherein the —$NH_2$ side chain group is functionalized by (S)-4-carboxy-4-hexadecanoylamino-butyryl- or hexadecanoyl-.

28. The compound, salt or solvate according to claim 16, wherein X14 is LYS, wherein the —$NH_2$ side chain group is functionalized by (S)-4-Carboxy-4-henicosanoylamino-butyryl- or (S)-4-Carboxy-4-octadecanoylamino-butyryl-.

29. The pharmaceutical composition according to claim 21, wherein the insulin or insulinic compound is selected from the group consisting of insulin glargine; insulin glulisin; insulin detemir; insulin lispro; insulin degludec; insulin aspart; a combination of insulin degludec and insulin aspart; basal insulin and analogues; pegylated insulin; human insulin (rDNA origin); polysialylated insulin; NN1045; insulin in combination with pramlintide; PE0139; fast-acting and short-acting insulins; insulin hydrogel; oral, inhalable, transdermal, and sublingual insulins; and insulinic compounds which are bonded to albumin or another protein by a bifunctional linker.

30. A compound, salt, or hydrate of claim 1.

31. A compound or salt of claim 1.

32. The compound, salt or solvate according to claim 1, wherein $R^5$ is a moiety comprising up to 50 carbon atoms and optionally heteroatoms independently selected from halogen, N, O, S, P and combinations thereof.

33. The compound, salt or solvate according to claim 1, wherein the ($C_3$-$C_8$)-heterocyclyl is selected from azetidinyl, pyrrolidinyl, piperidinyl, morpholinyl, and homopiperidinyl.

34. The compound, salt, or solvate according to claim 1, wherein the compound is the amino acid sequence of SEQ ID NO:24, or a salt, or solvate thereof.

35. The compound, salt, or solvate according to claim 1, wherein the compound is the amino acid sequence of SEQ ID NO:35, or a salt, or solvate thereof.

36. The compound, salt, or solvate according to claim 1, wherein the compound is the amino acid sequence of SEQ ID NO:36, or a salt, or solvate thereof.

37. The compound, salt, or solvate according to claim 1, wherein the compound is the amino acid sequence of SEQ ID NO:44, or a salt, or solvate thereof.

38. The compound, salt, or solvate according to claim 1, wherein the compound is the amino acid sequence of SEQ ID NO:97, or a salt, or solvate thereof.

* * * * *